US008292968B2

(12) United States Patent
Truncale et al.

(10) Patent No.: US 8,292,968 B2
(45) Date of Patent: Oct. 23, 2012

(54) CANCELLOUS CONSTRUCTS, CARTILAGE PARTICLES AND COMBINATIONS OF CANCELLOUS CONSTRUCTS AND CARTILAGE PARTICLES

(75) Inventors: Katherine G. Truncale, Hillsborough, NJ (US); Eric J. Semler, Piscataway, NJ (US); Arthur A. Gertzman, Flemington, NJ (US); Moon Hae Sunwoo, Old Tappan, NJ (US); William W. Tomford, Belmont, MA (US); Roman Shikhanovich, Edison, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

(21) Appl. No.: 12/931,427

(22) Filed: Feb. 1, 2011

(65) Prior Publication Data

US 2011/0166669 A1 Jul. 7, 2011

Related U.S. Application Data

(60) Division of application No. 12/381,072, filed on Mar. 5, 2009, which is a continuation-in-part of application No. 11/657,042, filed on Jan. 24, 2007, now Pat. No. 7,837,740, and a continuation-in-part of application No. 12/043,001, filed on Mar. 5, 2008, now abandoned, and a continuation-in-part of application No. 12/328,306, filed on Dec. 4, 2008, and a continuation-in-part of application No. 12/079,629, filed on Mar. 26, 2008, now abandoned, which is a division of application No. 10/960,960, filed on Oct. 12, 2004, now abandoned.

(60) Provisional application No. 61/189,252, filed on Aug. 15, 2008, provisional application No. 61/205,433, filed on Jan. 15, 2009, provisional application No. 60/904,809, filed on Mar. 6, 2007, provisional application No. 60/996,800, filed on Dec. 5, 2007.

(51) Int. Cl.
*A61F 2/28* (2006.01)
(52) U.S. Cl. .................................................. 623/23.51
(58) Field of Classification Search ............... 623/23.15, 623/23.51
See application file for complete search history.

(56) References Cited

U.S. PATENT DOCUMENTS 3,400,199 A 9/1968 Balassa
(Continued)

FOREIGN PATENT DOCUMENTS

EP 0517030 A2 12/1992
(Continued)

OTHER PUBLICATIONS

Non-final Office Action for U.S. Appl. No. 12/179,034, mailed Jun. 29, 2011.
(Continued)

*Primary Examiner* — Thomas J Sweet
*Assistant Examiner* — Melissa Hoban
(74) *Attorney, Agent, or Firm* — Greenberg Traurig, LLP

(57) ABSTRACT

A construct for repairing articular cartilage defects includes a cap member and a base member. The cap member has an upper section and a stem depending from a central region thereof. The upper section includes a peripheral region. The stem includes a cavity. The base member has first and second ends, the first end including an annular recess dimensioned such that the stem is receivable therein. The first end also includes an annular edge positioned laterally outwardly from the annular recess, for abutting and supporting the peripheral region of the upper section when the stem is received in the annular recess. The base member further includes an island which is surrounded by the annular recess and receivable in the cavity of the stem, such that the island is abuttable with and may thereby support the central region of the upper section when the stem is received in the annular recess.

6 Claims, 34 Drawing Sheets

U.S. PATENT DOCUMENTS

| | | | |
|---|---|---|---|
| 3,476,855 A | 11/1969 | Balassa | |
| 3,478,146 A | 11/1969 | Balssa | |
| 3,551,560 A | 12/1970 | Theile | |
| 3,772,432 A | 11/1973 | Balassa | |
| 3,867,728 A | 2/1975 | Stubstad et al. | |
| 3,966,908 A | 6/1976 | Balassa | |
| 4,060,081 A | 11/1977 | Yannas et al. | |
| 4,172,128 A | 10/1979 | Theile et al. | |
| 4,201,845 A | 5/1980 | Feder et al. | |
| 4,296,100 A | 10/1981 | Franco | |
| 4,378,347 A | 3/1983 | Franco | |
| 4,394,370 A | 7/1983 | Jefferies | |
| 4,400,833 A | 8/1983 | Kurland | |
| 4,442,655 A | 4/1984 | Stroetmann | |
| 4,458,678 A | 7/1984 | Yannas et al. | |
| 4,479,271 A | 10/1984 | Bolesky et al. | |
| 4,501,269 A | 2/1985 | Bagby | |
| 4,505,266 A | 3/1985 | Yannas et al. | |
| 4,600,574 A | 7/1986 | Lindner et al. | |
| 4,609,551 A | 9/1986 | Caplan et al. | |
| 4,627,853 A * | 12/1986 | Campbell et al. | 128/898 |
| 4,642,120 A | 2/1987 | Nevo et al. | |
| 4,656,137 A | 4/1987 | Balassa | |
| 4,681,763 A | 7/1987 | Nathanson et al. | |
| 4,683,195 A | 7/1987 | Mullis et al. | |
| 4,683,202 A | 7/1987 | Mullis | |
| 4,757,017 A | 7/1988 | Cheung | |
| 4,776,173 A | 10/1988 | Kamarei et al. | |
| 4,776,853 A | 10/1988 | Klement et al. | |
| 4,795,467 A | 1/1989 | Piez et al. | |
| 4,801,299 A | 1/1989 | Brendel et al. | |
| 4,837,379 A | 6/1989 | Wienberg | |
| 4,846,835 A | 7/1989 | Grande | |
| 4,880,429 A | 11/1989 | Stone | |
| 4,902,508 A | 2/1990 | Badylak et al. | |
| 4,904,259 A | 2/1990 | Itay | |
| 4,932,973 A | 6/1990 | Gendler | |
| 4,950,296 A | 8/1990 | McIntyre | |
| 4,950,483 A | 8/1990 | Ksander et al. | |
| 4,955,911 A | 9/1990 | Frey et al. | |
| 4,963,146 A | 10/1990 | Li | |
| 4,963,489 A | 10/1990 | Naughton et al. | |
| 4,965,188 A | 10/1990 | Mussis et al. | |
| 4,971,954 A | 11/1990 | Brodsky et al. | |
| 4,976,738 A | 12/1990 | Frey et al. | |
| 4,978,355 A | 12/1990 | Frey et al. | |
| 4,994,084 A | 2/1991 | Brennan | |
| 4,994,559 A | 2/1991 | Moscatelli et al. | |
| 5,002,071 A | 3/1991 | Harrell | |
| 5,002,583 A | 3/1991 | Pitaru et al. | |
| 5,007,934 A | 4/1991 | Stone | |
| 5,032,508 A | 7/1991 | Naughton et al. | |
| 5,041,138 A | 8/1991 | Vacanti et al. | |
| 5,053,049 A | 10/1991 | Campbell | |
| 5,053,050 A | 10/1991 | Itay | |
| 5,067,963 A | 11/1991 | Khouri et al. | |
| 5,067,964 A | 11/1991 | Richmond et al. | |
| 5,073,373 A | 12/1991 | O'Leary et al. | |
| 5,084,051 A | 1/1992 | Tormala et al. | |
| 5,092,887 A | 3/1992 | Gendler | |
| 5,118,512 A | 6/1992 | O'Leary et al. | |
| 5,152,791 A | 10/1992 | Hakamatsuka et al. | |
| 5,155,214 A | 10/1992 | Baird et al. | |
| 5,191,067 A | 3/1993 | Lappi et al. | |
| 5,195,892 A | 3/1993 | Gershberg | |
| 5,206,023 A | 4/1993 | Hunziker | |
| 5,226,914 A | 7/1993 | Caplan et al. | |
| 5,236,456 A | 8/1993 | O'Leary et al. | |
| 5,256,140 A | 10/1993 | Fallick | |
| 5,260,420 A | 11/1993 | Burnouf-Radosevich et al. | |
| 5,266,476 A | 11/1993 | Sussman et al. | |
| 5,270,300 A | 12/1993 | Hunziker | |
| 5,275,826 A | 1/1994 | Badylak et al. | |
| 5,281,422 A | 1/1994 | Badylak et al. | |
| 5,284,155 A | 2/1994 | Treadwell et al. | |
| 5,290,558 A | 3/1994 | O'Leary et al. | |
| 5,298,254 A | 3/1994 | Prewett et al. | |
| 5,302,702 A | 4/1994 | Seddon et al. | |
| 5,306,304 A | 4/1994 | Gendler | |
| 5,306,311 A | 4/1994 | Stone et al. | |
| 5,310,883 A | 5/1994 | Seddon et al. | |
| 5,314,476 A | 5/1994 | Prewett et al. | |
| 5,326,357 A | 7/1994 | Kandel | |
| 5,329,846 A | 7/1994 | Bonutti | |
| 5,336,616 A | 8/1994 | Livesey et al. | |
| 5,338,772 A | 8/1994 | Bauer et al. | |
| 5,352,463 A | 10/1994 | Badylak et al. | |
| 5,354,557 A | 10/1994 | Oppermann et al. | |
| 5,356,629 A | 10/1994 | Sander et al. | |
| 5,368,858 A | 11/1994 | Hunziker | |
| 5,372,821 A | 12/1994 | Badylak et al. | |
| 5,380,328 A | 1/1995 | Morgan | |
| 5,411,885 A | 5/1995 | Marx | |
| 5,425,769 A | 6/1995 | Snyders, Jr. | |
| 5,439,684 A | 8/1995 | Prewett et al. | |
| 5,439,818 A | 8/1995 | Fiddes et al. | |
| 5,443,950 A | 8/1995 | Naughton et al. | |
| 5,445,833 A | 8/1995 | Badylak et al. | |
| 5,464,439 A | 11/1995 | Gendler | |
| 5,466,462 A | 11/1995 | Rosenthal et al. | |
| 5,491,220 A | 2/1996 | Seddon et al. | |
| 5,496,722 A | 3/1996 | Goodwin et al. | |
| 5,507,813 A | 4/1996 | Dowd et al. | |
| 5,510,396 A | 4/1996 | Prewett et al. | |
| 5,512,460 A | 4/1996 | Nauro et al. | |
| 5,513,662 A | 5/1996 | Morse et al. | |
| 5,516,532 A | 5/1996 | Atala et al. | |
| 5,516,533 A | 5/1996 | Badylak et al. | |
| 5,545,222 A | 8/1996 | Bonutti | |
| 5,549,904 A | 8/1996 | Juergensen et al. | |
| 5,554,389 A | 9/1996 | Badylak et al. | |
| 5,556,430 A | 9/1996 | Gendler | |
| 5,569,272 A | 10/1996 | Reed et al. | |
| 5,571,895 A | 11/1996 | Kurokawa et al. | |
| 5,576,288 A | 11/1996 | Lappi et al. | |
| 5,604,293 A | 2/1997 | Fiddes et al. | |
| 5,607,474 A | 3/1997 | Athanasiou et al. | |
| 5,614,496 A | 3/1997 | Dunstan et al. | |
| 5,618,925 A | 4/1997 | Dupont et al. | |
| 5,622,928 A | 4/1997 | Naruo et al. | |
| 5,624,463 A | 4/1997 | Stone et al. | |
| 5,631,011 A | 5/1997 | Wadstrom | |
| 5,632,745 A | 5/1997 | Schwartz | |
| 5,656,598 A | 8/1997 | Dunstan et al. | |
| 5,662,710 A | 9/1997 | Bonutti | |
| 5,679,637 A | 10/1997 | Lappi et al. | |
| 5,681,353 A | 10/1997 | Li et al. | |
| 5,695,998 A | 12/1997 | Badylak et al. | |
| 5,700,476 A | 12/1997 | Rosenthal et al. | |
| 5,700,774 A | 12/1997 | Hattersley et al. | |
| 5,707,962 A | 1/1998 | Chen et al. | |
| 5,713,374 A | 2/1998 | Pachence et al. | |
| 5,716,413 A | 2/1998 | Walter et al. | |
| 5,723,331 A | 3/1998 | Tubo et al. | |
| 5,728,159 A | 3/1998 | Stroever et al. | |
| 5,733,337 A | 3/1998 | Carr, Jr. et al. | |
| 5,736,132 A | 4/1998 | Juergensen et al. | |
| 5,736,372 A | 4/1998 | Vacanti et al. | |
| 5,736,396 A | 4/1998 | Bruder et al. | |
| 5,749,874 A | 5/1998 | Schwartz | |
| 5,755,791 A | 5/1998 | Whitson et al. | |
| 5,759,190 A | 6/1998 | Vibe-Hansen et al. | |
| 5,769,899 A | 6/1998 | Schwartz et al. | |
| 5,770,417 A | 6/1998 | Vacanti et al. | |
| 5,782,835 A | 7/1998 | Hart et al. | |
| 5,782,915 A | 7/1998 | Stone | |
| 5,786,217 A | 7/1998 | Tubo et al. | |
| 5,788,625 A | 8/1998 | Plouhar et al. | |
| 5,800,537 A | 9/1998 | Bell | |
| 5,814,084 A | 9/1998 | Grivas et al. | |
| 5,842,477 A | 12/1998 | Naughton et al. | |
| 5,846,931 A | 12/1998 | Hattersley et al. | |
| 5,853,746 A | 12/1998 | Hunziker | |
| 5,855,620 A | 1/1999 | Bishopric et al. | |
| 5,859,208 A | 1/1999 | Fiddes et al. | |
| 5,863,296 A | 1/1999 | Orton | |
| 5,863,297 A | 1/1999 | Walter et al. | |

| | | | |
|---|---|---|---|
| 5,866,415 A | 2/1999 | Villeneuve | |
| 5,876,452 A | 3/1999 | Athanasiou et al. | |
| 5,881,733 A | 3/1999 | Stone | |
| 5,888,219 A | 3/1999 | Bonutti | |
| 5,891,558 A | 4/1999 | Bell et al. | |
| 5,893,888 A | 4/1999 | Bell | |
| 5,899,936 A | 5/1999 | Goldstein | |
| 5,899,939 A | 5/1999 | Boyce et al. | |
| 5,904,716 A | 5/1999 | Gendler | |
| 5,906,827 A | 5/1999 | Khouri et al. | |
| 5,910,315 A | 6/1999 | Stevenson et al. | |
| 5,916,265 A | 6/1999 | Hu | |
| 5,922,028 A | 7/1999 | Plouhar et al. | |
| 5,948,429 A | 9/1999 | Bell et al. | |
| 5,955,438 A | 9/1999 | Pitaru et al. | |
| 5,964,805 A | 10/1999 | Stone | |
| 5,968,556 A | 10/1999 | Atala et al. | |
| 5,972,368 A | 10/1999 | McKay | |
| 5,972,385 A | 10/1999 | Liu et al. | |
| 5,974,663 A | 11/1999 | Ikeda et al. | |
| 5,989,269 A | 11/1999 | Vibe-Hansen et al. | |
| 5,989,289 A | 11/1999 | Coates et al. | |
| 5,989,866 A | 11/1999 | Deisher et al. | |
| 5,998,170 A | 12/1999 | Arakawa et al. | |
| 6,001,352 A | 12/1999 | Boyan et al. | |
| 6,005,161 A | 12/1999 | Brekke et al. | |
| 6,013,853 A | 1/2000 | Athanasiou et al. | |
| 6,017,348 A | 1/2000 | Hart et al. | |
| 6,025,334 A | 2/2000 | Dupont et al. | |
| 6,025,538 A | 2/2000 | Yaccarino, III | |
| 6,027,743 A | 2/2000 | Khouri et al. | |
| 6,030,635 A | 2/2000 | Gertzman et al. | |
| 6,037,171 A | 3/2000 | Larsson | |
| 6,039,762 A | 3/2000 | McKay | |
| 6,056,777 A | 5/2000 | McDowell | |
| 6,060,640 A | 5/2000 | Pauley et al. | |
| 6,074,663 A | 6/2000 | Delmotte et al. | |
| 6,080,194 A | 6/2000 | Pachence et al. | |
| 6,090,996 A | 7/2000 | Li | |
| 6,090,998 A | 7/2000 | Grooms et al. | |
| 6,096,081 A | 8/2000 | Grivas et al. | |
| 6,096,347 A | 8/2000 | Geddes et al. | |
| 6,110,209 A | 8/2000 | Stone | |
| 6,110,482 A | 8/2000 | Khouri et al. | |
| 6,123,731 A | 9/2000 | Boyce et al. | |
| 6,132,472 A | 10/2000 | Bonutti | |
| 6,143,293 A | 11/2000 | Weiss et al. | |
| 6,146,385 A | 11/2000 | Torrie et al. | |
| 6,156,068 A | 12/2000 | Walter et al. | |
| 6,165,486 A | 12/2000 | Marra et al. | |
| 6,165,487 A | 12/2000 | Ashkar et al. | |
| 6,176,880 B1 | 1/2001 | Plouhar et al. | |
| 6,180,605 B1 | 1/2001 | Chen et al. | |
| 6,183,737 B1 | 2/2001 | Zaleske et al. | |
| 6,189,537 B1 | 2/2001 | Wolfinbarger, Jr. | |
| 6,197,061 B1 | 3/2001 | Masuda et al. | |
| 6,197,586 B1 | 3/2001 | Bhatnagar et al. | |
| 6,200,347 B1 | 3/2001 | Anderson et al. | |
| 6,221,854 B1 | 4/2001 | Radomsky | |
| 6,231,607 B1 | 5/2001 | Ben-Bassat et al. | |
| 6,235,316 B1 | 5/2001 | Adkisson | |
| 6,242,247 B1 | 6/2001 | Rieser et al. | |
| 6,251,143 B1 | 6/2001 | Schwartz et al. | |
| 6,258,778 B1 | 7/2001 | Rodgers et al. | |
| 6,261,586 B1 | 7/2001 | McKay | |
| 6,267,786 B1 | 7/2001 | Stone | |
| 6,270,528 B1 | 8/2001 | McKay | |
| 6,274,090 B1 | 8/2001 | Coelho et al. | |
| 6,274,663 B1 | 8/2001 | Hosokawa et al. | |
| 6,274,712 B1 | 8/2001 | Springer et al. | |
| 6,280,473 B1 | 8/2001 | Lemperle et al. | |
| 6,281,195 B1 | 8/2001 | Rueger et al. | |
| 6,283,980 B1 | 9/2001 | Vibe-Hansen et al. | |
| 6,288,043 B1 | 9/2001 | Spiro et al. | |
| 6,293,970 B1 | 9/2001 | Wolfinbarger, Jr. | |
| 6,294,187 B1 | 9/2001 | Boyce et al. | |
| 6,294,359 B1 | 9/2001 | Fiddes et al. | |
| 6,303,585 B1 | 10/2001 | Spiro et al. | |
| 6,305,379 B1 | 10/2001 | Wolfinbarger, Jr. | |
| 6,306,174 B1 | 10/2001 | Gei et al. | |
| 6,306,177 B1 | 10/2001 | Felt et al. | |
| 6,306,424 B1 | 10/2001 | Vyakarnam et al. | |
| 6,310,267 B1 | 10/2001 | Rapp | |
| 6,319,712 B1 | 11/2001 | Meenen et al. | |
| 6,333,029 B1 | 12/2001 | Vyakanam et al. | |
| 6,352,558 B1 | 3/2002 | Spector | |
| 6,352,971 B1 | 3/2002 | Diesher et al. | |
| 6,361,565 B1 | 3/2002 | Bonutti | |
| 6,371,958 B1 | 4/2002 | Overaker | |
| 6,376,244 B1 | 4/2002 | Atala | |
| 6,379,367 B1 | 4/2002 | Vibe-Hansen et al. | |
| 6,379,385 B1 | 4/2002 | Kalas et al. | |
| 6,383,221 B1 | 5/2002 | Scarborough et al. | |
| 6,387,693 B2 | 5/2002 | Rieser et al. | |
| 6,398,811 B1 | 6/2002 | McKay | |
| 6,398,816 B1 | 6/2002 | Breitbart et al. | |
| 6,398,972 B1 | 6/2002 | Blasetti et al. | |
| 6,432,436 B1 | 8/2002 | Gertzman et al. | |
| 6,437,018 B1 | 8/2002 | Gertzman et al. | |
| 6,440,141 B1 | 8/2002 | Philippon | |
| 6,440,427 B1 | 8/2002 | Wadstrom | |
| 6,440,444 B2 | 8/2002 | Boyce et al. | |
| 6,451,060 B2 | 9/2002 | Masuda et al. | |
| 6,454,811 B1 | 9/2002 | Sherwood et al. | |
| 6,458,144 B1 | 10/2002 | Morris et al. | |
| 6,458,158 B1 | 10/2002 | Anderson et al. | |
| 6,458,375 B1 | 10/2002 | Gertzman et al. | |
| 6,468,314 B2 | 10/2002 | Schwartz et al. | |
| 6,471,993 B1 | 10/2002 | Shastri et al. | |
| 6,475,175 B1 | 11/2002 | Rivera et al. | |
| 6,486,377 B2 | 11/2002 | Rapp | |
| 6,488,033 B1 | 12/2002 | Cerundolo | |
| 6,489,165 B2 | 12/2002 | Bhatnagar et al. | |
| 6,497,726 B1 | 12/2002 | Carter et al. | |
| 6,503,277 B2 | 1/2003 | Bonutti | |
| 6,504,079 B2 | 1/2003 | Tucker et al. | |
| 6,511,511 B1 | 1/2003 | Slivka et al. | |
| 6,511,958 B1 | 1/2003 | Atkinson et al. | |
| 6,514,514 B1 | 2/2003 | Atkinson et al. | |
| 6,520,964 B2 | 2/2003 | Tallarida et al. | |
| 6,530,956 B1 | 3/2003 | Mansmann | |
| 6,534,084 B1 | 3/2003 | Vyakarnam et al. | |
| 6,541,024 B1 | 4/2003 | Kadiyala et al. | |
| 6,548,729 B1 | 4/2003 | Seelich et al. | |
| 6,569,172 B2 | 5/2003 | Asculai et al. | |
| 6,576,015 B2 | 6/2003 | Geistlich et al. | |
| 6,576,265 B1 | 6/2003 | Spievack | |
| 6,579,538 B1 | 6/2003 | Spievack | |
| 6,582,960 B1 | 6/2003 | Martin et al. | |
| 6,591,581 B2 | 7/2003 | Schmieding | |
| 6,592,598 B2 | 7/2003 | Vibe-Hansen et al. | |
| 6,592,599 B2 | 7/2003 | Vibe-Hansen et al. | |
| 6,599,300 B2 | 7/2003 | Vibe-Hansen et al. | |
| 6,599,301 B2 | 7/2003 | Vibe-Hansen et al. | |
| 6,599,515 B1 | 7/2003 | Delmotte | |
| 6,623,963 B1 | 9/2003 | Muller et al. | |
| 6,626,950 B2 | 9/2003 | Brown et al. | |
| 6,630,000 B1 | 10/2003 | Bonutti | |
| 6,632,247 B2 | 10/2003 | Boyer, II et al. | |
| 6,652,592 B1 | 11/2003 | Grooms et al. | |
| 6,652,593 B2 | 11/2003 | Boyer, II et al. | |
| 6,652,872 B2 | 11/2003 | Nevo et al. | |
| 6,662,805 B2 | 12/2003 | Frondoza et al. | |
| 6,666,892 B2 | 12/2003 | Hiles et al. | |
| 6,686,184 B1 | 2/2004 | Anderson et al. | |
| 6,689,747 B2 | 2/2004 | Filvaroff et al. | |
| 6,696,073 B2 | 2/2004 | Boyce et al. | |
| 6,712,851 B1 | 3/2004 | Lemperle et al. | |
| 6,727,224 B1 | 4/2004 | Zhang et al. | |
| RE38,522 E | 5/2004 | Gertzman et al. | |
| 6,730,314 B2 | 5/2004 | Jeschke et al. | |
| 6,734,018 B2 | 5/2004 | Wolfinbarger, Jr. et al. | |
| 6,743,232 B2 | 6/2004 | Overaker et al. | |
| 6,752,834 B2 | 6/2004 | Geistlich et al. | |
| 6,761,739 B2 | 7/2004 | Shepard | |
| 6,761,887 B1 | 7/2004 | Kavalkovich et al. | |
| 6,767,369 B2 | 7/2004 | Boyer et al. | |
| 6,776,800 B2 | 8/2004 | Boyer, II et al. | |

| | | |
|---|---|---|
| 6,783,712 B2 | 8/2004 | Slivka et al. |
| 6,808,585 B2 | 10/2004 | Boyce et al. |
| 6,815,416 B2 | 11/2004 | Carney et al. |
| 6,838,440 B2 | 1/2005 | Stiles |
| 6,841,150 B2 | 1/2005 | Halvorsen et al. |
| 6,849,255 B2 | 2/2005 | Gazit et al. |
| 6,852,114 B2 | 2/2005 | Cerundolo |
| 6,852,125 B2 | 2/2005 | Simon et al. |
| 6,852,331 B2 | 2/2005 | Lai et al. |
| 6,855,167 B2 | 2/2005 | Shimp et al. |
| 6,855,169 B2 | 2/2005 | Boyer, II et al. |
| 6,858,042 B2 | 2/2005 | Nadler et al. |
| 6,866,668 B2 | 3/2005 | Giannetti et al. |
| 6,884,428 B2 | 4/2005 | Binette et al. |
| 6,890,354 B2 | 5/2005 | Steiner et al. |
| 6,893,462 B2 | 5/2005 | Buskirk et al. |
| 6,902,578 B1 | 6/2005 | Anderson et al. |
| 6,911,212 B2 | 6/2005 | Gertzman et al. |
| 6,932,977 B2 | 8/2005 | Heidaran et al. |
| 6,933,326 B1 | 8/2005 | Griffey et al. |
| 6,933,328 B2 | 8/2005 | Schacht |
| 6,949,252 B2 | 9/2005 | Mizuno et al. |
| 6,989,034 B2 | 1/2006 | Hammer et al. |
| 6,995,013 B2 | 2/2006 | Connelly et al. |
| 7,009,039 B2 | 3/2006 | Yayon et al. |
| 7,018,416 B2 | 3/2006 | Hanson et al. |
| 7,033,587 B2 | 4/2006 | Halvorsen et al. |
| 7,041,641 B2 | 5/2006 | Rueger et al. |
| 7,044,968 B1 | 5/2006 | Yaccarino, III et al. |
| 7,045,141 B2 | 5/2006 | Merboth et al. |
| 7,048,750 B2 | 5/2006 | Vibe-Hansen et al. |
| 7,048,762 B1 | 5/2006 | Sander et al. |
| 7,048,765 B1 | 5/2006 | Grooms et al. |
| 7,067,123 B2 | 6/2006 | Gomes et al. |
| 7,070,942 B2 | 7/2006 | Heidaran et al. |
| 7,078,232 B2 | 7/2006 | Konkle et al. |
| 7,087,082 B2 | 8/2006 | Paul et al. |
| 7,087,227 B2 | 8/2006 | Adkisson |
| 7,108,721 B2 | 9/2006 | Huckle et al. |
| RE39,321 E | 10/2006 | MacPhee et al. |
| 7,115,146 B2 | 10/2006 | Boyer, II et al. |
| 7,125,423 B2 | 10/2006 | Hazebrouck |
| 7,132,110 B2 | 11/2006 | Kay et al. |
| 7,137,989 B2 | 11/2006 | Asculai et al. |
| 7,141,072 B2 | 11/2006 | Coeistlich |
| 7,156,880 B2 | 1/2007 | Evans et al. |
| 7,157,428 B2 | 1/2007 | Kusanagi et al. |
| 7,163,563 B2 | 1/2007 | Schwartz et al. |
| 7,166,133 B2 | 1/2007 | Evans et al. |
| 7,179,299 B2 | 2/2007 | Edwards et al. |
| 7,182,781 B1 | 2/2007 | Bianchi et al. |
| RE39,587 E | 4/2007 | Gertzman et al. |
| 7,201,917 B2 | 4/2007 | Malaviya et al. |
| 7,217,294 B2 | 5/2007 | Kusanagi et al. |
| 7,220,558 B2 | 5/2007 | Luyten et al. |
| 7,226,482 B2 | 6/2007 | Messerli et al. |
| 7,241,316 B2 | 7/2007 | Evans et al. |
| 7,252,987 B2 | 8/2007 | Bachalo et al. |
| 7,264,634 B2 | 9/2007 | Schmieding |
| 7,273,756 B2 | 9/2007 | Adkisson et al. |
| 7,288,406 B2 | 10/2007 | Bogin et al. |
| 7,291,169 B2 | 11/2007 | Hodorek |
| 7,297,161 B2 | 11/2007 | Fell |
| 7,316,822 B2 | 1/2008 | Binette et al. |
| 7,323,011 B2 | 1/2008 | Shepard et al. |
| 7,323,445 B2 | 1/2008 | Zhang et al. |
| 7,335,508 B2 | 2/2008 | Yayon et al. |
| 7,338,492 B2 | 3/2008 | Singhatat |
| 7,338,524 B2 | 3/2008 | Fell et al. |
| 7,358,284 B2 | 4/2008 | Griffey et al. |
| 7,361,195 B2 | 4/2008 | Schwartz et al. |
| 7,365,051 B2 | 4/2008 | Paulista et al. |
| 7,371,400 B2 | 5/2008 | Borenstein et al. |
| 7,416,889 B2 | 8/2008 | Ciombor et al. |
| 7,468,075 B2 | 12/2008 | Lang et al. |
| 7,468,192 B2 | 12/2008 | Mizuno et al. |
| 7,476,257 B2 | 1/2009 | Sah et al. |
| 7,479,160 B2 | 1/2009 | Branch et al. |
| 7,485,310 B2 | 2/2009 | Luyten et al. |
| 7,488,348 B2 | 2/2009 | Truncale et al. |
| 7,513,910 B2 | 4/2009 | Buskirk et al. |
| 7,531,000 B2 | 5/2009 | Hodorek |
| 7,537,617 B2 | 5/2009 | Bindsell et al. |
| 7,537,780 B2 | 5/2009 | Mizuno et al. |
| 7,548,865 B2 | 6/2009 | Schmieding |
| 7,550,007 B2 | 6/2009 | Malinin |
| 7,563,455 B2 | 7/2009 | McKay |
| 7,563,769 B2 | 7/2009 | Bogin et al. |
| 7,601,173 B2 | 10/2009 | Messerli et al. |
| 7,608,113 B2 | 10/2009 | Boyer, II et al. |
| 7,621,963 B2 | 11/2009 | Simon et al. |
| 7,622,438 B1 | 11/2009 | Lazarov et al. |
| 7,622,562 B2 | 11/2009 | Thorne et al. |
| 7,628,851 B2 | 12/2009 | Armitage et al. |
| 7,632,311 B2 | 12/2009 | Seedhom et al. |
| 7,638,486 B2 | 12/2009 | Lazarov et al. |
| 7,642,092 B2 | 1/2010 | Maor |
| 7,648,700 B2 | 1/2010 | Vignery et al. |
| 7,648,965 B2 | 1/2010 | Vignery et al. |
| 7,658,768 B2 | 2/2010 | Miller et al. |
| 7,662,184 B2 | 2/2010 | Edwards et al. |
| 7,666,230 B2 | 2/2010 | Orban et al. |
| RE41,286 E | 4/2010 | Atkinson et al. |
| 7,815,926 B2 | 10/2010 | Syring et al. |
| 7,824,701 B2 | 11/2010 | Binette et al. |
| 7,837,740 B2 | 11/2010 | Semler et al. |
| 7,875,296 B2 | 1/2011 | Binette et al. |
| RE42,208 E | 3/2011 | Truncale et al. |
| 7,901,457 B2 | 3/2011 | Truncale et al. |
| 7,901,461 B2 | 3/2011 | Harmon et al. |
| 2001/0005592 A1 | 6/2001 | Bhatnager et al. |
| 2001/0006634 A1 | 7/2001 | Zaleske et al. |
| 2001/0010023 A1 | 7/2001 | Schwartz et al. |
| 2001/0011131 A1 | 8/2001 | Luyten et al. |
| 2001/0016646 A1 | 8/2001 | Rueger et al. |
| 2001/0018619 A1 | 8/2001 | Enzerink et al. |
| 2001/0020188 A1 | 9/2001 | Sander |
| 2001/0021875 A1 | 9/2001 | Enzerink et al. |
| 2001/0031254 A1 | 10/2001 | Bianchi et al. |
| 2001/0039457 A1 | 11/2001 | Boyer, II et al. |
| 2001/0039458 A1 | 11/2001 | Boyer, II et al. |
| 2001/0041941 A1 | 11/2001 | Boyer, II et al. |
| 2001/0043940 A1 | 11/2001 | Boyce et al. |
| 2001/0051834 A1 | 12/2001 | Frondoza et al. |
| 2002/0009805 A1 | 1/2002 | Nevo et al. |
| 2002/0016592 A1 | 2/2002 | Branch et al. |
| 2002/0035401 A1 | 3/2002 | Boyce et al. |
| 2002/0042373 A1 | 4/2002 | Carney et al. |
| 2002/0045940 A1 | 4/2002 | Giannetti et al. |
| 2002/0055783 A1 | 5/2002 | Tallarida et al. |
| 2002/0072806 A1 | 6/2002 | Buskirk et al. |
| 2002/0082704 A1 | 6/2002 | Cerundolo |
| 2002/0099448 A1 | 7/2002 | Hiles et al. |
| 2002/0106393 A1 | 8/2002 | Bianchi et al. |
| 2002/0111695 A1 | 8/2002 | Kandel |
| 2002/0120274 A1 | 8/2002 | Overaker et al. |
| 2002/0138143 A1 | 9/2002 | Grooms et al. |
| 2002/0177224 A1 | 11/2002 | Madry et al. |
| 2002/0192263 A1 | 12/2002 | Merboth et al. |
| 2003/0021827 A1 | 1/2003 | Malaviya et al. |
| 2003/0023316 A1 | 1/2003 | Brown et al. |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0039695 A1 | 2/2003 | Geistlich et al. |
| 2003/0040113 A1 | 2/2003 | Muzuno et al. |
| 2003/0044444 A1 | 3/2003 | Malaviya et al. |
| 2003/0049299 A1 | 3/2003 | Malaviya et al. |
| 2003/0050709 A1 | 3/2003 | Noth et al. |
| 2003/0055502 A1 | 3/2003 | Lang et al. |
| 2003/0077821 A1 | 4/2003 | Sah et al. |
| 2003/0078617 A1 | 4/2003 | Schwartz et al. |
| 2003/0099620 A1 | 5/2003 | Zaleske et al. |
| 2003/0139591 A1 | 7/2003 | Luyten et al. |
| 2003/0144743 A1 | 7/2003 | Edwards et al. |
| 2003/0229400 A1 | 12/2003 | Masuda et al. |

| Pub. No. | Date | Name |
|---|---|---|
| 2003/0236573 A1 | 12/2003 | Evans et al. |
| 2004/0024457 A1 | 2/2004 | Boyce et al. |
| 2004/0028717 A1 | 2/2004 | Sittinger et al. |
| 2004/0033212 A1 | 2/2004 | Thomson et al. |
| 2004/0039447 A1 | 2/2004 | Simon et al. |
| 2004/0044408 A1 | 3/2004 | Hungerford et al. |
| 2004/0062753 A1 | 4/2004 | Rezania et al. |
| 2004/0078078 A1* | 4/2004 | Shepard ............... 623/17.11 |
| 2004/0078090 A1 | 4/2004 | Binette et al. |
| 2004/0102850 A1 | 5/2004 | Shepard |
| 2004/0107003 A1 | 6/2004 | Boyer, II et al. |
| 2004/0115172 A1 | 6/2004 | Bianchi et al. |
| 2004/0127987 A1 | 7/2004 | Evans et al. |
| 2004/0134502 A1 | 7/2004 | Mizuno et al. |
| 2004/0138748 A1* | 7/2004 | Boyer et al. ............. 623/16.11 |
| 2004/0143344 A1 | 7/2004 | Malaviya et al. |
| 2004/0151705 A1 | 8/2004 | Mizuno et al. |
| 2004/0166169 A1 | 8/2004 | Malaviya et al. |
| 2004/0170610 A1 | 9/2004 | Slavin et al. |
| 2004/0175826 A1 | 9/2004 | Maor |
| 2004/0192605 A1 | 9/2004 | Zhang et al. |
| 2004/0193268 A1 | 9/2004 | Hazebrouck |
| 2004/0197311 A1 | 10/2004 | Brekke et al. |
| 2004/0197373 A1 | 10/2004 | Gertzman et al. |
| 2004/0219182 A1 | 11/2004 | Gomes et al. |
| 2004/0220574 A1 | 11/2004 | Pelo et al. |
| 2004/0230303 A1* | 11/2004 | Gomes et al. ............. 623/16.11 |
| 2004/0241203 A1 | 12/2004 | Shakesheff et al. |
| 2004/0243242 A1 | 12/2004 | Sybert et al. |
| 2005/0004672 A1 | 1/2005 | Pafford et al. |
| 2005/0020500 A1 | 1/2005 | Shen et al. |
| 2005/0027307 A1 | 2/2005 | Schwartz et al. |
| 2005/0043814 A1 | 2/2005 | Kusanagi et al. |
| 2005/0064042 A1 | 3/2005 | Vunjak-Novakovic et al. |
| 2005/0074476 A1 | 4/2005 | Gendler et al. |
| 2005/0074481 A1 | 4/2005 | Brekke et al. |
| 2005/0089544 A1 | 4/2005 | Khouri et al. |
| 2005/0101957 A1 | 5/2005 | Buskirk et al. |
| 2005/0112761 A1 | 5/2005 | Halvorsen et al. |
| 2005/0125077 A1 | 6/2005 | Harmon et al. |
| 2005/0129668 A1 | 6/2005 | Giannetti et al. |
| 2005/0152882 A1 | 7/2005 | Kizer et al. |
| 2005/0159820 A1 | 7/2005 | Yoshikawa et al. |
| 2005/0159822 A1 | 7/2005 | Griffey et al. |
| 2005/0196460 A1 | 9/2005 | Malinin |
| 2005/0209705 A1 | 9/2005 | Niederauer et al. |
| 2005/0222687 A1* | 10/2005 | Vunjak-Novakovic et al. ............. 623/23.63 |
| 2005/0228498 A1 | 10/2005 | Andres |
| 2005/0240281 A1 | 10/2005 | Slivka et al. |
| 2005/0251268 A1 | 11/2005 | Truncale |
| 2005/0260612 A1 | 11/2005 | Padmini et al. |
| 2005/0261681 A9 | 11/2005 | Branch et al. |
| 2005/0261767 A1 | 11/2005 | Anderson et al. |
| 2005/0288796 A1 | 12/2005 | Awad et al. |
| 2006/0030948 A1 | 2/2006 | Manrique et al. |
| 2006/0060209 A1 | 3/2006 | Shepard |
| 2006/0099234 A1 | 5/2006 | Winkler |
| 2006/0111778 A1 | 5/2006 | Michalow |
| 2006/0167483 A1 | 7/2006 | Asculai et al. |
| 2006/0178748 A1 | 8/2006 | Dinger, III et al. |
| 2006/0200166 A1 | 9/2006 | Hanson et al. |
| 2006/0210643 A1 | 9/2006 | Truncale et al. |
| 2006/0216323 A1 | 9/2006 | Knaack et al. |
| 2006/0216822 A1 | 9/2006 | Mizuno et al. |
| 2006/0235534 A1 | 10/2006 | Gertzman et al. |
| 2006/0247790 A1 | 11/2006 | McKay |
| 2006/0247791 A1 | 11/2006 | McKay et al. |
| 2006/0251631 A1 | 11/2006 | Adkisson, IV et al. |
| 2006/0276907 A1 | 12/2006 | Boyer, II et al. |
| 2006/0293757 A1 | 12/2006 | McKay et al. |
| 2007/0009610 A1 | 1/2007 | Syring |
| 2007/0014867 A1 | 1/2007 | Kusanagi et al. |
| 2007/0026030 A1 | 2/2007 | Gill et al. |
| 2007/0036834 A1 | 2/2007 | Pauletti et al. |
| 2007/0041950 A1 | 2/2007 | Leatherbury et al. |
| 2007/0055377 A1 | 3/2007 | Hanson et al. |
| 2007/0065943 A1 | 3/2007 | Smith et al. |
| 2007/0067032 A1 | 3/2007 | Felt et al. |
| 2007/0083266 A1 | 4/2007 | Lang |
| 2007/0093896 A1 | 4/2007 | Malinin |
| 2007/0093912 A1 | 4/2007 | Borden |
| 2007/0098759 A1 | 5/2007 | Malinin |
| 2007/0100450 A1 | 5/2007 | Hodorek |
| 2007/0113951 A1 | 5/2007 | Huang |
| 2007/0128155 A1 | 6/2007 | Sevedin |
| 2007/0134291 A1 | 6/2007 | Ting |
| 2007/0135917 A1 | 6/2007 | Malinin |
| 2007/0135918 A1 | 6/2007 | Malinin |
| 2007/0135928 A1 | 6/2007 | Malinin |
| 2007/0148242 A1 | 6/2007 | Vilei et al. |
| 2007/0162121 A1 | 7/2007 | Tarrant et al. |
| 2007/0168030 A1 | 7/2007 | Edwards et al. |
| 2007/0172506 A1 | 7/2007 | Nycz et al. |
| 2007/0179607 A1 | 8/2007 | Hodorek et al. |
| 2007/0185585 A1 | 8/2007 | Bracy et al. |
| 2007/0276506 A1 | 11/2007 | Troxel |
| 2007/0299517 A1 | 12/2007 | Davisson et al. |
| 2007/0299519 A1 | 12/2007 | Schmieding |
| 2008/0015709 A1 | 1/2008 | Evans et al. |
| 2008/0027546 A1 | 1/2008 | Semler et al. |
| 2008/0031915 A1 | 2/2008 | Ratia et al. |
| 2008/0038314 A1 | 2/2008 | Hunziker |
| 2008/0039939 A1 | 2/2008 | Iwamoto et al. |
| 2008/0039954 A1 | 2/2008 | Long et al. |
| 2008/0039955 A1 | 2/2008 | Hunziker |
| 2008/0051889 A1 | 2/2008 | Hodorek |
| 2008/0058953 A1 | 3/2008 | Scarborough |
| 2008/0065210 A1 | 3/2008 | McKay |
| 2008/0077251 A1 | 3/2008 | Chen et al. |
| 2008/0119947 A1 | 5/2008 | Huckle et al. |
| 2008/0125863 A1 | 5/2008 | McKay |
| 2008/0125868 A1 | 5/2008 | Branemark |
| 2008/0133008 A1 | 6/2008 | Truncale et al. |
| 2008/0138414 A1 | 6/2008 | Hunckle et al. |
| 2008/0153157 A1 | 6/2008 | Yao et al. |
| 2008/0154372 A1 | 6/2008 | Peckham |
| 2008/0167716 A1 | 7/2008 | Schwartz et al. |
| 2008/0183300 A1 | 7/2008 | Seedhom et al. |
| 2008/0220044 A1 | 9/2008 | Semler et al. |
| 2008/0249632 A1 | 10/2008 | Stone et al. |
| 2008/0255676 A1 | 10/2008 | Semler et al. |
| 2008/0274157 A1 | 11/2008 | Vunjak-Novakovic et al. |
| 2008/0294270 A1 | 11/2008 | Yao et al. |
| 2008/0305145 A1 | 12/2008 | Shelby et al. |
| 2009/0024224 A1 | 1/2009 | Chen et al. |
| 2009/0043389 A1 | 2/2009 | Vunjak-Novakovic et al. |
| 2009/0069901 A1 | 3/2009 | Truncale et al. |
| 2009/0069904 A1 | 3/2009 | Picha |
| 2009/0076624 A1 | 3/2009 | Rahaman et al. |
| 2009/0081276 A1 | 3/2009 | Alsby et al. |
| 2009/0099661 A1 | 4/2009 | Bhattacharya et al. |
| 2009/0117652 A1 | 5/2009 | Luyten et al. |
| 2009/0131986 A1 | 5/2009 | Lee et al. |
| 2009/0149893 A1 | 6/2009 | Semler et al. |
| 2009/0210057 A1 | 8/2009 | Liao et al. |
| 2009/0226523 A1 | 9/2009 | Behnam et al. |
| 2009/0248592 A1 | 10/2009 | Schmieding |
| 2009/0280179 A1 | 11/2009 | Neumann et al. |
| 2009/0291112 A1 | 11/2009 | Truncale et al. |
| 2009/0299475 A1 | 12/2009 | Yamamoto et al. |
| 2009/0312805 A1 | 12/2009 | Lang et al. |
| 2009/0312842 A1 | 12/2009 | Bursac et al. |
| 2009/0319045 A1 | 12/2009 | Truncale et al. |
| 2009/0319051 A9 | 12/2009 | Nycz et al. |
| 2009/0324722 A1 | 12/2009 | Elisseeff |
| 2010/0015202 A1 | 1/2010 | Semler et al. |
| 2010/0021521 A1 | 1/2010 | Xu et al. |
| 2010/0036492 A1 | 2/2010 | Hung et al. |
| 2010/0036503 A1 | 2/2010 | Chen et al. |
| 2010/0241228 A1 | 9/2010 | Syring et al. |
| 2010/0274362 A1 | 10/2010 | Yayon et al. |
| 2010/0322994 A1 | 12/2010 | Kizer et al. |
| 2011/0052705 A1 | 3/2011 | Malinin |
| 2011/0070271 A1 | 3/2011 | Truncele et al. |
| 2011/0104242 A1 | 5/2011 | Malinin |
| 2012/0009224 A1 | 1/2012 | Kizer et al. |
| 2012/0009270 A1 | 1/2012 | Kizer et al. |

FOREIGN PATENT DOCUMENTS

| | | |
|---|---|---|
| EP | 0522569 A1 | 1/1993 |
| EP | 0762903 A1 | 12/1995 |
| EP | 0517030 B1 | 9/1996 |
| EP | 0739631 A2 | 10/1996 |
| EP | 0784985 A1 | 7/1997 |
| EP | 0968012 A1 | 9/1998 |
| EP | 1237511 A1 | 6/2001 |
| EP | 1127581 A1 | 8/2001 |
| EP | 1181908 A1 | 2/2002 |
| EP | 1234552 A1 | 8/2002 |
| EP | 1234555 A2 | 8/2002 |
| EP | 0762903 B1 | 9/2003 |
| EP | 0739631 B1 | 12/2003 |
| EP | 1181908 B1 | 12/2003 |
| EP | 1384452 A1 | 1/2004 |
| EP | 1234555 A3 | 6/2004 |
| EP | 1237511 B1 | 9/2004 |
| EP | 1618178 A1 | 11/2004 |
| EP | 1127581 B1 | 6/2005 |
| EP | 1561481 A2 | 8/2005 |
| EP | 1234552 B1 | 8/2006 |
| EP | 0968012 B1 | 9/2006 |
| EP | 1719463 A1 | 11/2006 |
| EP | 1719531 A2 | 11/2006 |
| EP | 1719532 A2 | 11/2006 |
| EP | 1234555 B1 | 2/2007 |
| EP | 0762903 B2 | 8/2007 |
| EP | 1740121 A2 | 10/2007 |
| EP | 1537883 B1 | 4/2008 |
| EP | 1618178 B1 | 7/2008 |
| EP | 1416880 B1 | 2/2011 |
| GB | 2102811 A1 | 2/1983 |
| SU | 1454423 A1 | 1/1989 |
| WO | 84/04880 A1 | 12/1984 |
| WO | 90/01342 A1 | 2/1990 |
| WO | 93/16739 A1 | 9/1993 |
| WO | 94/03584 A1 | 2/1994 |
| WO | 95/25748 A1 | 9/1995 |
| WO | 95/33502 A1 | 12/1995 |
| WO | 96/24310 A1 | 8/1996 |
| WO | 97/37613 A1 | 10/1997 |
| WO | 98/14222 A1 | 4/1998 |
| WO | 98/34569 A1 | 8/1998 |
| WO | 98/41246 A2 | 9/1998 |
| WO | 98/43686 A1 | 10/1998 |
| WO | 99/08728 A1 | 2/1999 |
| WO | 99/09914 A1 | 3/1999 |
| WO | 99/11298 A2 | 3/1999 |
| WO | 99/15209 A1 | 4/1999 |
| WO | 99/21497 A1 | 5/1999 |
| WO | 99/22747 A1 | 5/1999 |
| WO | 99/48541 A1 | 9/1999 |
| WO | 99/52572 A1 | 10/1999 |
| WO | 99/56797 A1 | 11/1999 |
| WO | 00/40177 A1 | 7/2000 |
| WO | 00/47114 A1 | 8/2000 |
| WO | 00/72782 A1 | 12/2000 |
| WO | 01/07595 A2 | 2/2001 |
| WO | 01/38357 A2 | 5/2001 |
| WO | 01/39788 A2 | 6/2001 |
| WO | 01/43667 A1 | 6/2001 |
| WO | 01/46416 A1 | 6/2001 |
| WO | 02/18546 A2 | 3/2002 |
| WO | 02/22779 A2 | 3/2002 |
| WO | 02/36732 A2 | 5/2002 |
| WO | 02/058484 A2 | 8/2002 |
| WO | 02/064180 A1 | 8/2002 |
| WO | 02/077199 A2 | 10/2002 |
| WO | 02/095019 A1 | 11/2002 |
| WO | 03/007805 A2 | 1/2003 |
| WO | 03/007873 A2 | 1/2003 |
| WO | 03/007879 A2 | 1/2003 |
| WO | 03/012053 A2 | 2/2003 |
| WO | 03/007879 A3 | 8/2003 |
| WO | 03/079985 A2 | 10/2003 |
| WO | 03/087160 A1 | 10/2003 |
| WO | 03/094835 A2 | 11/2003 |
| WO | 03/007805 A3 | 2/2004 |
| WO | 2004/067704 A2 | 8/2004 |
| WO | 2004/069298 A1 | 8/2004 |
| WO | 2004/075940 A1 | 9/2004 |
| WO | 2004/096983 A2 | 11/2004 |
| WO | 2004/103224 A1 | 12/2004 |
| WO | 2005058207 A1 | 6/2005 |
| WO | 2005/110278 A2 | 11/2005 |
| WO | 2004/096983 A3 | 12/2005 |
| WO | 2006/036681 A2 | 4/2006 |
| WO | 2006/042311 A2 | 4/2006 |
| WO | 2006/050213 A2 | 5/2006 |
| WO | 2005/110278 A3 | 8/2006 |
| WO | 02/036732 A3 | 9/2006 |
| WO | 2006/113586 A2 | 10/2006 |
| WO | 2006/042311 A3 | 11/2006 |
| WO | 03/094835 A3 | 12/2006 |
| WO | 2007/024238 A1 | 3/2007 |
| WO | 2006/113586 A3 | 7/2007 |
| WO | 2008/013763 A2 | 1/2008 |
| WO | 2008/021127 A2 | 2/2008 |
| WO | 2008/013763 A3 | 4/2008 |
| WO | 2008/038287 A2 | 4/2008 |
| WO | 2008/081463 A2 | 7/2008 |
| WO | 2008/106254 A2 | 9/2008 |
| WO | 2008/038287 A3 | 4/2009 |
| WO | 2009/076164 A2 | 6/2009 |
| WO | 2009/111069 A1 | 9/2009 |
| WO | 2009/155232 A1 | 12/2009 |
| WO | 2010/083051 A2 | 7/2010 |

OTHER PUBLICATIONS

Final Office Action for U.S. Appl. No. 12/381,072, mailed Jun. 27, 2011.

Non-final Office Action for U.S. Appl. No. 12/966,674, mailed Jul. 12, 2011.

Non-final Office Action for U.S. Appl. No. 12/924,132, mailed Jul. 18, 2011.

Cheng, et al., "Chondrogenic Differentiation of Adipose-Derived Adult Stem Cells by a Porous Scaffold Derived from Native Articular Cartilage Extracellular Matrix", Tissue Engineering: Part A, vol. 15, No. 2, (2009), pp. 231-241.

Lin et al., "The Chondrocyte: Biology and Clinical Application", Tissue Engineering, vol. 12, No. 7, (2006), pp. 1971-1984.

Umlauf et al., "Cartilage biology, pathology, and repair", Cell. Mol. Life Sci., vol. 67, (2010), pp. 4197-4211.

Peretti et al., "In Vitro Bonding of Pre-seeded Chondrocyte", Sport Sciences for Health, May 1, 2007, vol. 2, No. 1, pp. 29-33.

Peretti et al., "Bonding of Cartilage Matrices with Cultured Chondrocytes: An Experiential Model", Journal of Orthopedic Research, Jan. 1998, vol. 16, No. 1, pp. 89-95.

Hunziker, "Articular Cartilage Repair: Basic Science and Clinical Progress. A Review of the Current Status and Prospects", Osteoarthritis and Cartilage 2001, vol. 10, No. 6, pp. 432-463.

Chen et al., "Repair of Articular Cartilage Defects: Part I. Basic Science of Cartilage Healing", The American Journal of Orthopedics, Jan. 1999, pp. 31-33.

Chen et al., "Repair of Articular Cartilage Defects: Part II. Treatment Options", The American Journal of Orthopedics, Feb. 1999, pp. 88-96.

Buckwalter, "Articular Cartilage Injuries", Clinical Orthopaedics and Related Research, 2002, No. 402, pp. 21-37.

Nixon et al., "New Horizons in Articular Cartilage Repair", Proceedings of the Annual Convention of the AAEP, 2001, vol. 47, pp. 217-226.

Tsumaki et al. "Role of CDMP-1 in Skeletal Morphogenesis: Promotion of Mesenchymal Cell Recruitment and Chondrocyte Differentiation", J. Cell Biol., Jan. 1999, vol. 144, No. 1, 161-173.

Trzeciak et al., "Evaluation of Cartilage Reconstruction by Means of Autologous Chondrocyte Versus Periosteal Graft Transplantation: An Animal Study", Transplantation Proceedings, vol. 38 (2006), pp. 305-311.

Brighton et al., "Articular Cartilage Preservation and Storage—I. Application of Tissue Culture Techniques to the Storage of Viable Articular Cartilage", Arthritis and Rheumatism, vol. 22, No. 10 (Oct. 1979), pp. 1093-1101.

Mahadev et al., "Autogenous Osteochondral Morselised Grafts for Full Thickness Osteochondral Defects in the Knee Joints of Pigs", Singapore Medical Journal, 2001, vol. 42(9), pp. 410-416.
Hunziker, "Articular Cartilage Structure in Humans and Experimental Animals", Articular Cartilage and Osteoarthritis, Raven Press, ed., 2001, pp. 183-199.
Girotto et al., "Tissue-specific gene expression in chondrocytes grown on three-dimensional hyaluronic acid scaffolds", Biomaterials, vol. 24 (2003), pp. 3265-3275.
Gertzman et al., "A pilot study evaluating sodium hyaluronate as a carrier for freeze-dried demineralized bone powder", Cell and Tissue Banking, vol. 2, 2001, pp. 87-94.
Diduch et al., "Joint Repair: Treatment Options for Articular Cartilage Injury" Orthopedic Technology Review (2002) 4:24-27.
Gilbert, et al., "Decellularization of Tissues and Organs", Biomaterials (2006) 27:3675-3683.
OsteoSponge product information, Bacterin International Inc., May 2005.
http://www.stoneclinic.com/articularcartilagepastegrafting (Copyright 2009).
http://www.technobusiness-solutions.com/article-lyophilization1.html (published Feb. 12, 2002).
Crescenzi et al., "Hyaluron Linear and Crosslinked Derivatives as Potential/Actual Biomaterials", in Hyaluronan (2002), vol. 1 (Chemical, Biochemical and Biological Aspects), J. F. Kennedy et al., Ed., pp. 261-268.
Michielen et al., "Novel Biomaterials Based on Cross-linked Hyaluronon: Structural Investigations", in Hyaluronan (2002), vol. 1 (Chemical, Biochemical and Biological Aspects), J. F. Kennedy et al., Ed., pp. 269-276.
U.S. Appl. No. 12/147,042, based on U.S. Patent No. 7,067,123, filed Jun. 26, 2008, entitled: "Novel Glue for Cartilage Repair".
Non-final Office Action mailed Aug. 19, 2009 in connection with U.S. Appl. No. 12/147,042.
Non-final Office Action mailed Apr. 19, 2007 in connection with U.S. Appl. No. 11/151,270.
Final Office Action mailed Oct. 9, 2007 in connection with U.S. Appl. No. 11/151,270.
Advisory Action mailed Dec. 27, 2007 in connection with U.S. Appl. No. 11/151,270.
Non-final Office Action mailed Jul. 9, 2008 in connection with U.S. Appl. No. 11/151,270.
Non-final Office Action mailed Nov. 5, 2004 in connection with U.S. Appl. No. 10/438,883.
Non-final Office Action mailed May 3, 2005 in connection with U.S. Appl. No. 10/438,883.
A final Office Action mailed Oct. 18, 2005 in connection with U.S. Appl. No. 10/438,883.
Non-final Office Action mailed Feb. 6, 2007 in connection with U.S. Appl. No. 10/438,883.
A Communication mailed Oct. 9, 2007 in connection with U.S. Appl. No. 10/438,883.
Non-final Office Action mailed Nov. 12, 2008 in connection with U.S. Appl. No. 10/438,883.
Non-final Office Action mailed Feb. 7, 2008 in connection with U.S. Appl. No. 10/815,778.
A final Office Action mailed Nov. 13, 2008 in connection with U.S. Appl. No. 10/815,778.
Non-final Office Action mailed Jul. 2, 2009 in connection with U.S. Appl. No. 10/815,778.
A final Office Action mailed Mar. 15, 2010 in connection with U.S. Appl. No. 10/815,778.
Non-final Office Action mailed Feb. 20, 2007 in connection with U.S. Appl. No. 10/960,960.
A final Office Action mailed Sep. 28, 2007 in connection with U.S. Appl. No. 10/960,960.
Non-final Office Action mailed May 18, 2009 in connection with U.S. Appl. No. 11/657,042.
A final Office Action mailed Dec. 28, 2009 in connection with U.S. Appl. No. 11/657,042.
Non-final Office Action mailed Jan. 14, 2010 in connection with U.S. Appl. No. 11/081,103.
Non-final Office Action mailed Jul. 22, 2009 in connection with U.S. Appl. No. 12/010,984.
Non-final Office Action mailed Oct. 5, 2005 in connection with U.S. Appl. No. 10/424,765.
Non-final Office Action mailed Dec. 18, 2007 in connection with U.S. Appl. No. 11/081,103.
A final Office Action mailed Sep. 19, 2008 in connection with U.S. Appl. No. 11/081,103.
Non-final Office Action mailed Jun. 3, 2009 in connection with U.S. Appl. No. 11/081,103.
Non-Final Office Action mailed Apr. 15, 2010 in connection with U.S. Appl. No. 11/657,042.
International Preliminary Report on Patentability for PCT/US2009/001459, mailed on May 12, 2010.
Final Office Action mailed Mar. 22, 2010 in connection with U.S. Appl. No. 12/010,984.
Search Report and Written Opinion for International Patent Application No. PCT/US2004/010957, issued on Nov. 1, 2004.
International Preliminary Report on Patentability for International Patent Application No. PCT/US2004/010957, issued on Nov. 18, 2005.
Search Report and Written Opinion for International Patent Application No. PCT/US2005/030610, issued on Apr. 7, 2006.
International Preliminary Report on Patentability for International Patent Application No. PCT/US2005/030610, issued on Feb. 26, 2008.
Search Report and Written Opinion for International Patent Application No. PCT/US2005/036878, issued on Sep. 21, 2006.
International Preliminary Report on Patentability for International Patent Application No. PCT/US2005/036878, issued on Apr. 17, 2007.
Search Report and Written Opinion for International Patent Application No. PCT/US2005/008798, issued on Jun. 19, 2006.
International Preliminary Report on Patentability for International Patent Application No. PCT/US2005/008798, issued on Nov. 1, 2006.
Search Report and Written Opinion for International Patent Application No. PCT/US2004/010956, issued on Oct. 28, 2005.
International Preliminary Report on Patentability for International Patent Application No. PCT/US2004/010956, issued on Nov. 18, 2005.
Search Report and Written Opinion for International Patent Application No. PCT/US2005/051796, issued on Jun. 23, 2009.
International Preliminary Report on Patentability for International Patent Application No. PCT/US2008/051796, issued on Jul. 28, 2009.
Search Report and Written Opinion for International Patent Application No. PCT/US2008/085522, issued on Jul. 6, 2009.
Search Report and Written Opinion for International Patent Application No. PCT/US2009/001459, issued on Jul. 6, 2009.
Non-Final Office Action mailed Apr. 15, 2010 in connection with U.S. Appl. No. 12/079,629.
Non-Final Office Action mailed Apr. 12, 2010 in connection with U.S. Appl. No. 12/191,490.
Non-Final Office Action mailed Apr. 26, 2010 in connection with U.S. Appl. No. 12/147,042.
Matsuda et al. (1995) In Vivo Chondrogenesis in Collagen Sponge Sandwiched by Perichondrium. J. Biomater. Sci. Polymer Ed., vol. 7, No. 3, pp. 221-229.
Fujisato et al. (1996) Effect of basic fibroblast growth factor on cartilage regeneration in chondrocyte-seeded collagen sponge scaffold. Biomaterials, vol. 17, No. 2, pp. 155-162.
Aston et al., "Repair of Articular Surfaces by Allografts of Articular and Growth-Plate Cartilage," Journal of Bone and Joint Surgery, Jan. 1986, vol. 68-B, No. 1; pp. 29-35.
Hoffman, "Hydrogels for Biomedical Applications", Advanced Drug Delivery Reviews, 2002, vol. 43, pp. 3-12.
Dahlberg et al., "Demineralized Allogeneic Bone Matrix for Cartilage Repair", Journal of Orthopaedic Research, 1991, vol. 9, pp. 11-19.
Lu et al., "Minced Cartilage without Cell Culture Serves as an Effective Intraoperative Cell Source for Cartilage Repair", Journal of Orthopaedic Research, Jun. 2006, vol. 24, pp. 1261-1270.

Stone et al., "Articular Cartilage Paste Grafting to Full-Thickness Articular Cartilage Knee Joint Lesions: a 2- to 12-Year Follow-up", Arthroscopy: The Journal of Arthoscopic and Related Surgery, Mar. 2006, vol. 22, No. 3, pp. 291-299.

Newman, "Articular Cartilage Repair", American Journal of Sports Medicine, 1998, vol. 26, No. 2, pp. 309-324.

Brittberg et al., "Treatment of Deep Cartilage Defects in the Knee with Autologous Chondrocyte Transplantation", New England Journal of Medicine, Oct. 6, 1994, vol. 331, No. 14, pp. 889-895.

Nixon et al., "Enhanced Repair of Extensive Articular Defects by Insulin-like Growth Factor-I-Laden Fibrin Composites", Journal of Orthopaedic Research, 1999; 17:475-487.

International Cartilage Repair Society, "Cartilage Injury Evaluation Package", www.cartilage.org, 2000.

Richardson et al., "Repair of Human Articular Cartilage After Implantation of Autologous Chondrocytes", Journal of Bone and Joint Surgery [Br], 1999; 81-B:1064-1068.

Brittberg et al., "Autologous Chondrocytes Used for Articular Cartilage Repair: An Update", Clinical Orthopaedics and Related Research, 2001; No. 391 Suppl: S337-S348.

Peterson et al., "Two- to 9-year Outcome After Autologous Chondrocyte Transplantation of the Knee", Clinical Orthopaedics and Related Research, 2000; No. 374: 212-234.

Peterson et al., "Autologous Chondrocyte Transplantation: Biomechanics and Long-term Durability", American Journal of Sports Medicine, 2002, vol. 30, No. 1, pp. 2-12.

Messner et al., "Cartilage Repair: A Critical Review", Acta Orthopaedica Scandinavica, 1996, vol. 67, No. 5, pp. 523-529.

Messner et al., "The Long-term Prognosis for Severe Damage to Weight-bearing Cartilage in the Knee: A 14-year Clinical and Radiographic Follow-up in 28 Young Athletes", Acta Orthopaedica Scandinavica, 1996, vol. 67, No. 2, pp. 165-168.

Buckwalter et al., "Articular Cartilage: Degeneration and Osteoarthritis, Repair, Regeneration, and Transplantation", AAOS Instructional Course Lectures, 1998; 47:487-504.

Breinan et al., "Effect of Cultured Autologous Chondrocytes on Repair of Chondral Defects in a Canine Model", Journal of Bone and Joint Surgery [Am], Oct. 1997; vol. 79-A, No. 10, 1439-1451.

Breinan et al., "Autologous Chondrocyte Implantation in a Canine Model: Change in Composition of Reparative Tissue with Time", Journal of Orthopaedic Research, 2001; 19:482-492.

Brittberg et al., "Rabbit Articular Cartilage Defects Treated with Autologous Cultured Chondrocytes", Clinical Orthopaedics and Related Research, 1996; 326:270-283.

Nehrer et al., "Chondrocyte-seeded Collagen Matrices Implanted in a Chondral Defect in a Canine Model", Biomaterials, 1998; 19:2313-2328.

Vunjak-Novakovic et al., "Bioreactor Cultivation Conditions Modulate the Composition and Mechanical Properties of Tissue-Engineered Cartilage", Journal of Orthopaedic Research, 1999; 17:130-138.

Bursac, "Collagen Network Contributions to Structure-Function Relationships in Cartilaginous Tissues in Compression" (Dissertation), Boston University College of Engineering, 2002.

Gooch et al., "IGF-I and Mechanical Environment Interact to Modulate Engineered Cartilage Development", Biochemical and Biophysical Research Communications, 2001; 286:909-915.

Pei et al., "Growth Factors for Sequential Cellular De- and Re-differentiation in Tissue Engineering", Biochemical and Biophysical Research Communications, 2002; 294:149-154.

Obradovic et al., "Integration of Engineered Cartilage", Journal of Orthopaedic Research, 19:1089-1097, 2001.

Schaefer et al., "Tissue Engineered Composites for the Repair of Large Osteochondral Defects", Arthritis & Rheumatism, 46(9): 2524-2534 (2002).

Pei et al., "Bioreactors Mediate the Effectiveness of Tissue Engineering Scaffolds", The FASEB Journal, 16:1691-1694, published online (Aug. 7, 2002), 10.1096/fj.02-0083fje.

Madry et al., "Gene Transfer of a Human Insulin-like Growth Factor I cDNA Enhances Tissue Engineering of Cartilage", Human Gene Therapy, 13: 1621-1630 (Sep. 1, 2002).

Pearson et al. (eds.), American Association of Tissue Banks, Standards for Tissue Banking, 2008 (12th ed.), pp. 53-56, 86-88.

Ornitz et al., "Protein Family Review: Fibroblast Growth Factors", Genome Biology (2001) 2(3): reviews 3005.1-3005.12, available at http://genomebiology.com/2001/2/3/reviews/3005.1.

Loeser et al., "Basic Fibroblast Growth Factor Inhibits the Anabolic Activity of Insulin-like Growth Factor 1 and Osteogenic Protein 1 in Adult Human Articular Chondrocytes", Arthritis & Rheumatism, vol. 52, No. 12 (Dec. 2005), pp. 3910-3917.

Kato et al., "Fibroblast Growth Factor is an Inhibitor of Chondrocyte Terminal Differentiation", Journal of Biological Chemistry, vol. 265, No. 10 (Apr. 5, 1990) pp. 5903-5909.

Andrés et al., "A Pro-Inflammatory Signature Mediates FGF2-induced Angiogenesis", Journal of Cellular and Molecular Medicine, (Jun. 28, 2008), available at http://www.ncbi.nlm.nih.gov/pubmed/18624773.

Burger et al., "Fibroblast growth factor receptor-1 is expressed by endothelial progenitor cells", Blood, vol. 100, No. 10 (Nov. 15, 2002) 3527-35.

Baird, "Fibroblast growth factors: activities and significance of non-neurotrophin neurotrophic growth factors", Current Opinions in Neurobiology, (1994) 4:78-86.

Mazué et al., "Preclinical and Clinical Studies with Recombinant Human Basic Fibroblast Growth Factor", Annals New York Academy of Sciences, (1991) 329-340.

Aviles et al., "Testing clinical therapeutic angiogenesis using basic fibroblast growth factor (FGF-2)", British Journal of Pharmacology (2003) 140: 637-646.

Nolan et al., "Living Bone Grafts", BMJ, vol. 304, Jun. 13, 1992, pp. 1520 and 1521.

Stone et al., "One-Step American Technique of Articular Cartilage Paste Grafting to Traumatic and Arthritic Defects in the Knee Joint (2-7 Years Follow-Up)", downloaded from http:web.archive.org/web/20041205005845/http://www.stoneclinic.com/onestep.thm; published Dec. 5, 2004.

Feczko et al., "Experimental Results of Donor Site Filling for Autologous Osteochondral Mosaicplasty", Arthroscopy: The Journal of Arthroscopic and Related Surgery, vol. 19, No. 7 (Sep. 2003), pp. 755-761.

Nettles et al., "In Situ Crosslinkable Hyaluronan for Articular Cartilage Repair", 50th Annual Meeting of the Orthopaedic Research Society, Paper No. 0202 (Mar. 2004).

Nettles et al., "Photocrosslinkable Hyaluronan as a Scaffold for Articular Cartilage Repair", Annals of Biomedical Engineering, vol. 32, No. 3, Mar. 2004, pp. 391-397.

Peretti et al., "Cell-Based Bonding of Articular Cartilage: An Extended Study", Journal of Biomedical Materials Research, 64A, 2003, pp. 517-524.

Bugbee, "Fresh Osteochondral Allografting", Operative Techniques in Sports Medicine, Apr. 2000, vol. 8, No. 2, pp. 158-162.

Verbruggen et al., "Repair Function in Organ Cultured Human Cartilage. Replacement of Enzymatically Removed Proteoglycans During Longterm Organ Culture", The Journal of Rheumatology, 12:4, (1985), pp. 665-674.

Peretti et al., "Cell-based Tissue-Engineered Allogeneic Implant for Cartilage Repair" Tissue Engineering, 2000, vol. 6. No. 5, pp. 567-576.

Jackson et al., "Cartilage Substitute: Overview of Basic Science & Treatment Options", Journal of American Academy of Orthopaedic Surgeons, vol. 9, Jan./Feb. 2001, pp. 37-52.

Glowacki, Julie, "Engineered Cartilage, Bone, Joints and Menisci-Potential for Temporomandibular Joint Reconstruction", Cells Tissues Organs, vol. 169, Issue 3, 2001, pp. 302-308.

Peretti et al., "A Biomedical Analysis of an Engineered Cell-Scaffold Implant for Cartilage Repair", Annals of Plastic Surgery, 2001, vol. 46, No. 5, pp. 533-537.

Peretti et al., "Biomechanical Analysis of a Chondrocyte-Based Repair Model of Articular Cartilage", Tissue Engineering, Aug. 1, 1999, vol. 5. No. 4, pp. 317-326.

Abraham, Judith A. et al., (1986) Human Basic Fibroblast Growth Factor: Nucleotide Sequence and Genomic Organization. EMBO Journal 5(10):2523-2528.

Agrawal, Sudhir et al., (1991) Pharmacokinetics. Biodistribution, and Stability of Oligodeoxynucleotide Phosphorothioates in Mice. Proc Natl Acad Sci. USA 88(17):7595-7599.

Arakawa, Tsutomu et al., (1993) Production and Characterization of an Analog of Acidic Fibroblast Growth Factor With Enhanced Stability and Biological Activity. Protein Engineering 6(5):541-546.

Bailly, Karine et al., (2000) Uncoupling of cell proliferation and differentiation activities of basic fibroblast growth factor. FASEB Journal 14(2):333-343.

Bange, Johannes et al., (2002) Cancer progression and tumor cell motility are associated with the FGFR4 Arg388 allele. Cancer Research 62(3):840-846.

Bork, Peer (2000) Powers and pitfalls in sequence analysis: The 70% hurdle. Genome Res. 10(4):398-400.

Bork, Peer and Bairoch, Amnon (1996) Go hunting in sequence databases but watch out for the traps. Trends in Genetics 12(10):425-427.

Brenner, Steven E. (1999) Errors in genome annotation. Trends in Genetics 15(4):132-133.

Cappellen, David et al., (1999) Frequent activating mutations of FGFR3 in human bladder arid cervix carcinomas. Nature Genetics 23(1):18-20.

Chusho, Hideki et al., (2001) Dwarfism and early death in mice lacking C-type Natriuretic Peptide. Proc Natl Acad Sci. 98(7):4016-4021.

Coughlin, Shaun R. et al., (1988) Acidic and basic fibroblast growth factors stimulate tyrosine kinase activity in vivo. J Biol Chem. 263(2):988-993.

Dell'Accio, Francesco et al., (2001) Molecular markers predictive of the capacity of expanded human articular chondrocytes to form stable cartilage in vivo, Arthritis Rheum. 44(7):1608-19.

Doerks, Tobias et al., (1998) Protein annotation: detective work for function prediction. Trends Genet. 14(6):248-250.

Dvorakova, Dana et al., (2001) Changes in the expression of FGFR3 in patients with chronic myeloid leukaemia receiving transplants of allogeneic peripheral blood stem cells British Journal Haematology 13(3):832-835.

Eriksson, A. Elisabeth et al., (1991) Three-dimensional structure of human basic fibroblast growth factor. Proc. Natl. Acad. Sci. USA 88:3441-3445 (XP002936511).

Ezzat Shereen et al., (2002) Targeted expression of a Human pituitary tumor-derived isoform of FGF Receptor-4 Recapitulates Pituitary Tumorigenesis. Journal of Clinical Investigation 109(1):69-77.

Faham, Salem et al., (1998) Diversity does make a difference: fibroblast growth factor—Heparin interactions. Curr Opin Struct Biol 8(5):578-586.

Fingl, Edward and Woodbury, Dixon M. (1975) General Principles. In: The Pharmacological Basis of Therapeutics. Fifth edition. Goodman, Louis S. and Gilman, Alfred editors. 1:1-45.

Gargiulo, B. J. et al., (2002) Phenotypic modulation of human articular chondrocytes by bistratene A. Eur Cell Mater. 3:9-18.

Givol, David and Yayon, Avner (1992) Complexity of FGF receptors: genetic basis for structural diversity and functional specificity FASEB J. 6(15):3362-3369.

Hecht, H. J. et al., (2000) Structure of fibroblast growth factor 9 shows a symmetric dimmer with unique receptor-and heparin-binding interfaces. Acta Cryst. D57:378-384.

Johnson, Daniel E. and Williams, Lewis T. (1993) Structural and functional diversity in the FGF receptor multigene family. Adv Cancer Res. 60:1-41.

Kirikoshi, Hiroyuki et al., (2000) Molecular cloning and characterization of Human FGF-20 on chromosome 8p21.3-p22. Biochem Biophys Res Commun. 274(2):337-343.

Kuroda, S. et al., (1999) Anabolic effect of aminoterminally truncated Fibroblast Growth Factor 4 (FGF4) on bone. Bone 25(4):431-437.

Nakatake, Yuhki et al., (2001) Identification of a novel fibroblast growth factor. FGF-22, preferentially expressed in the inner root sheath of the hair follicle. Biochim Biophys Acta. 1517(3):460-463.

Ngo, J. Thomas et al., (1994) Computational complexity, protein structure prediction, and the Levithal Paradox. In: The Protein Folding Problem and Tertiary Structure Prediction. K. Merz Jr. and S. Le Grand, Editors. 433-506 see also table of contents.

Nishimura, Tetsuya et al., (2000) Identification of a Novel FGF, FGF-21, Preferentially Expressed in the Liver. Biochim Biophys Acta 1492(1):203-206.

Okada-Ban, Mai et al., (2000) Fibroblast growth factor-2. International Journal of Biochemistry & Cell Biology 32 (3):263-267.

Olsen, Shaun K. (2003) Fibroblast growth factor (FGF) homologous factors share structural but not functional homology with FGFs. J Biol Chem. 278(36):34226-342236.

Ornitz, David M. et al., (1996) Receptor specificity of the fibroblast growth factor family. J Biol Chem. 271(25)1 5292-7.

Ornitz, David M. (2000) FGFs, heparan sulfate and FGFRs: Complex interactions essential for development. Bio Essays 22:108-112.

Pellegrini, Luca et al., (2000) Crystal structure of fibroblast growth factor receptor ectodomain bound to ligand and heparin. Nature 407(6807):1029-1034.

Pillai, Omathanu and Panchagnula, Ramesh (2001) Polymers in drug delivery. Curr Opin Chem Biol 5 (4):447-451.

Plotnikov, Alexander N. et al., (1999) Structural basis for FGF receptor dimerization and activation. Cell 98 (5):641-650.

Plotnikov, Alexander N. et al., (2000) Crystal structures of two FGF-FGFR complexes reveal the determinants of ligand-receptor specificity. Cell 101(4): 413-424.

Sahni, Malika et al., (1999) FGF signaling inhibits chondrocyte proliferation and regulates bone development through the STAT-1 pathway Genes Devel. 13(11):1361-1366.

Schlessinger, Joseph et al., (2000) Crystal structure of a ternary FGF-FGFR-1 Heparin complex reveals a dual role for heparin in FGFR binding and dimerization. Mol Cell 6(3):743-750.

Schmal, H. et al., (2007) bFGF influences human articular chondrocyte differentiation. Cytotherapy 9(2):184-93.

Seno, Masaharu et al., (1990) Carboxyl-terminal structure of basic fibroblast growth factor significantly contributes to its affinity for Heparin. Eur J Biochem. 188:239-245.

Shao, Zhang-Qiang et al., (2006) Effects of intramyocardial administration of slow-release basic fibroblast growth factor on angiogenesis and ventricular remodeling in a rat infarct model. Circ. J. 70(4):471-477.

Skolnik, Jeffrey and Fetrow, Jacquelyn S. (2000) From genes to protein structure and function: novel applications of computational approaches in the genomic era. Trends BioTechnol. 18(1):34-39.

Sleeman, Matthew et al., (2001) Identification of a new fibroblast growth factor receptor, FGFR5. Gene 271 (2):171-182.

Smith, Temple and Zhang, Xiaolin (1997) The challenges of genome sequence annotation or The devil is in the details. Nat Biotechnol. 15(12):1222-1223.

Springer, Barry A. et al., (1994) Identification and Concerted Function of Two Receptors Binding Surfaces on Basic Fibroblast Growth Factor Required for Mitogenesis. The Journal of Biological Chemistry 269(43):26879-26884.

Stauber, Deborah J. et al., (2000) Structural interactions of fibroblast growth factor receptor with its ligands. Proc Natl Acad Sci USA 97(1):49-54.

Vajo, Zoltan et al., (2000) The Molecular and Genetic Basis of Fibroblast Growth Factor Receptor 3 Disorders: The Achondroplasia Family of Skeletal Dysplasias, Muenke Craniosynostosis, and Crouzon Syndrome with Acanthosis Nigricans. Endocrine Rev. 21(1):23-39.

Wells, James A. (1990) Additivity of mutational effects in proteins. Biochemistry 29(37):8509-8517.

Yamashita, Tetsuo et al., (2000) Identification of a novel fibroblast growth factor, FGF-23, preferentially expressed in the ventrolateral thalamic nucleus of the brain. Biochemical and Biophysical Research Communications 277 (2):494-498.

Yayon, Avner et al., (1991) Cell surface, heparin-like molecules are required for binding of basic fibroblast growth factor to its high affinity receptor. Cell 64(4):841-848.

Yee, Cindy J. et al., (2000) Analysis of fibroblast growth factor receptor 3 S249C mutation in cervical carcinoma. Journal of the National Cancer Institute 92(22):1848-1849.

U.S. Appl. No. 12/966,674, filed Dec. 13, 2010.

U.S. Appl. No. 13/025,722, filed Feb. 11, 2011.

Non-final Office Action for U.S. Appl. No. 12/043,001, mailed May 11, 2011.

Supplemental Search Report for European Patent Application No. 05728956.3, dated May 2, 2011.

Zhang, Jiandong et al., (1991) Three-dimensional structure of human basic fibroblast growth factor, a structural homolog of interleukin 1 Beta. Proc Natl Acad Sci. USA 88(8):3446-3450.

Zhu, Hengyi et al., (1995) Glu-96 of basic fibroblast growth factor is essential for high affinity receptor binding. Journal of Biological Chemistry 270(37):21869-21874.

Zhu, Hengyi et al., (1997) Analysis of high-affinity binding determinants in the receptor binding epitope of basic fibroblast growth factor. Protein Engineering 10(4):417-421.

Carr, M. E. Jr. and Alving, B. M. (1995) Effect of fibrin structure on plasmin-mediated dissolution of plasma clots. Blood Coag. Fibrinol. 6(6):567-573.

Carr, Marcus E. (1988) Fibrin formed in plasma is composed of fibers more massive than those formed from purified fibrinogen. Thromb. Haemost. 59(3):535-539.

Cook, James L. et al., (2003) Biocompatibility of three-dimensional chondrocyte grafts in large tibial defects of rabbits. Am J Vet Res. 64(1):12-20.

Gao, Jizong et al. (2002) Repair of osteochondral defect with tissue-engineered two-phase composite material of injectable calcium phosphate and hyaluronan sponge, Tissue Engin. 13(5):827-837.

Gruber, Reinhard et al., (2002) Platelets stimulate proliferation of bone cells: involvement of platelet-derived growth factor, microparticles and membranes. Clin Oral Implants Res. 13(5):529-535.

Haisch, A. et al., (2000) Preparation of a pure autologous biodegradable fibrin matrix for tissue engineering. Med Biol Eng Comput. 38(6):686-689.

Itokazu, M. et al., (1997) The sustained release of antibiotic from freeze-dried fibrin-antibioticcompound and efficacies in a rat model of osteomyelitis. Infection 25(6):359-363.

Sims, C. Derek et al., (1998) Tissue engineered neocartilage using plasma derived polymer substrates and chondrocytes. Plastic & Recon. Surg. 101(6):1580-1585.

"Young's Modulus." Entry on http://en.wikipedia.org. accessed Oct. 27, 2005. 3 pages.

Bradford, Marion M. (1976) A Rapid and Sensitive Method for the Quantitation of Microgram Quantities of Protein Utilizing the Principle of Protein-Dye Binding. Analytical Biochemistry 72(1-2):248-254.

Atala et al. (1993) Injectable alginate seeded with chondrocytes as a potential treatment for vesicoureteral reflux. J. of Urology 150(2 Pt 2):745-7.

Temenoff et al., "Review: Tissue engineering for regeneration of articular cartilage", Biomaterials 21 (2000) pp. 431-440.

Hunziker, "Articular cartilage repair: are the intrinsic biological constraints undermining this process insuperable?", Osteoarthritis and Cartilage 7 (1999) pp. 15-28.

Final Office Action for U.S. Appl. No. 11/081,103, mailed Aug. 11, 2010.

Non-Final Office Action for U.S. Appl. No. 12/010,984, mailed Aug. 16, 2010.

U.S. Appl. No. 12/881,988, filed Sep. 14, 2010.

Search Report and Written Opinion for International Patent Application No. PCT/US2010/085522, issued Jan. 14, 2010.

U.S. Appl. No. 12/924,132, filed Sep. 21, 2010.

Non-final Office Action with regard to U.S. Appl. No. 12/381,072, mailed Jan. 20, 2011.

Non-final Office Action with regard to U.S. Appl. No. 12/924,132, mailed Mar. 1, 2011.

Final Office Action for U.S. Appl. No. 12/179,034, mailed Jan. 27, 2012.

Non-final Office Action for U.S. Appl. No. 12/381,072, mailed Jan. 23, 2012.

First Action Interview Pilot Program Pre-Interview Communication for U.S. Appl. No. 12/508,892, mailed Jan. 17, 2012.

Non-final Office Action for U.S. Appl. No. 12/924,132, mailed Feb. 21, 2012.

Communication pursuant to Article 94(3) EPC for European Patent Application No. 08 782 728.3, dated Aug. 9, 2011.

International Preliminary Report on Patentability for International Patent Applicaton No. PCT/US2010/000108, mailed Jul. 26, 2011.

First Action Interview Pilot Program Pre-Interview Communication for U.S. Appl. No. 12/328,306, mailed Dec. 22, 2011.

Final Office Action for U.S. Appl. No. 12/328,306, mailed Apr. 19, 2012.

Final Office Action for U.S. Appl. No. 12/881,988, mailed May 11, 2012.

Final Office Action for U.S. Appl. No. 11/081,103, mailed May 18, 2012.

Sedgwick et al., "Studies into the influence of carrageenan-induced inflammation on articular cartilage degradation using implantation into air pouches", British Journal of Experimental Pathology, vol. 66, (1985), pp. 445-453.

First Action Interview Pilot Program Pre-Interview Communication for U.S. Appl. No. 12/696,366, mailed Oct. 13, 2011.

Non-final Office Action for U.S. Appl. No. 12/881,988, mailed Oct. 26, 2011.

Non-final Office Action for U.S. Appl. No. 11/081,103, mailed Nov. 28, 2011.

Non-final Office Action for U.S. Appl. No. 12/508,892, mailed Dec. 7, 2011.

Non-final Office Action for U.S. Appl. No. 12/322,996, mailed Apr. 4, 2011.

Guilak, Farshid; "Functional Tissue Engineering: The Role of Biomechanics in Articular Cartilage Repair", Clinical Orthopaedics and Related Research, No. 391 S, pp. S295-S305, (c) 2001 Lipponcott Williams & Wilkins, Inc., (11 pages).

Spangenberg, Kimberly, M., et al. "Histomorphometric Analysis of a Cell-Based Model of Cartilage Repair", Tissue Engineering, vol. 8, No. 5, 2002, (8 pages).

* cited by examiner

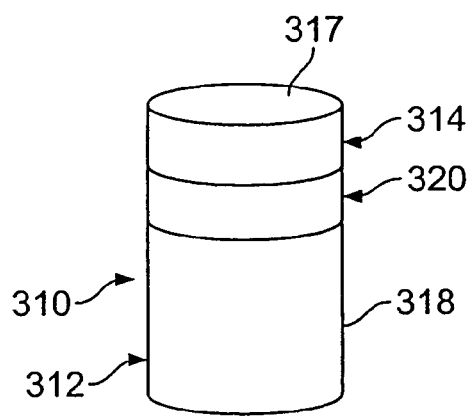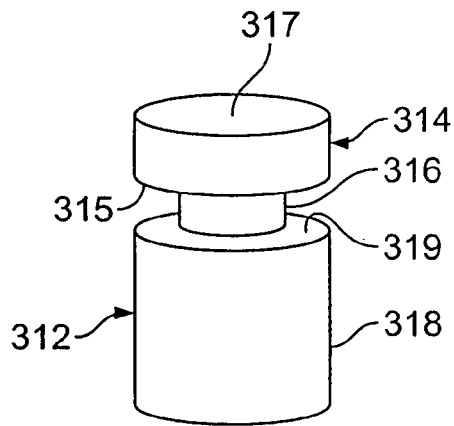
FIG. 19                    FIG. 20
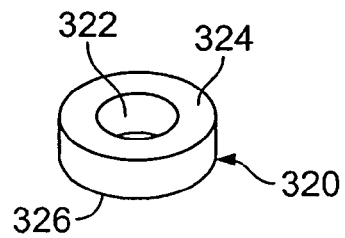
FIG. 21
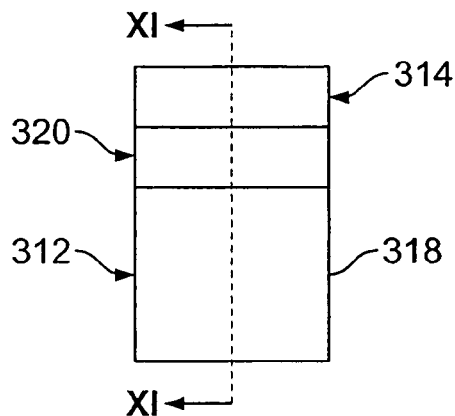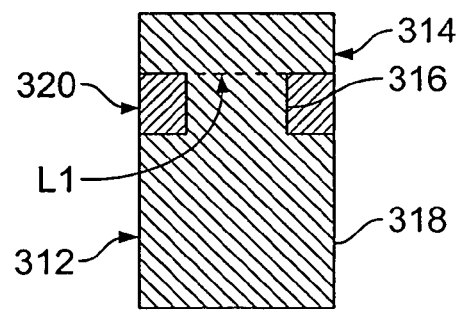
FIG. 22                    FIG. 23

CANCELLOUS CONSTRUCTS, CARTILAGE PARTICLES AND COMBINATIONS OF CANCELLOUS CONSTRUCTS AND CARTILAGE PARTICLES

RELATED APPLICATIONS

This application is a divisional application of U.S. patent application Ser. No. 12/381,072, filed Mar. 5, 2009, which claims priority under 35 U.S.C. §119(e) to (a) U.S. Provisional Patent Application Ser. No. 61/189,252, filed Aug. 15, 2008, and (b) U.S. Provisional Patent Application Ser. No. 61/205,433, filed Jan. 15, 2009, and which is a continuation-in-part of (i) U.S. patent application Ser. No. 11/657,042, filed Jan. 24, 2007, now U.S. Pat. No. 7,837,740; (ii) U.S. patent application Ser. No. 12/043,001, filed Mar. 5, 2008, now abandoned, which claims priority under 35 U.S.C. §119 (e) to U.S. Provisional Patent Application Ser. No. 60/904,809, filed Mar. 6, 2007; (iii) U.S. patent application Ser. No. 12/328,306, filed Dec. 4, 2008, which claims priority under 35 U.S.C. §119(e) to U.S. Provisional Patent Application Ser. No. 60/996,800, filed Dec. 5, 2007; and (iv) U.S. patent application Ser. No. 12/079,629, filed Mar. 26, 2008, now abandoned, which is a divisional of U.S. patent application Ser. No. 10/960,960, filed Oct. 12, 2004, now abandoned. All of the foregoing related patent applications are incorporated by reference herein in their entirety.

BACKGROUND OF THE INVENTION

Chondrogenesis is the process of growth and differentiation of cartilage cells (chondrocytes), leading to the proliferation of such cells and the development of a robust, specialized extracellular matrix surrounding such cells. Cartilage is the specialized matrix of chondrocytes and particular cartilage extracellular matrix components surrounding such chondrocytes. Disordered growth and repair of cartilage cells results in tissue with primarily fibrotic morphology, as opposed to the cartilage extracellular matrix resulting from normal growth and development of chondrocytes and having characteristic proteoglycan and collagen II components.

Articular cartilage injury and degeneration present medical problems to the general population which are constantly being addressed by orthopedic surgeons. Thousands of arthroplastic and joint repair procedures are performed every year in the United States, including total hip and total knee arthroplasties and open arthroscopic procedures to repair cartilaginous defects of the knee.

Reference is now made to FIG. 1, which illustrates a knee joint having articular cartilage tissue forming a lining which faces the joint cavity on one side, and is linked to the subchondral bone plate by a narrow layer of calcified cartilage tissue on the other side. Articular cartilage consists primarily of extracellular matrix with a sparse population of chondrocytes distributed throughout the tissue. Articular cartilage is composed of chondrocytes, type II collagen fibril meshwork, proteoglycans, and water. Active chondrocytes are unique in that they have a relatively low turnover rate and are sparsely distributed within the surrounding matrix. The collagens give the tissue its form and tensile strength and the interaction of proteoglycans with water gives the tissue its stiffness to compression, resilience and durability. The articular cartilage provides a low friction bearing surface over the bony parts of the joint. If the lining becomes worn or damaged resulting in lesions, joint movement may be painful or severely restricted. Whereas damaged bone typically can regenerate successfully, articular cartilage regeneration is quite limited because of its limited regenerative and reparative abilities.

Articular cartilage lesions generally do not heal, or heal only partially under certain biological conditions, due to the lack of nerves, blood vessels and a lymphatic system. The limited reparative capabilities of articular cartilage usually results in the generation of repair tissue that lacks the structure and biomechanical properties of normal articular cartilage. Generally, the healing of the defect results in a fibrocartilaginous repair tissue that lacks the structure and biomedical properties of articular cartilage and degrades over the course of time. Articular cartilage lesions are frequently associated with disability and with symptoms such as joint pain, locking phenomena and reduced or disturbed function. These lesions are difficult to treat because of the distinctive structure and function of articular cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for millions of physician visits and thousands of hospital admissions.

BRIEF SUMMARY OF THE INVENTION

The present invention is directed towards a particulate allograft cartilage material, which may optionally be incorporated into an allograft cancellous bone construct, that exhibits improved chondrogenesis and decreased fibrous tissue formation in both in vivo and in vitro environments. The cartilage defect repair material includes lyophilized, freeze-milled allograft cartilage particles having a size within a range of from about 10 microns to about 210 microns.

A method of placing the aforementioned cartilage defect repair material in a cartilage defect site includes the steps of (a) cutting a patient's tissue to remove diseased cartilage from the cartilage defect site; (b) placing said cartilage defect repair material into the cartilage defect site; and (c) placing a cover over the placed cartilage defect repair material.

A method for making the aforementioned cartilage defect repair material includes the steps of lyophilizing allograft cartilage, and freeze-milling the allograft cartilage so as to form cartilage particles.

A method of repairing articular cartilage includes the step of placing a therapeutically effective amount of the aforementioned cartilage defect repair material into a cartilage defect site, wherein, subsequent to placement of the therapeutically effective amount of the cartilage defect repair material into the cartilage defect site, a greater percentage of repair tissue generated in the cartilage defect site is articular cartilage as compared to equivalent cartilage defect sites left untreated or treated with microfracture.

A construct according to the present invention includes a cap member that is at least partially derived from demineralized cancellous bone, and a base member having first and second ends. The base member includes a first bore extending into the base member from the first end in a generally axial direction, and a second bore extending generally transversely from an exterior wall of the base member to the first bore. The cap member includes an upper section and a stem depending from the upper section, wherein the stem is dimensioned to insertably engage the first bore such that the upper section is adjacent the first end of the base. The stem includes a third bore extending generally transversely into the stem from an exterior surface thereof, wherein the third bore is alignable with the second bore when the stem is in engagement with the first bore. The construct also includes at least one pin which is dimensioned to engage the second and third bores when the second and third bores are aligned, thereby securing the cap member to the base member. The cap member includes a plurality of lyophilized, freeze-milled cartilage particles, at least a majority of which have a dimension, when dry, that does not exceed 210 microns.

Another construct according to the present invention includes a cap member that is at least partially derived from demineralized cancellous bone, and a base member having first and second ends. The base member includes a first bore extending into the base member from the first end in a generally axial direction, a second bore extending generally transversely from an exterior wall of the base member to the first bore, and a third bore extending generally transversely from the exterior wall of the base member to the first bore. The third bore is formed opposite the second bore and is alignable with the second bore. The base member includes an upper annular edge adjacent the first end and the first bore, and an island formed in the so as to be substantially concentrically positioned with respect to the upper annular edge, and to form an annular recess between the island and an interior wall of the base member adjacent the upper annular edge. The cap member includes an upper section and a stem depending from the upper section. The stem is dimensioned to insertably engage the first bore, such that the upper section is adjacent the first end of the base, wherein the is hollow and includes a cavity formed therein which is dimensioned to receive the island therein. The annular recess of the base member is dimensioned to receive the stem therein. The stem includes a fourth bore extending generally transversely into the stem from an exterior surface thereof. The fourth bore is alignable with the second bore and the third bore when the stem is in engagement with the first bore. The stem also includes a fifth bore extending generally transversely into the stem from the exterior wall thereof. The fifth bore is formed opposite the fourth bore and is alignable with the second bore and the third bore when the stem is in engagement with the first bore. The island includes a sixth bore which extends generally transversely between opposed exterior surfaces of the island. The sixth bore is alignable with the second bore, the third bore, the fourth bore and the fifth bore when the stem is in engagement with the first bore. The construct also includes at least two pins which are dimensioned to engage the second bore, the third bore, the fourth bore, the fifth bore and the sixth bore when the second bore, the third bore, the fourth bore, the fifth bore and the sixth bore are aligned, thereby securing the cap member to the base member. The cap member includes a plurality of lyophilized, freeze-milled cartilage particles, at least a majority of which have a dimension, when dry, that does not exceed 210 microns.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention.

FIG. 19 is a top perspective view of a multi-piece cancellous construct produced in accordance with another embodiment of the present invention;

FIG. 20 is a top perspective view of a base member employed by the multi-piece construct illustrated in FIG. 19;

FIG. 21 is a top perspective view of a ring-shaped support member of the construct illustrated in FIG. 19;

FIG. 22 is a side elevational view of the construct illustrated in FIG. 19, as assembled;

FIG. 23 is a cross-sectional view, taken along line XI-XI and looking in the direction of the arrows, of the construct illustrated in FIG. 22;

FIGS. 45A, 45C, 45E, and 45G are Safranin-O stained for proteoglycan assessment; FIGS. 45B, 45D, 45F, and 45H are anti-collagen II stained for collagen II assessment; FIGS. 45A and 45B represent microfracture; FIGS. 45C and 45D represent an empty defect; FIGS. 45E and 45F represent a construct without cartilage particles; and FIGS. 45G and 45H represent a construct in combination with (i.e., loaded with) freeze-milled cartilage particles.

Figure 1:
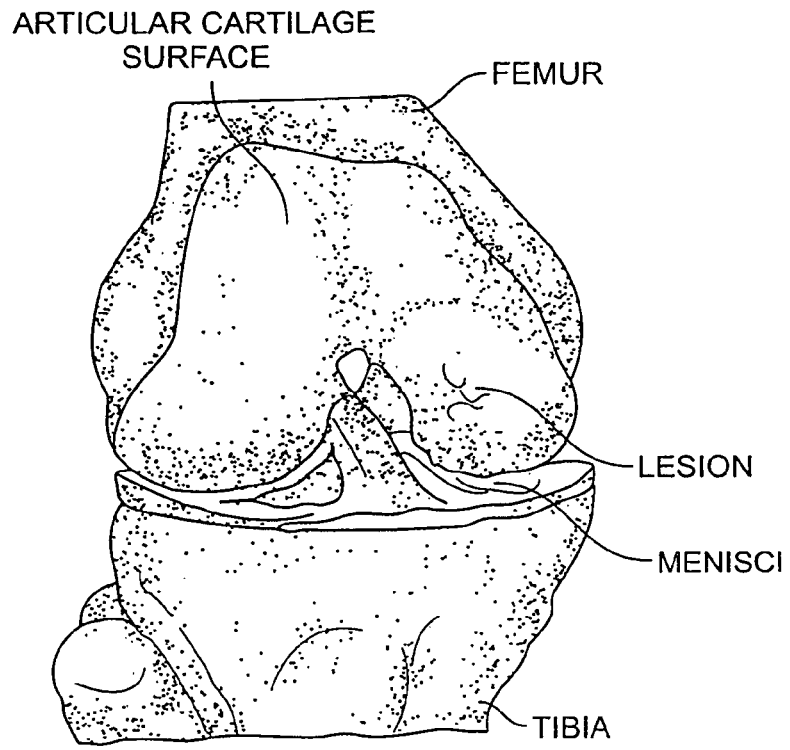
FIG. 1 is an anatomical illustration of a knee joint having articular cartilage in which a lesion has formed.

While the above-identified drawings set forth presently disclosed embodiments, other embodiments are also contemplated, as noted in the detailed description. This disclosure presents illustrative embodiments by way of representation and not limitation. Numerous other modifications and embodiments can be devised by those skilled in the art which fall within the scope and spirit of the principles of the presently disclosed invention.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

Cancellous Constructs

Cartilage repair constructs (e.g., scaffolds or implants) are disclosed herein. The term "construct", as used hereinafter, is defined as a device that includes one or multiple components which are constructed from milled pieces of bone, or other biocompatible materials, wherein the device is intended to be implanted at the site of a tissue defect (e.g., an articular cartilage defect) to repair the defect. In one embodiment, the constructs components are constructed of allograft cancellous bone. More particularly, most or all of the components of the allograft constructs are preferably derived from dense allograft cancellous bone that may originate from proximal or distal femur, proximal or distal tibia, proximal humerus, talus, calceneus, patella, or ilium, which bones are received from a tissue donor and are stored frozen until processing time, preferably at $-70°$ C. Components of the constructs may also be constructed of allograft cortical bone, and/or xenograft bone when the same is properly treated, or other materials, as discussed below. Cancellous bone is preferred because its porous structure enables it to act as a natural matrix for receiving and retaining therein a mixture containing cartilage particles and various bioactive chondrogenic materials for the repair of articular cartilage defects, as discussed further below. Cancellous bone also acts as a conduit for tissue ingrowth and regeneration.

In one embodiment, the constructs may be prepared according to the following procedure:

(a) The frozen donor bone is allowed to thaw in warm USP water (i.e., water that is purified to have a sterility level in accordance with United States Pharmacopeia standards). Once thawed, the bone is processed, with the cancellous bone tissue being cut therefrom into sheets or blocks.

(b) The cancellous bone blocks are flushed with high-pressure USP water in order to remove from the cancellous bone blocks any lipids therein and the bone fragments and/or shavings produced during the cutting of the blocks.

(c) The cancellous bone blocks are placed in an agitating device, and treated with a detergent used in delipidization (e.g., Polysorbate 80) to further eliminate/minimize the lipid content of the blocks. After delipidization, the cancellous bone blocks are cleaned with USP water and dried.

(d) The cancellous bone blocks are soaked in USP water prior to milling. The blocks are milled into the desired shapes for the various components of the construct using a milling machine.

(e) After milling, the construct components are rinsed with USP water and trimmed.

(f) The finished construct components are then soaked in detergent (e.g., Polysorbate 80).

(g) Following the detergent soak, the construct components are rinsed and soaked in USP water and dried.

(h) The construct components are then soaked in an antibiotic solution (e.g., gentamicin) and rinsed and soaked in USP water and dried.

(i) At least some of the construct components (i.e., the base member and pins described below) are then soaked in detergent (e.g., Polysorbate 80). Following the detergent soak, these construct components are rinsed and soaked in USP water and dried. These construct components are then soaked in a hydrogen peroxide solution, and then rinsed and soaked in USP water and dried.

(j) At least one of the construct components (i.e., the cap member described below) is demineralized using techniques known in the art, such as a soak in 0.6N HCl (or any other suitable dilute acid) for a period of time sufficient to attain a predetermined mineral content level (e.g., less than 0.5% w/w residual calcium). Following demineralization, the demineralized construct component(s) is rinsed and cleaned with USP water. The demineralized construct component(s) may also be cleaned with a hydrogen peroxide solution. The demineralization process is further discussed hereinbelow in connection with specific construct component(s).

(k) The demineralized construct component(s) may be soaked in a buffered solution having a pH of 7.4 (e.g., Sorenson phosphate buffered saline (PBS) solution) or a similar or higher pH level to restore the pH of the demineralized construct component(s) a physiological level of about 7.0. Following the buffered solution soak, the demineralized construct component(s) is rinsed and cleaned with USP water and dried.

(l) The construct components are assembled, as further described below.

(m) The assembled construct is then be subjected to a tissue processing protocol, including, for example, a soak in ethanol (e.g., 70% SDA-3A ethanol). The assembled construct is then rinsed with USP water and dried.

Modifications to the above construct preparation procedure may be made.

The construct components are then frozen at −20° C. to −100° C., preferably at −70° C., and lyophilized (i.e., freeze-dried) to reduce the water content to be within a range of about 0.1% to about 8.0%. The lyophilized construct components are then secured in an appropriate moisture barrier package for long-term storage, whereby the lyophilized construct components may be stored at room temperature for up to five years. Examples of moisture barrier packaging that may be used include a flexible foil laminate pouch and a high moisture barrier thermoformed tray heat sealed to the foil lidstock. The pouch may be made of materials that can be laminated with foil (e.g., PET, PE, LDPE, LLDPE, HDPE, Nylon), while the tray may be made of a laminate material (e.g., PETG/PCTFE laminate, PVC/PCTFE laminate, PETG/COC laminate, PVC/COC laminate, COC/PCTFE laminate). To preserve the sterility of the construct components, packaging with sterile barrier properties is used. The package may consist of more than one layer to facilitate the transfer of the construct components into the sterile field of an operating room or other sterile environments.

Alternatively, the construct components may be frozen at −20° C. to −100° C., preferably at −70° C., (i.e., without lyophilization), whereby the frozen construct components may be stored at the aforementioned temperature(s) for up to five years. The frozen construct components may be stored in a multiple-layered moisture barrier package to maintain sterility, as discussed above.

The construct components that have been processed and stored as described above are produced in various standard sizes (i.e., diameters and heights). The construct components may be assembled prior to storage, and stored unloaded (i.e., without the addition of any substance thereto), or with a lyophilized cartilage particle mixture and/or other substances loaded therein, as discussed below.

In an embodiment, the assembled construct is shaped in the form of a cylinder, for easy insertion into bores cut into a patient to remove osteochondral defect areas, as explained hereinafter. The construct may also be formed in other shapes, such as rectangular, square and oval configurations.

Prior to a surgical articular cartilage repair procedure, a surgeon may pre-order a set of constructs for use in connection with the surgery. During surgery, a surgeon selects one of the constructs having a diameter that matches the diameter of a cylindrical hole (i.e., a blind bore) that has been cut in the lesion or defect area of the host tissue (i.e., the subchondral bone and the overlying articular cartilage) of a patient, and inserts the construct into the bore. The construct that is selected by the surgeon will have a diameter sized to facilitate an interference fit between the construct and a sidewall of the bore. Alternatively, the diameter of the construct may be sized to facilitate a press-fit between the construct and the bore sidewall. Different embodiments of the construct and the associated surgical implantation procedures are disclosed in the following sections and in the corresponding drawings.

With reference to FIGS. 2-12, an embodiment of a multi-piece construct 20 is illustrated as having a base member 22 and a cap member 30 that is held fixed in place in the base member 20 by a pin 40. In an embodiment, the outer diameter of the assembled construct 20 may be within a range from about 5 mm to about 35 mm, and its overall height may be within a range from about 5 mm to about 20 mm. This embodiment of the construct is also disclosed in U.S. patent application Ser. No. 11/657,042 filed Jan. 24, 2007; U.S. Provisional Patent Application Ser. No. 60/996,800 filed Dec. 5, 2007; and U.S. patent application Ser. No. 12/328,306 filed Dec. 4, 2008, all of which are incorporated by reference herein in their entirety.

Referring now to FIGS. 2-8, the base member 22 may be constructed of mineralized cancellous bone (e.g., cancellous bone in its natural, undemineralized state containing approximately 60% mineral by weight or more). The cancellous bone of the base member 22 is used to replace the subchondral bone removed when a surgeon cuts a bore in the area of an adjacent cartilage defect. The base member 22 is shaped in the form of a cylinder (see FIGS. 2, 3 and 8) for easy insertion into bores cut into the patient to remove osteochondral defect areas. The base member 22 may also be formed in other shapes.

In an alternative embodiment, a portion and/or surface of the base member 22 may be demineralized (the demineralization process is explained below). Such demineralization of the base member 22 increases the osteoinductivity of the bone by increasing exposure of the growth factors in the base member 22. In other words, demineralization of a portion of the base member 22 causes a patient's surrounding subchondral bone to more rapidly incorporate the base member 22 after implantation.

Referring now to FIGS. 2 and 5-8, the base member 22 includes a blind bore 23 having a bottom surface 24. A first plurality of longitudinal through-going bores 25 extends from the bottom surface 24 through the base member 22 and terminates in openings formed in a planar bottom end 26 of the base member 22 (see FIGS. 5-8). The base member 22 includes an upper annular edge 27, which forms a seat for the cap member 30. The base member 22 also includes first and second through-going transverse bores 28, 29 in opposite sides of a wall of the base member 22. The transverse bores 28, 29 extend through the exterior of the base member 22 intermediate the upper annular edge 27 and the bottom surface 24 of the blind bore 23, and intersect the blind bore 23. The transverse bores 28, 29 are also co-axial with respect to one another.

In one embodiment, the upper annular edge 27 includes a second plurality of through-going bores 31, which are circumferentially positioned around the blind bore 23, and extend parallel to a central longitudinal axis of the base member 22. The through-going bores 31 extend from the upper annular edge 27 to the bottom end 26 of the base member 22, forming openings in the bottom end 26. The through-going bores 25 and 31 have a smaller diameter than that of the blind bore 23, with a diameter that may be within a range of from about 0.5 mm to about 2.0 mm. The through-going bores 25 and 31 facilitate the migration of blood throughout the construct 20 to promote cartilage growth in the cap member 30 and integration with the adjacent cartilage, and to promote bone growth in the base member 22 and integration with the adjacent bone. More particularly, blood from the bleeding subchondral bone contains bone marrow, cells, nutrients and other substances that may aid in the incorporation of the components of the construct 20 in the bore and the remodeling of both cartilage and bone tissue adjacent the construct 20. For example, stem cells contained in the bone marrow are capable of differentiation into chondrocytes, and can therefore promote cartilage growth in the cap member 30 when blood is directed through the through-going bores 25 and 31. Alternatively, the through-going bores 25, 31 can be omitted from the base member 22.

The cancellous bone composition of the base member 22 is similar to that of the surrounding subchondral bone. The cylindrical shape of the base member 22 provides mechanical support to the cap member 30, thereby enabling the construct 20 to act as a load-bearing construct. In addition, the cancellous bone of the base member 22 is porous, thereby enabling blood from the adjacent subchondral bone (see below) to permeate rapidly throughout the construct 20, providing the host cells necessary for healing.

In one aspect of the invention, the cancellous base member 22 of the construct 20 presents a structural, osteoconductive matrix through which new bone is formed. The high degree of porosity of the cancellous bone allows for rapid penetration of blood, nutrients, and cells from the surrounding bleeding bone environment. This was observed during implantation of the construct in a critical sized in vivo goat osteochondral defect.

The porous, three-dimensional nature of the cancellous bone also provides considerable surface area for cellular attachment throughout the construct 20, including in the base member 22. Bone healing occurs through a process of bone resorption followed by new bone formation. Here, the presence of the acellular, non-demineralized bone of the base member 22 triggers a biologic response in which osteoclasts begin to break down the implanted bone matrix. This event then leads to the activation of osteoblasts, via paracrine signaling, which starts to deposit new bone matrix. The final result of this ongoing remodeling is a de novo cancellous bone structure that is fully integrated into the subchondral bone at the defect site.

Reference is now made to FIGS. 9-12, in which the cap member 30 is illustrated. The cap member 30 includes a cylindrical upper section 32 that has a thickness that is similar to that of a patient's surrounding articular cartilage layer (e.g., in a range of about 1.5 mm to about 7 mm). The upper section 32 includes an upper surface 33, an outer curved wall 34 and a lower surface 35 which is seated adjacent the upper annular edge 27 of the base member 22 when the components are mounted together (see FIGS. 3 and 4). The upper surface 33 may be planar. Alternatively, the upper surface 33 may be milled to be curved (e.g., convex), so as to conform to the physiological curvature of the adjacent articular cartilage layer and/or the adjacent bone surfaces of a joint (e.g., the knee). In alternative embodiments, larger constructs may have a cap member that has multiple stem sections and a base with an inverse "female" pattern adapted to receive the stem sections.

With continued reference to FIGS. 9-12, an integral cylindrical stem 36 depends from the bottom surface 35 of the upper section 32, and is dimensioned so as to be received in and by the blind bore 23 of the base member 22. More particularly, the stem 36 has a length that is approximately equal to the depth of the blind bore 23 and a diameter that is approximately equal to the diameter of the blind bore 23. Alternatively, the length of the stem 36 may be less than the depth of the blind bore 23.

Figure 3:
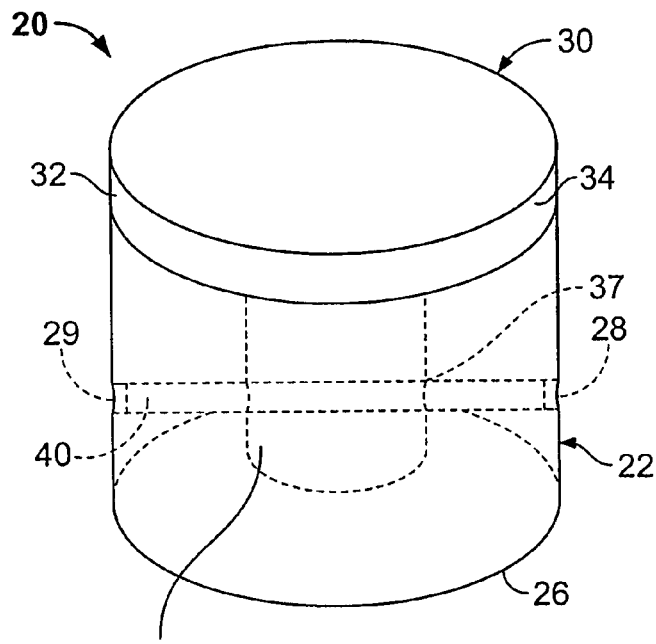
FIG. 3 is a top perspective view of the multi-piece construct of FIG. 2, as assembled.
Figure 4:
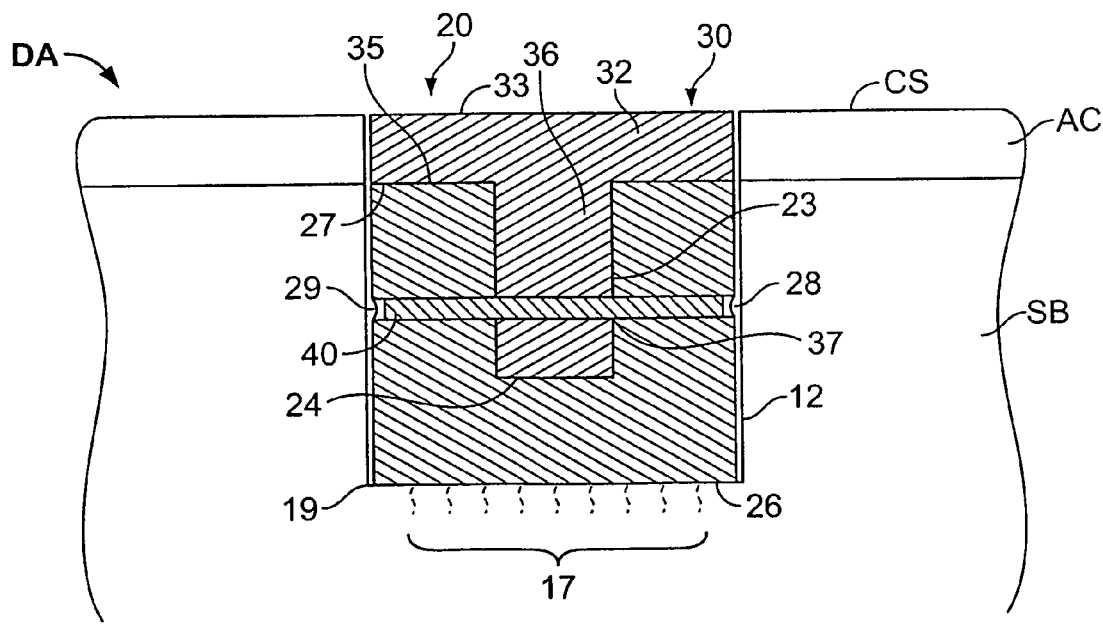
FIG. 4 is a cross-sectional view of the multi-piece construct of FIG. 2 which has been placed in a bore of a cartilage defect area in a patient according to a method performed in accordance with the present invention.
Figure 5:
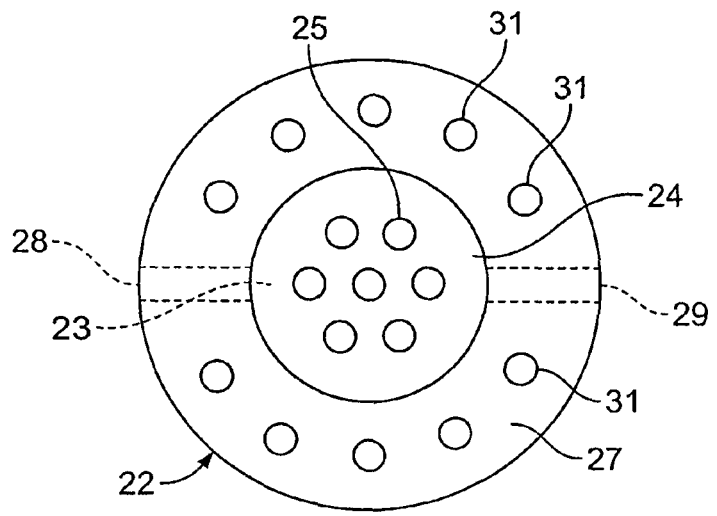
FIG. 5 is a top plan view of a base member employed by the multi-piece construct of FIG. 2.
Figure 6:
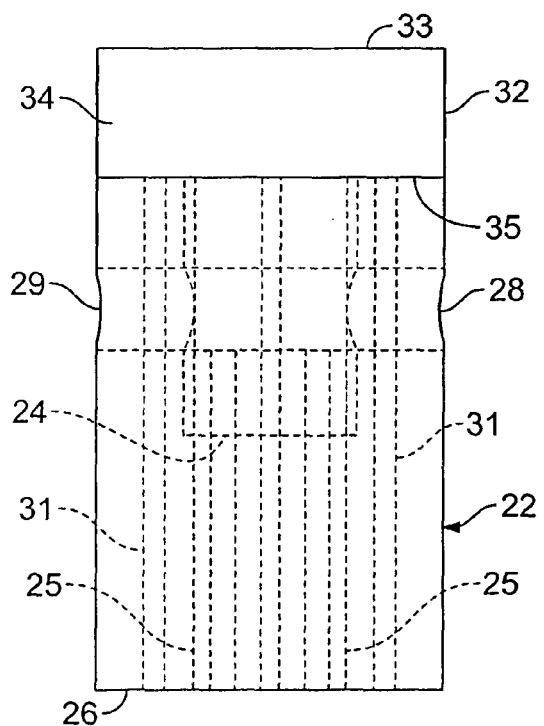
FIG. 6 is a side elevational view of a base member and a cap member employed by the multi-piece construct of FIG. 2, wherein the base member and cap member have been coupled.
Figure 7:
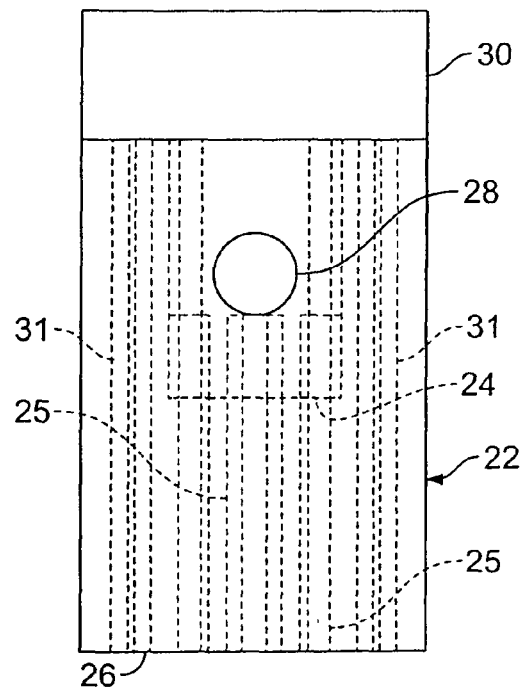
FIG. 7 is a side elevational view of the coupled base member and cap member of the multi-piece construct of FIG. 2 in which the coupled base member and cap member have been rotated 90° from their position shown in FIG. 6.
Figure 8:
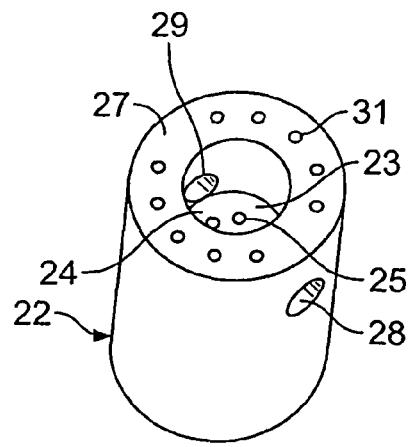
FIG. 8 is a top perspective view of the base member employed by the multi-piece construct of FIG. 2.
Figure 9:
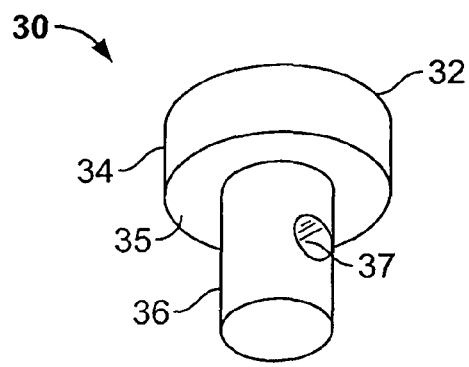
FIG. 9 is a bottom perspective view of the cap member employed by the multi-piece construct of FIG. 2.
Figure 10:
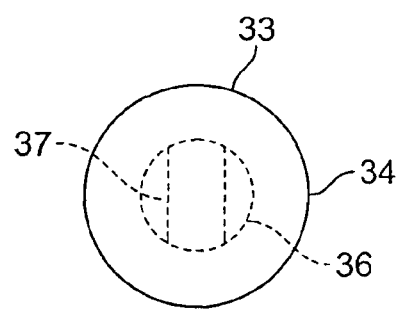
FIG. 10 is a top plan view of the cap member of FIG. 9.
Figure 11:
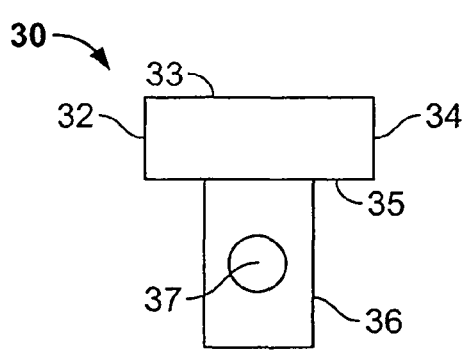
FIG. 11 is a side elevational view of the cap member of FIG. 9.
Figure 12:
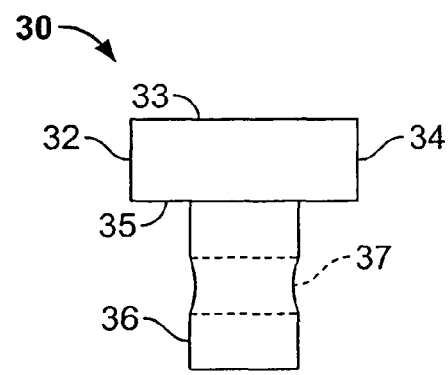
FIG. 12 is a side elevational view of the cap member of FIG. 9 in which the cap member has been rotated 90° from its position shown in FIG. 11.

In one embodiment, the stem 36 includes a transverse through-going bore 37, which may be aligned with the transverse through-going bores 28, 29 of the base member 22 to receive the pin 40 therein when the base member 22 and the cap member 30 have been assembled (see FIGS. 3 and 4). The pin 40 is cylindrically shaped in this embodiment, with a diameter that is slightly smaller than that of the transverse, through-going bores 28, 29, 37. In one embodiment, the diameter of the pin 40 is 2.5 mm. The pin 40 has a length that is approximately equal to the diameter of the base member 22. Alternatively, the length of the pin 40 may be slightly less than the diameter of the base member 22.

The pin 40 and the through-going bores 28, 29, 37 may alternatively have other shapes (e.g., a square or triangular cross-section). The through-going bores 28, 29, 37 may alternatively have different configurations in the base member 22 and cap member 30, respectively (e.g., horizontal, diagonal, etc.). In another embodiment, the construct may include more than one set of pins and through-going bores. Alternatively, a pin assembly (e.g., a multi-piece pin) may be used.

Figure 2:
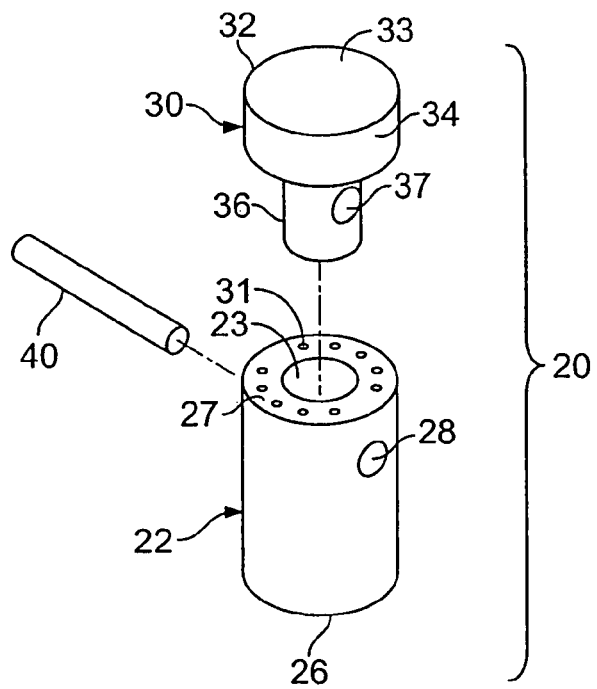
FIG. 2 is an exploded perspective view of a multi-piece cancellous construct produced in accordance with an exemplary embodiment of the present invention.

In one embodiment, and as illustrated in FIGS. 2-4, the pin 40 is inserted into the base member 22 through the transverse through-going bore 29, through the transverse through-going bore 37 of the cap member 30 and through the transverse through-going bore 28, to hold the cap member 30 in place within the base member 22, and thereby secure the cap member 30 to the base member 22. In one embodiment, the pin 40 is made of cancellous bone. Alternatively, the pin 40 may be made of cortical bone or even a synthetic material. The cap member 30 can also be secured to the base member 22 by a staple, a suture, a press-fit or an adhesive compound such as a fibrin-based glue or the organic glues discussed herein.

In one embodiment, the cap member 30 is formed of demineralized allograft cancellous bone. As discussed above, the porous nature of cancellous bone enables it to serve as a natural matrix for receiving and retaining therein a mixture (e.g., a paste or gel) containing cartilage particles for the repair of articular cartilage defects. Embodiments of the cartilage particle mixture are discussed below.

In one embodiment, the cap member 30 is demineralized using techniques known in the art. For instance, the cap member 30 may be soaked in 0.6N HCl (or any other suitable dilute acid) for a period of time sufficient to attain a predetermined mineral content level (e.g., less than 0.5% w/w residual calcium). In another embodiment, physical and/or chemical methods may be utilized in order to accelerate the demineralization process. The soak may be agitated and/or heated to accelerate the demineralization reaction. Following demineralization, the demineralized cap member 30 is rinsed and cleaned with USP water. The demineralized cap member 30 may also be cleaned with a hydrogen peroxide solution.

In one embodiment, the cap member 30 is made of bone having reduced osteoinductivity, or of non-osteoinductive bone, which may be preferable when the regeneration of healthy cartilage is desired, rather than the regeneration of bone. In an embodiment, the demineralized cap member 30 may be treated to reduce its osteoinductivity, or to render the bone non-osteoinductive, using techniques known in the art. For instance, an oxidizing agent such as a 3% hydrogen peroxide solution may be used to soak the demineralized cap member 30 in order to reduce its osteoinductivity, or to render it substantially non-osteoinductive. In another embodiment, physical and/or chemical methods may be utilized in order to accelerate the process whereby osteoinductivity is reduced. Following the hydrogen peroxide soak, the demineralized cap member 30 is rinsed and cleaned with USP water. Alternatively, the reduction or inactivation of inherent bone osteoinductivity may be accomplished by chemical or thermal treatment, or by high energy irradiation.

In one embodiment, to restore the pH of the demineralized cap member 30 to a physiological level of about 7.0, the demineralized cap member 30 may be soaked in a saline solution (e.g., Sorenson phosphate buffered saline (PBS) solution) having a pH of 7.4, or in another buffered solution having a similar or higher pH level. The demineralized cap member 30 is soaked in the PBS solution for a time sufficient to return it to a physiological pH level. In another embodiment, physical and/or chemical methods may be utilized in order to accelerate the pH restoration process. Following the saline solution soak, the demineralized cap member 30 is rinsed and cleaned with USP water and dried.

Because demineralized cancellous bone is predominantly Type I collagen, the bone is sponge-like, elastic and deformable, exhibiting shape memory properties. As a result, the demineralized cap member 30, which is formed of porous cancellous bone, may more effectively receive and retain therein a mixture (e.g., a paste or gel) containing cartilage particles for repair of articular cartilage defects. Further, the demineralized cap member 30 possesses mechanical properties that enhance its performance as an articular cartilage implant. More particularly, the sponginess of the demineralized cap member 30 enables the upper surface 33 of its upper section 32 to conform to the natural curvature of the joint surface. This facilitates the treatment of large cartilage defects without the risk that a "proud" edge (i.e., an edge that extends higher than the surrounding articular cartilage layer) of the construct 20 will cause damage to the opposing joint surface during articulation because the deformable, spongy demineralized cap member 30 will allow the proud upper surface 33 to yield to the opposing joint surface during articulation.

In an alternative embodiment, only the upper section 32 of the cap member 30 is demineralized and the stem 36 (or a portion thereof) remains mineralized. This alternate configuration enables the mineralized stem 36 to act as a rigid (e.g., non-spongy) core within the blind bore 23 of the base member 22 to provide further support for load bearing of the joint.

In one embodiment, the demineralized cap member 30 (or portion thereof) is configured to promote healing of a patient's articular cartilage layer, while the distinct mineralized base member 22 promotes healing of the underlying subchondral bone, thereby providing a two-phase implant construction. In accordance with this configuration, the assembled construct 20 possesses a relatively uniform demineralized upper region, including the cap member 30, that is distinct from the mineralized base member 22.

In one embodiment, the components of the construct 20 are assembled by inserting the stem 36 of the demineralized cap member 30 into the blind bore 23 of the base member 22 (see FIGS. 2-4). As explained above, the demineralized cap member 30 and the base member 22 may be positioned so that their respective through-going bores 37, 28 and 29 are aligned. The pin 40 is inserted into one end of the through-going bore 29 on one side of the base member 22 and pushed through the through-going bores 29, 37 and 28 until its leading end is flush with the opposite side of the base member 22. The assembled construct 20 is checked to ensure that the demineralized cap member 30 is secured within the base member 22. If the leading end of the pin 40 protrudes beyond the base member 22, it may trimmed (e.g., with sandpaper) until the leading end is substantially flush with the side of the base member 22. The pin 40 may alternatively be formed to have a length that is shorter than the diameter of the base member 22 (see FIG. 4).

In one embodiment, the assembled construct 20 may then be subjected to a tissue processing protocol, including, for example, a soak in ethanol (e.g., 70% SDA-3A ethanol). The assembled construct 20 is then rinsed with USP water and dried.

In an embodiment, a cartilage particle mixture as described herein is then loaded into and/or applied to the assembled construct 20. For example, the mixture-loading may be performed according to the following protocol:

(1) freeze-milled allograft cartilage particles that were all processed from the same tissue donor are weighed and transferred to a small mixing jar;

(2) 0.78 cc of phosphate buffer saline (PBS) solution are added for each 0.22 g of cartilage particles, and the solution is stirred with a spatula to create a paste-like mixture;

(3) the mixture is transferred to a 10 cc syringe and allowed to equilibrate for five to ten minutes, with a syringe cap preferably used to cover the tip of the syringe and prevent the mixture from drying out;

(4) the assembled construct 20 is placed in a mixture-loading fixture and a small portion of the cartilage particle mixture is dispensed onto the top of the assembled construct 20 (e.g., the upper section 32 of the cap member 30);

(5) a large spatula is used to spread the cartilage particle mixture throughout the cap member 30; and (6) excess mixture is wiped off and a smooth surface is created on the upper surface 33 and the outer curved wall 34 of the cap member 30.

The quantity of cartilage particle mixture deposited onto the cap member 30 depends on a variety of factors that may be appreciated by those skilled in the art, including, for example, the dimensions of the cap member 30, the viscosity and density of the cartilage particle mixture, the anatomical and/ or physical properties of the allograft tissues from which the cap member 30 and the cartilage particles are derived, etc.

In one embodiment, and as shown in FIG. 4, the construct 20 has a height that is substantially equal to the depth of a bore 12, wherein the base member 22 is supported by a bottom surface 19 of the bore 12. This type of load-bearing support protects the construct 20 from damage caused by micromotion at the interface of the bore 12 and construct 20, which may produce undesired fibrous tissue interfaces and subchondral cysts.

In an alternative embodiment, the height of the construct 20 may be less than the bore depth. In this embodiment, the base member 22 is supported by the sidewall of the bore 12 due to the aforementioned interference fit within the bore 12. This type of load-bearing support also protects the construct 20 from the aforementioned damage caused by micromotion at the interface of the bore 12 and construct 20.

In an embodiment, the surgical repair of a cartilage or osteochondral defect using the construct 20 may be performed according to the following operation. A surgeon debrides (e.g., shaves away) the damaged or diseased portion of articular cartilage and the underlying subchondral bone from an articular cartilage defect area DA, as shown in FIG. 4. A defect area bore 12 is cut in the patient's articular cartilage AC and underlying subchondral bone SB. The defect removal and bore creation may be performed using a flat-bottom drill. The subchondral bone SB that is exposed by the creation of the bore 12 may then be subjected to a microfracture procedure, whereby the surgeon uses an awl to create a number of small portals 17 in the subchondral bone SB, causing it to bleed into the bore 12.

Next, the surgeon may modify the size and/or shape of the construct 20 for implantation into the bore 12. For example, the surgeon may chamfer the bottom end 26 of the base member 22 to facilitate insertion of the construct 20 into the bore 12. The bottom end 26 of the base member 22 may also be trimmed by the surgeon at this time to shorten the height of the construct 20, thereby matching the construct 20 to the depth of the bore 12, if the bore depth is less than the original height of the construct 20.

Still referring to FIG. 4, the construct 20 is then implanted into the bore 12 in a dry (i.e., lyophilized) state. An inserter device may be used to place the construct 20 into the bore 12. In order to expedite this step, the surgeon may be provided with an inserter device in which the construct 20 has been removably secured prior to surgery. Alternatively, the construct 20 may be inserted into the bore 12 by using a tamp and a mallet. Once inserted, the construct 20 is re-hydrated by the bleeding from the surrounding host tissue (e.g., the cartilage AC and the subchondral bone SB). The construct 20 may also be re-hydrated by the bleeding bone portals 17 if the surgeon performed the aforementioned microfracture procedure. The construct 20 may also be rehydrated in a solution such as saline prior to implantation.

The height of the construct 20 may determine its placement in the bore 12, and, hence, the position of the upper surface 33 in relation to surface of the adjacent cartilage AC. The construct 20 may be placed in the bore 12 so that the upper surface 33 of the cap member 30 is substantially flush with a surface CS of the patient's adjacent articular cartilage AC to form a smooth, continuous load-bearing surface, as illustrated in FIG. 4. The bottom end 26 of the base member 22 may be supported by a bottom surface 19 of the bore 12. Alternatively, the construct 20 may be placed so that the upper surface 33 is slightly higher than the surface CS of the adjacent cartilage AC, so as to be proud in relation thereto. The construct 20 may also be placed so that the upper surface 33 is slightly lower than the surface CS of the adjacent cartilage AC, thereby providing a space, or pocket, for tissue growth therewithin. A cartilage particle mixture may also be placed in such space or pocket. The cartilage particle mixture promotes chondrocyte (and/or other cellular) migration into (i.e., from the adjacent cartilage AC), attachment and proliferation in the bore 12, and enhances tissue integration between the cap member 30 and the adjacent articular cartilage AC. The cartilage particle mixture, which may contain freeze-milled cartilage particles, can be in the form of a paste or gel, and is described in greater detail below.

The construct 20 may have a diameter that is substantially equal to the diameter of the bore 12, in order to create an interference fit therebetween (e.g., an interference fit with the sidewall of the bore 12). Alternatively, the construct 20 may have a diameter that is larger than the diameter of the bore 12, in order to create a press-fit therein.

Various adhesive materials may be used, for example, to seal the cartilage particles in the construct 20 and to prevent synovial fluid infiltration, and/or, for example, to affix the construct 20 in place within the bore 12 post-implantation. These adhesive materials include suitable organic glue materials that can be found commercially, including fibrin-based sealants derived from human and/or bovine plasma, such as TISSEEL® (Baxter International, Inc., USA), CROSSEAL® (Johnson & Johnson, USA) and BIOGLUE® (Cryolife, Inc., USA); a fibrin-based adhesive, such as TISSUCOL® (Immuno AG, Austria), Adhesive Protein (Sigma Chemical, USA), Dow Corning Medical Adhesive B (Dow Corning, USA); a tissue adhesive consisting of collagen-derived particles and topical thrombin, such as FLOSEAL® (Baxter International, Inc.); a combination of polyethylene glycol polymers that have the ability to chemically bond to each other, as well as to tissue surfaces, such as COSEAL®(Angiodevice International GMBH Corporation, Switzerland); fibrinogen thrombin, elastin, collagen, casein, albumin, keratin, and/or adhesive compounds and/or organic glues and the like.

Affixation means such as, for example, sutures, staples and/or screws may also be used to seal the cartilage particles in the construct 20 and to prevent synovial fluid infiltration, and/or to affix the construct 20 in place within the bore 12 post-implantation. The construct 20 may also be press-fit within the bore 12.

It is envisioned that cells may be inserted into the cap member 30 before the construct 20 is implanted into the defect area DA. Alternatively, cells may be inserted into the entire construct 20. Such cells may be added during implantation of the construct 20 instead. The cells may also be added after implantation. Such cells include bone marrow cells, stem cells, progenitor cells and chondrocytes. Such cells may be allogeneic. The cells may alternatively be autologous. The cellular density of the cells in the construct is a therapeutically effective density. This mixture can also support the chondrogenic-stimulating factors discussed herein. Such factors are described, for example, in U.S. patent application Ser. No. 12/010,984, filed Jan. 31, 2008, which is incorporated herein by reference in its entirety.

In another embodiment, the cap member 30 may be loaded with the cartilage particles (e.g., in a mixture) described herein. In another embodiment, the cap member 30 may be loaded with the cartilage particles described herein, and then an exogenous growth factor and/or endogenous growth factor activator may be added to the cap member 30 and/or incorporated into the cartilage particles. In another embodiment, the cap member 30 may be loaded with the growth factors and/or the activators described herein. In another embodiment, the cap member 30 that has been loaded with growth factors may be subsequently loaded with cartilage particles. In another embodiment, the cartilage particles previously equilibrated with activated and/or exogenous growth factors may be subsequently added to the construct 20.

The construct 20 may also be modified to include regionally-specific chondrogenic and osteogenic regions in the cap member 30 and the base member 22, respectively. More particularly, the cap member 30 may incorporate cartilage particles (e.g., in a mixture) and/or chondrogenic growth factors, as described herein, and the base member 22 may incorporate demineralized bone matrix and/or osteogenic growth factors. Alternatively, as growth factor activity is often context-dependent, a single growth factor having environmentally-specific activity may be incorporated in both the base member 22 and the cap member 30. In another embodiment, any combination of chondrogenic and/or osteogenic growth factors may be employed.

Figure 13:
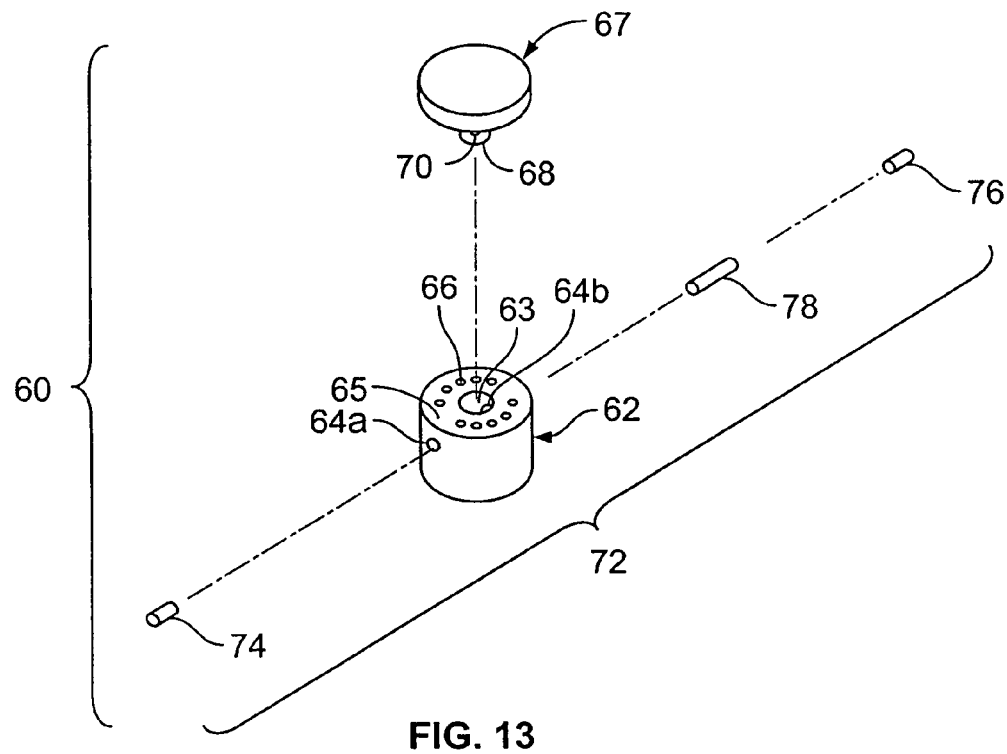
FIG. 13 is an exploded perspective view of a multi-piece cancellous construct produced in accordance with another embodiment of the present invention.

Another embodiment of a multi-piece cancellous construct 60 is illustrated in FIG. 13. This embodiment is also disclosed in U.S. Provisional Patent Application Ser. No. 60/996,800 filed Dec. 5, 2007, and U.S. patent application Ser. No. 12/328,306 filed Dec. 4, 2008, both of which are incorporated by reference herein in their entirety. At least some of the modifications in the dimensions and the surgical insertion of the construct 20 described above may be made in connection with the construct 60 as well.

The construct 60 includes a base member 62 having a blind bore 63, a pair of coaxial, transverse through-going bores 64a, 64b, and an upper annular edge 65 having a plurality of through-going bores 66. The construct 60 also includes a cap member 67 having a stem 68 with a transverse through-going bore 70 therein, and a pin assembly 72. The base member 62 and the cap member 67 are constructed in the same manner and from the same materials as the base member 22 and the cap member 30, respectively, of the construct 20 illustrated in FIGS. 2-12, and are assembled in substantially the same way in relation to each other. The pin assembly 72 includes first and second end pin portions 74, 76, respectively, and a center pin portion 78. Alternatively, a single pin may be used with the construct 60. In another embodiment of the construct 60, the upper annular edge 65 of the base member 62 does not include the through-going bores 66.

Upon assembly of the construct 60, the stem 68 of the cap member 67 is inserted into the blind bore 63 of the base member 62. The stem 68 may be arranged so that the transverse through-going bores 64a, 64b of the base member 62 and the through-going bore 70 of the stem 68 are axially aligned to receive the pin assembly 72 therein. The center pin portion 78 is inserted into the through-going bore 64b of the base member 62 and through the through-going bore 70 of the stem 68 so as to secure the cap member 67 to the base member 62. The first end pin portion 74 is then inserted into the through-going bore 64a until it abuts the end of the center pin portion 78 adjacent to it. The second end pin portion 76 is then inserted into the through-going bore 64b until it abuts the opposite end of the center pin portion 78 (e.g., the end opposite the first end pin portion 74). The end pin portions 74, 76 remain within the through-going bores 64a, 64b of the base member 62 and retain the center pin portion 78 therein and in the through-going bore 70 of the stem 68. The pin assembly 72 is preferably used in larger constructs (e.g., having a diameter greater than 12 mm), for which the construction of a single pin of adequate length may be difficult or impractical.

Figure 14:
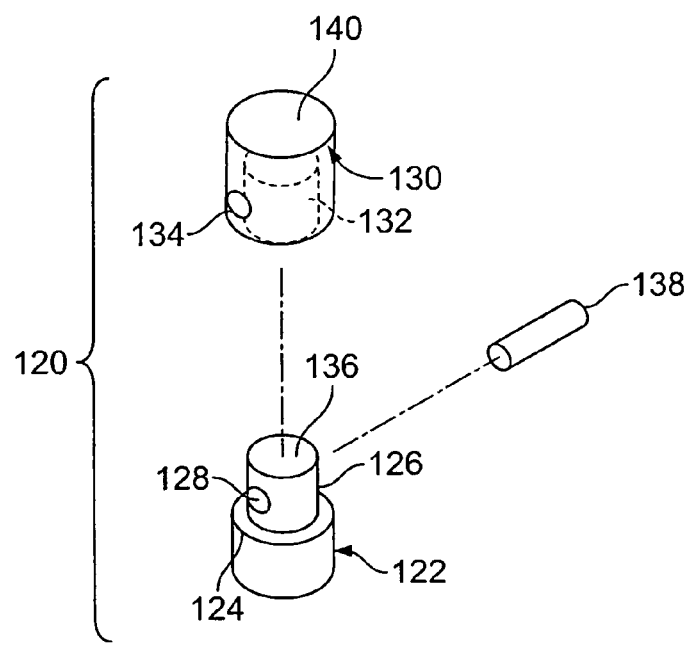
FIG. 14 is an exploded perspective view of a multi-piece cancellous construct produced in accordance with another embodiment of the present invention.

Another embodiment of a multi-piece cancellous construct 120 is illustrated in FIG. 14 and includes a modified arrangement of the elements of the construct 20 illustrated in FIGS. 2-12. More particularly, a cylindrically shaped base member 122 includes an annular shoulder 124. An integral stem 126 extends upwardly from the base member 122 and has a smaller diameter than that of the base member 122. The stem 126 includes a transverse through-going bore 128. The construct 120 also includes a cylindrical cap member 130 having a blind bore 132 dimensioned to receive the stem 126 therein. The cap member 130 also includes a transverse through-going bore 134, which intersects the blind bore 132. The stem 126 includes an upper surface 136, which is preferably planar and dimensioned to fit against an interior end surface of the blind bore 132 of the cap member 130. At least some of the modifications in the dimensions and the surgical insertion of the construct 20 described above may be made in connection with the construct 120 as well. This embodiment is also disclosed in the aforementioned U.S. Provisional Patent Application Ser. No. 60/996,800 filed Dec. 5, 2007 and U.S. patent application Ser. No. 12/328,306 filed Dec. 4, 2008, both of which are incorporated by reference herein in their entirety.

Still referring to FIG. 14, the cap member 130 is positioned on the stem 126 to receive same and so that the transverse bores 128, 134 are axially aligned to receive a pin 138 therein. The pin 138 holds the cap member 130 and the base member 122 together in a fixed relationship, operating like the corresponding components of the construct 20 illustrated in FIGS. 2-12. An upper surface 140 of the cap member 130 may be planar, so as to form a smooth continuous surface with the surrounding articular cartilage layer of the patient. Alternatively, the upper surface 140 may be milled to be curved (e.g., convex), so as to conform to the physiological curvature of the adjacent articular cartilage layer and/or the adjacent bone surfaces of a joint (e.g., the knee). The cap member 130 is made of demineralized cancellous bone, whereas the base member 122 is preferably made of mineralized cancellous bone.

In another embodiment, the cap member 130 may be loaded with the cartilage particles (e.g., in a mixture) described herein. In another embodiment, the cap member 130 may be loaded with cartilage particles described herein, and then an exogenous growth factor and/or endogenous growth factor activator may be added to the cap member 130 and/or incorporated into the cartilage particles. In another embodiment, the cap member 130 may be loaded with the growth factors and/or the activators described herein. In another embodiment, the cap member 130 that has been loaded with growth factors may be subsequently loaded with cartilage particles. In another embodiment, the cartilage particles previously equilibrated with activated and/or exogenous growth factors may be subsequently added to the construct 120.

The assembled construct 120 is placed within a bore to replace an excised cartilage defect in a similar manner as that described above for the construct 20. The height of the construct 120 may determine its placement in a bore formed in the defect area of a patient, and, hence, the position of the upper surface 140 in relation to surface of the patient's adjacent articular cartilage. The construct 120 may be placed in the bore so that the upper surface 140 of the cap member 130 is substantially flush with the surface of the patient's adjacent articular cartilage to form a smooth, continuous load-bearing surface. A bottom end of the base member 122 may be supported by a bottom surface of the bore. Alternatively, the construct 120 may be placed so that the upper surface 140 is slightly higher than the surface of the adjacent cartilage, so as to be proud in relation thereto. The construct 120 may also be placed so that the upper surface 140 is slightly lower than the surface of the adjacent cartilage, thereby providing a space, or pocket, for tissue growth therewithin. A cartilage particle mixture may also be placed in such space or pocket. The cartilage particle mixture promotes chondrocyte (and/or other cellular) migration into (i.e., from the adjacent cartilage), attachment and proliferation in the bore, and enhances tissue integration between the cap member 130 and the adjacent articular cartilage. The cartilage particle mixture, which may contain freeze-milled cartilage particles, can be in the form of a paste or gel, and is described in greater detail below.

The construct 120 may have a diameter that is substantially equal to the diameter of the bore, in order to create an interference fit therebetween (e.g., an interference fit with the sidewall of the bore). Alternatively, the construct 120 may have a diameter that is larger than the diameter of the bore, in order to create a press-fit therein. Any of the suitable organic glue materials described above may be used to keep the construct 120 fixed in place in the bore.

The construct 120 may also be loaded with the aforementioned cartilage particle mixture and/or one or more of the additives described herein in connection with the other embodiments of the construct. Demineralized bone matrix, growth factors, cells grown outside of the patient's body and/or one or more of the other biological substances described herein may also be incorporated into the construct 120.

Reference is now made to FIGS. 15-18, which illustrate another embodiment of a multi-piece cancellous construct 220. This embodiment is well-suited for large constructs (e.g., having a diameter of 15 mm or greater), which are utilized for the repair of more extensive articular cartilage lesions and defects. At least some of the modifications in the dimensions and the surgical insertion of the construct 20 described above may be made in connection with the construct 220 as well.

The construct 220 includes a base member 222, a cap member 224 and two pins 226, 228, all of which fit together to minimize the open interior space within the construct 220, as further explained below. Alternatively, one pin may be used with the construct 220.

Figure 15:
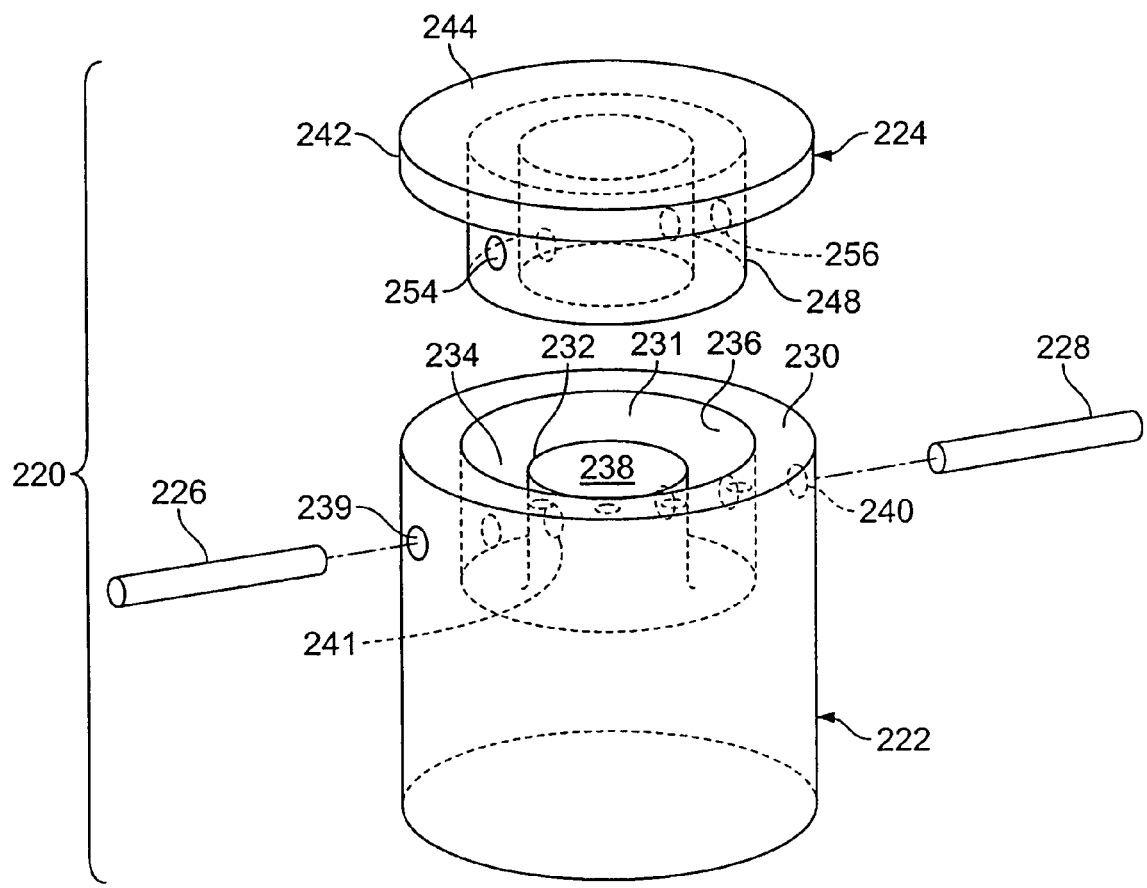
FIG. 15 is an exploded perspective view of a multi-piece cancellous construct produced in accordance with another embodiment of the present invention.
Figure 17:
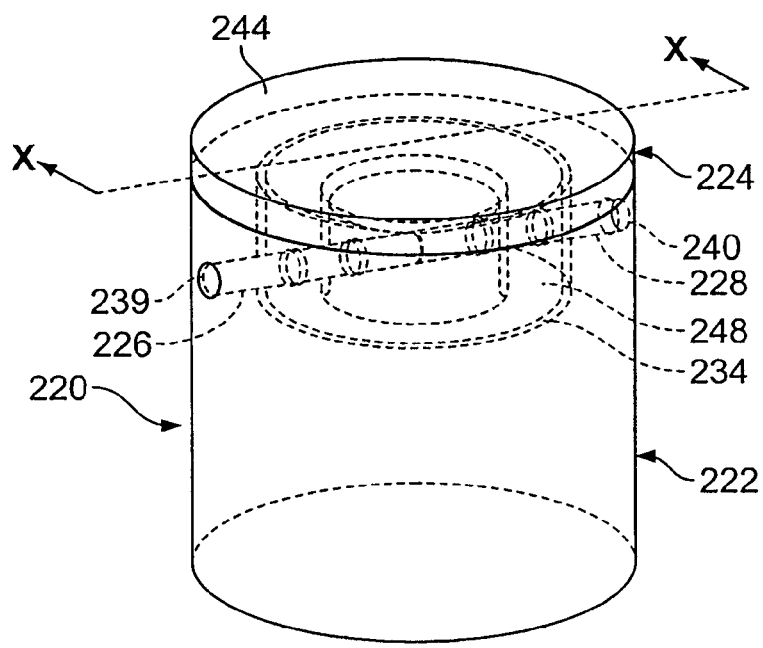
FIG. 17 is a top perspective view of the multi-piece construct of FIG. 15, as assembled.
Figure 18:
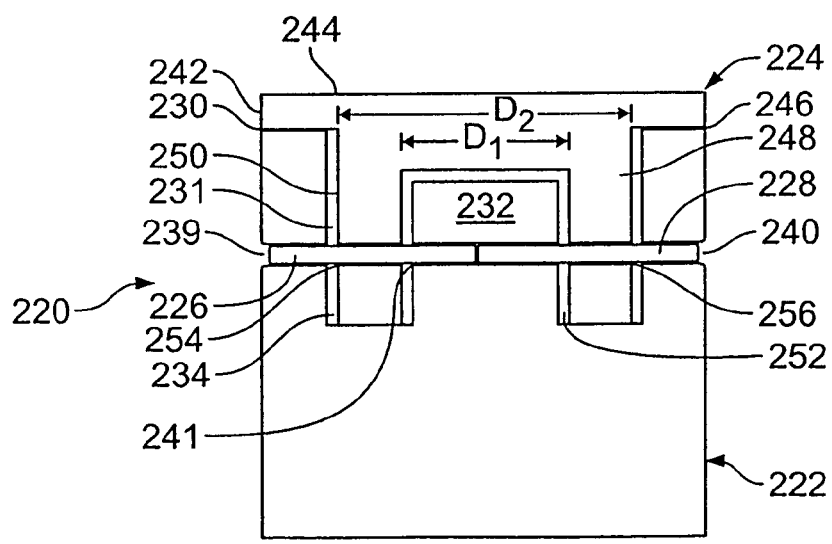
FIG. 18 is a schematic cross-sectional view, taken along lines X-X and looking in the direction of the arrows, of the multi-piece construct of FIG. 17.

Referring now to FIGS. 15, 17 and 18, the base member 222 is formed in a cylindrical shape, and is constructed of mineralized cancellous bone. Alternatively, a surface and/or portion of the base member 222 may be demineralized, as discussed above in connection with the construct 20 illustrated in FIGS. 2-12. The base member 222 includes an upper annular edge 230 and a blind bore 231 contained therein. The blind bore 231 contains a cylindrical island 232 that is formed concentrically with respect to the upper annular edge 230. An annular recess 234 is formed within the bore 231 between the cylindrical island 232 and an inner wall 236 of the base member 222, adjacent the upper annular edge 230. An upper surface 238 of the island 232 lies parallel to and below a horizontal plane defined by the upper annular edge 230. The base member 222 also includes first and second transverse bores 239, 240 in opposite sides of the inner wall 236 that extend through to an exterior surface of the base member 222, and are coaxial with each other. The island 232 also includes a through-going transverse bore 241 that is axially aligned with the transverse bores 239, 240.

Figure 16:
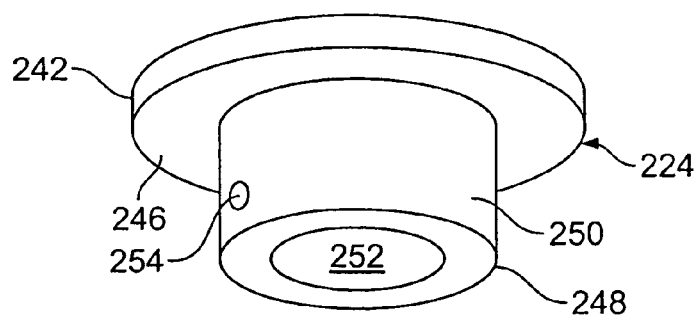
FIG. 16 is a bottom perspective view of a cap member employed by the multi-piece construct of in FIG. 15.

Referring to FIGS. 15, 16 and 17, the cap member 224 of the construct 220 includes a disc-shaped upper section 242 having an upper surface 244, a lower surface 246 and an integral sleeve-like cylindrical stem 248 which depends from the lower surface 246. The cap member 224 is formed of demineralized allograft cancellous bone having a calcium content less than 0.5% w/w residual calcium. The demineralization process described above may also be employed in connection with this embodiment.

In an alternative embodiment, the cap member 224 may have a mineralized region, such as the sleeve-like stem 248, and a demineralized region, such as the upper section 242. This alternative configuration enables the mineralized sleeve-like stem 248 to act as a rigid (e.g., non-spongy) core within the annular recess 234 of the base member 222 to provide further support for the load bearing of the joint.

With reference to FIGS. 15, 16 and 18, the sleeve-like stem 248 includes a wall 250 with inner and outer diameters D1, D2, respectively, and a cylindrical cavity 252 contained in the wall 250. The inner wall diameter D1 is slightly larger than the diameter of the island 232. Further, the depth of the cylindrical cavity 252 is approximately equal to the height of the island 232, so that the island 232 may be received therein. Moreover, the annular recess 234 of the base member 222 has a diameter that is slightly larger than the stem wall outer diameter D2, so as to receive the sleeve-like stem 248 therein.

As illustrated in FIGS. 17 and 18, the cap member 224 is placed on top of the base member 222 with the sleeve-like stem 248 being inserted into the annular recess 234 of the base member 222, and the island 232 being simultaneously inserted into the cylindrical cavity 252 of the cap member 224. Once the base member 222 and the cap member 224 have been assembled, the lower surface 246 of the upper section 242 of the cap member 224 abuts the upper annular edge 230 of the base member 222. The base member 222 and the cap member 224 may be dimensioned so that a minimal amount of open space is contained within the cylindrical cavity 252 and the annular recess 234. This structural arrangement provides a more solid support for load bearing of the joint.

In another embodiment of the construct 220, the base member 222 includes a plurality of through-going bores (not shown) formed in the in the upper annular edge 230, in the upper surface 238 of the island 236, or in both. The plurality of through-going bores in the construct 220 may facilitate blood migration throughout the construct 220, to promote cartilage growth in the cap member 224 and in the adjacent cartilage, and bone growth in the base member 222 and the adjacent bone, as described above in connection with the construct 20.

Referring again to FIGS. 15-18, the stem wall 250 includes two transverse bores 254, 256 formed in opposite sides thereof. After placing the cap member 224 on the base member 222, the transverse bores 254, 256, which are coaxial, may be aligned with the transverse bores 239, 240 of the base member 222, and with the transverse bore 241 of the island 232, to receive the cylindrical pins 226, 228 therein, and to hold the cap member 224 in place within the base member 222, thereby securing the cap member 224 to the base member 222. The pin 226 is inserted through the transverse bores 239, 254 and 241 (on one side of the base member 222), and the pin 228 is inserted through the transverse bores 240, 256 and 241 (on an opposite side of the base member 222) until the adjacent ends of each of the pins 226, 228 abut each other in the approximate center of the transverse bore 241 of the island 232 (see FIG. 18). The cap member 224 may also be secured to the base member 222 by a staple, a suture, a press-fit or an adhesive compound such as fibrin-based glue.

The assembled construct 220 is placed within a bore to replace an excised cartilage defect in a similar manner as that described above for the construct 20. The height of the construct 220 may determine its placement in a bore formed in the defect area of a patient, and, hence, the position of the upper surface 244 of the cap member 224 in relation to surface of the patient's adjacent articular cartilage. The construct 220 may be placed in the bore so that the upper surface 244 is substantially flush with the surface of the patient's adjacent articular cartilage to form a smooth, continuous load-bearing surface. A bottom end of the base member 222 may be supported by a bottom surface of the bore. Alternatively, the construct 220 may be placed so that the upper surface 244 is slightly higher than the surface of the adjacent cartilage, so as to be proud in relation thereto. The construct 220 may also be placed so that the upper surface 244 is slightly lower than the surface of the adjacent cartilage, thereby providing a space, or pocket, for tissue growth therewithin. A cartilage particle mixture may also be placed in such space or pocket. The cartilage particle mixture promotes chondrocyte (and/or other cellular) migration into (i.e., from the adjacent cartilage), attachment and proliferation in the bore, and enhances tissue integration between the cap member 224 and the adjacent articular cartilage. The cartilage particle mixture, which may contain freeze-milled cartilage particles, can be in the form of a paste or gel, and is described in greater detail below.

The construct 220 may have a diameter that is substantially equal to the diameter of the bore, in order to create an interference fit therebetween (e.g., an interference fit with the sidewall of the bore). Alternatively, the construct 220 may have a diameter that is larger than the diameter of the bore, in order to create a press-fit therein. Any of the suitable organic glue materials described above may be used to keep the construct 220 fixed in place in the bore.

The construct 220 may also be loaded with the aforementioned cartilage particle mixture and/or one or more of the additives described herein in connection with the other embodiments of the construct. Demineralized bone matrix, growth factors, cells grown outside of the patient's body and/or one or more of the other biological substances described herein may also be incorporated into the construct 220.

FIGS. 19-23 illustrate another embodiment of a construct 310 that may be formed by milling a cancellous bone cylinder into an unbalanced barbell-shaped body 312 including a cap member 314 having a lower annular edge 315 and an upper surface 317, a cylindrical stem 316, and a cylindrical base member 318 having an upper annular edge 319. In one embodiment, the cap member 314, stem 316 and base member 318 are integrally formed as one piece. The cap member 314 is demineralized according to the method discussed above, while the stem 316 and the base member 318 remain mineralized. At least some of the modifications in the dimensions and the surgical insertion of the construct 20 described above may be made in connection with the construct 310 as well. This embodiment is also disclosed in U.S. patent application Ser. No. 12/043,001 filed Mar. 5, 2008 and in U.S. Provisional Patent Application Ser. No. 60/904,809 filed Mar. 6, 2007, both of which are incorporated by reference herein in their entirety.

The diameter of the assembled construct 310, and of the cap member 314 and the base member 318, may be within a range from about 5 mm to about 35 mm. The stem 316 preferably has a diameter that is approximately half as large as the diameter of the base member 318. The cap member 314 is milled to have a height, or thickness, that is similar to the thickness of human articular cartilage (e.g., approximately 3 mm). In this embodiment, the base member 318 has a height that is greater than that of the cap member 314, with a ratio that is preferably in a range from about 3:2 to about 6:1.

Reference is now made to FIG. 21, which illustrates a ring-shaped member 320 that includes an aperture 322 having a diameter approximately equal to the diameter of the stem 316. Alternatively, the aperture 322 may have a diameter that is slightly greater than the diameter of the stem 316. The diameter of the aperture 322 may alternatively be within a range of from 10% to 40% larger than the diameter of the stem 316. The ring-shaped member 320 has an outer diameter that is approximately equal to the diameter of the cap member 314 and to the diameter of the base member 318. The ring-shaped member 320 also includes upper and lower surfaces 324, 326, respectively.

The ring-shaped member 320 is preferably constructed of mineralized allograft cancellous bone. Alternatively, the ring-shaped member 320 may be constructed of partially demineralized cancellous bone (e.g., wherein the demineralization processing of the cancellous bone of the ring-shaped member is abbreviated). The ring-shaped member 320 may be also constructed of allograft cortical bone or xenograft bone, as long as the same have been decellularized. The ring-shaped member 320 may also be constructed of ceramics or one or more known biocompatible polymers.

Prior to assembly, the cap member 314 may be demineralized by placing it in dilute acid (e.g., 0.6N HCl) according to the protocol discussed above until the bone contains less than 0.5% w/w residual calcium. The stem 316 and base member 318 are kept out of the dilute acid and remain mineralized, as indicated by a line L1 in FIG. 23. The demineralized bone of the cap member 314 is predominantly Type I collagen, which is sponge-like, elastic and deformable.

Following demineralization, the cap member 314 may be further cleaned and treated to restore its pH to a physiological level of about 7.0, as described above in connection with the construct 20. The demineralized cap member 314 may also be treated to reduce its osteoinductivity, or to render it substantially non-osteoinductive, as described above.

The spongy and deformable nature of the demineralized cap member 314 allows it to be deformed and inserted through the center aperture 322 of the ring member 320 during assembly of the construct 310. More particularly, the cap member 314 is deformed by compressing (i.e., squeezing) it to have a dimension smaller than the diameter of the center aperture 322. The cap member 314 is then inserted through the center aperture 322 in its compressed, smaller form. After being pushed through the center aperture 322, the cap member 314 is allowed to decompress, and then returns to its original shape and dimensions. Upon assembly of the ring-shaped member 320 and the base member 312, the lower surface 326 of the ring-shaped member 320 abuts the upper annular edge 319 of the base member 318, while the upper surface 324 of the ring-shaped member 320 abuts the lower annular edge 315 of the cap member 314. The assembled construct 310, as illustrated in FIGS. 19 and 22, includes a relatively uniform demineralized portion including the cap member 314, and a distinct mineralized portion including the base member 318 and the ring-shaped member 320. The ring-shaped member 320 serves as a uniform demarcation that physically divides the demineralized and mineralized portions of the assembled construct 310, whose two-piece construction eliminates the need to use one or more pins to secure the assembled construct components to each other.

After the construct 310 has been assembled, freeze-milled cartilage particles may be added to the cap member 314 in a manner similar to the method described in connection with the constructs disclosed above. The cartilage particles may be combined with a biocompatible carrier and/or a growth factor. The open cancellous structure of the cap member 314 may be loaded with cartilage particles and/or one or more other bioactive additives described herein. The construct 310 may also be infused with endogenous and/or exogenous growth factors, or endogenous growth factor activators, many of which are described herein.

The assembled construct 310 is placed within a bore to replace an excised cartilage defect in a similar manner as that described above for the construct 20. The height of the construct 310 may determine its placement in a bore formed in the defect area of a patient, and, hence, the position of the upper surface 317 in relation to surface of the patient's adjacent articular cartilage. The construct 310 may be placed in the bore so that the upper surface 317 of the cap member 314 is substantially flush with the surface of the patient's adjacent articular cartilage to form a smooth, continuous load-bearing surface. A bottom end of the base member 318 may be supported by a bottom surface of the bore. Alternatively, the construct 310 may be placed so that the upper surface 317 is slightly higher than the surface of the adjacent cartilage, so as to be proud in relation thereto. The construct 310 may also be placed so that the upper surface 317 is slightly lower than the surface of the adjacent cartilage, thereby providing a space, or pocket, for tissue growth therewithin. A cartilage particle mixture may also be placed in such space or pocket. The cartilage particle mixture promotes chondrocyte (and/or other cellular) migration into (i.e., from the adjacent cartilage), attachment and proliferation in the bore, and enhances tissue integration between the cap member 310 and the adjacent articular cartilage. The cartilage particle mixture, which may contain freeze-milled cartilage particles, can be in the form of a paste or gel, and is described in greater detail below.

The construct 310 may have a diameter that is substantially equal to the diameter of the bore, in order to create an interference fit therebetween (e.g., an interference fit with the sidewall of the bore). Alternatively, the construct 310 may have a diameter that is larger than the diameter of the bore, in order to create a press-fit therein. Any of the suitable organic glue materials described above may be used to keep the construct 310 fixed in place in the bore.

Figure 24:
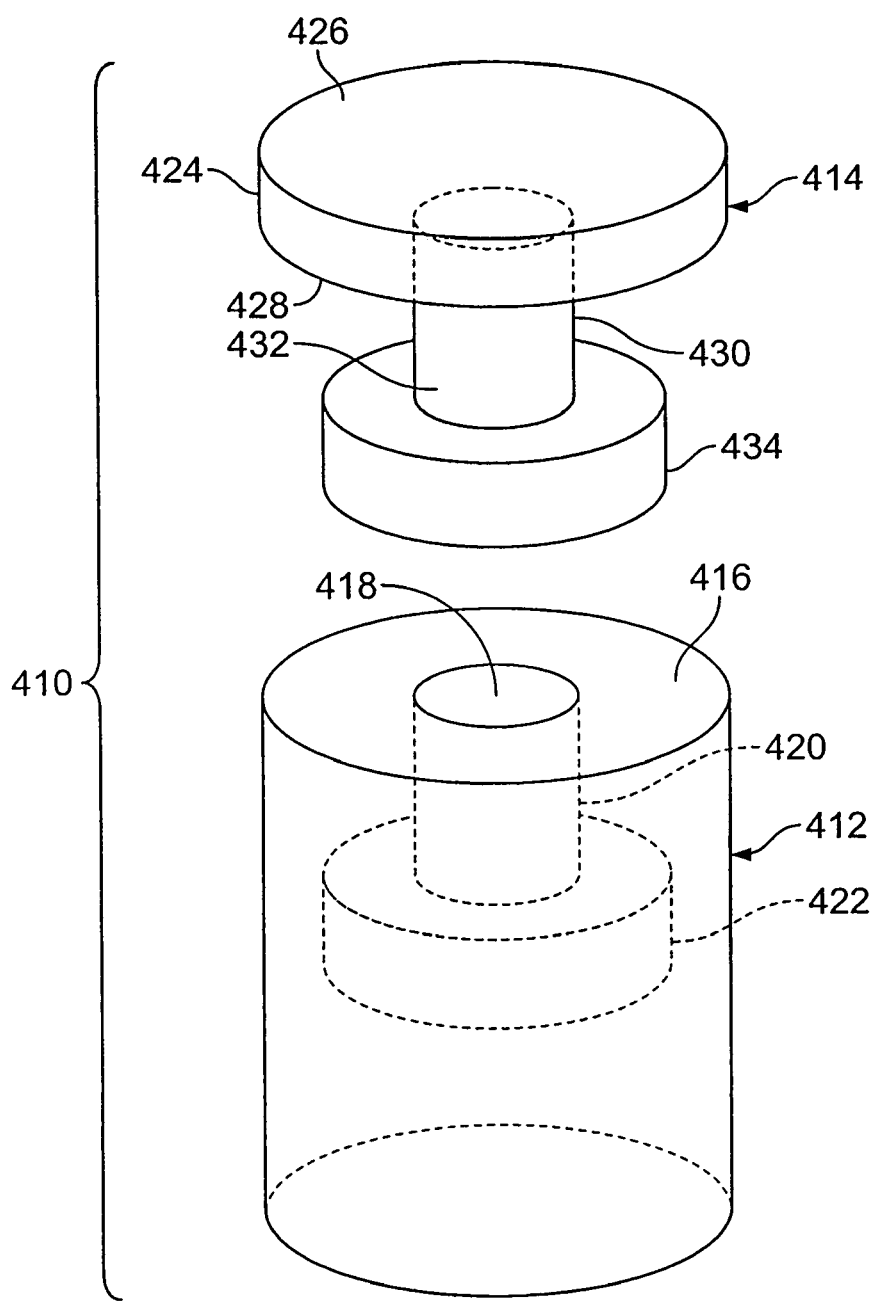
FIG. 24 is an exploded perspective view of a multi-piece cancellous construct produced in accordance with another embodiment of the present invention.
Figure 25:
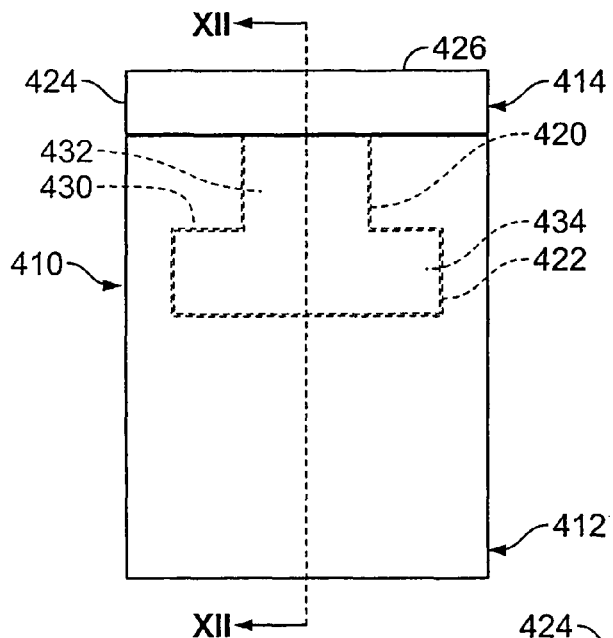
FIG. 25 is a side elevational view of the construct illustrated in FIG. 24, as assembled.
Figure 26:
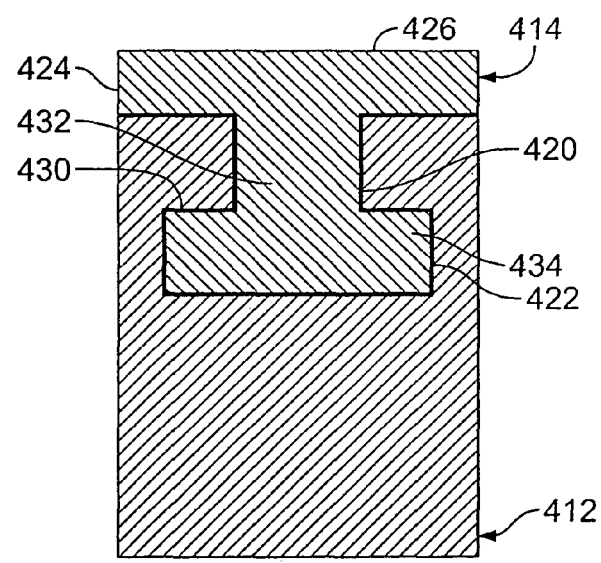
FIG. 26 is a cross-sectional view, taken along line XII-XII and looking in the direction of the arrows, of the construct illustrated in FIG. 25.

Reference is now made to FIGS. 24-26, which illustrate another embodiment of a construct 410 having a base member 412 and a cap member 414. At least some of the modifications in the dimensions and the surgical insertion of the construct 20 described above may be made in connection with the construct 410 as well.

The base member 412 is formed in a cylindrical shape, and is constructed of mineralized allograft cancellous bone. Alternatively, the base member 412 may be partially demineralized (as described above), and/or may contain a region of cortical bone. Because cortical bone is more dense and stronger than cancellous bone, including a region of cortical bone reinforces the base member 412, to provide the construct 410 with additional support for load bearing of the joint. The cortical bone of the base member 412 is preferably surface-demineralized (e.g., partially demineralized along its outer surface), which facilitates the incorporation of the construct 410 into the surrounding subchondral bone tissue.

The base member 412 includes an upper annular edge 416 and a blind bore 418, which extends into the base member 412. The blind bore 418 includes a cylindrical proximal portion 420 and an adjoining cylindrical distal portion 422 (e.g., the proximal and distal portions 420, 422 communicate with each other), wherein the terms "proximal" and "distal" are used in relation to an upper surface of the cap member 414, as discussed below. The diameter of the distal portion 422 of the blind bore 418 is greater than the diameter of the proximal portion 420, the purpose of which is discussed below.

With continued reference to FIGS. 24-26, the cap member 414 of the construct 410 includes a disc-shaped upper section 424 having upper and lower surfaces 426, 428, respectively, and an integral stem 430, which depends from the bottom surface 428. The cap member 414 is preferably formed of demineralized cancellous allograft bone. Demineralization of the cap member 414 may be performed using the method discussed above, such that the demineralized cancellous bone thereof has a residual calcium content less than 0.5% w/w.

The stem 430 includes a cylindrical proximal portion 432 and an adjoining cylindrical distal portion 434, wherein the terms "proximal" and "distal" are again used in relation to the upper surface 426 of the cap member 414. The diameter of the distal stem portion 434 is greater than the diameter of the proximal stem portion 432 (see FIG. 24). Moreover, the distal stem portion 434 is dimensioned so as to closely fit within the distal portion 422 of the blind bore 418 (i.e., the height and diameter of the distal stem portion 434 are slightly smaller than, or equal to, the height and diameter of the distal bore portion 422, respectively). Similarly, the proximal stem portion 432 is dimensioned to closely fit within the proximal portion 420 of the blind bore 418 (i.e., the height and diameter of the proximal stem portion 432 are slightly smaller than, or equal to, the height and diameter of the proximal bore portion 420, respectively). These relative dimensions are selected so as to facilitate the secure interconnection of the base and cap members 412, 414, as discussed below.

Once the cap member 414 has been demineralized, it is spongy and deformable with shape memory properties, thereby allowing the distal stem portion 434 thereof to be squeezed through the proximal bore portion 420 to assemble the construct 410. More particularly, the distal stem portion 434 is deformed by compressing it to have a dimension smaller than the diameter of the proximal bore portion 420 of the base member 412. The distal stem portion 434 is then inserted through the proximal bore portion 420 in its compressed, smaller form. After being pushed through the proximal bore portion 420 and into the distal bore portion 422, the distal stem portion 434 is allowed to decompress, whereupon it returns to its original shape and dimensions and conforms to the distal bore portion 422 (see FIGS. 25 and 26). The distal stem portion 434 is thereby locked into place within the distal bore portion 422, resisting movement in the proximal direction through the proximal bore portion 420 because the diameter of the proximal bore portion 420 is smaller than the diameter of the distal stem portion 434. Upon assembly, the base and cap members 412, 414 afford a well-defined, uniform separation between the respective mineralized and demineralized portions of the construct 410, as illustrated in FIGS. 25 and 26. More particularly, the assembled construct 410 includes a relatively uniform demineralized portion including the cap member 414, and a distinct mineralized portion including the base member 412, thereby physically dividing the demineralized and mineralized portions of the assembled construct 410. The interconnecting base member 412 and cap member 414 also eliminate the need to use one or more pins to secure the assembled construct components to each other.

The assembled construct 410 is placed within a bore to replace an excised cartilage defect in a similar manner as that described above for the construct 20. The height of the construct 410 may determine its placement in a bore formed in the defect area of a patient, and, hence, the position of the upper surface 426 in relation to surface of the patient's adjacent articular cartilage. The construct 410 may be placed in the bore so that the upper surface 426 of the cap member upper section 424 is substantially flush with the surface of the patient's adjacent articular cartilage to form a smooth, continuous load-bearing surface. A bottom end of the base member 412 may be supported by a bottom surface of the bore. Alternatively, the construct 410 may be placed so that the upper surface 426 is slightly higher than the surface of the adjacent cartilage, so as to be proud in relation thereto. The construct 410 may also be placed so that the upper surface 426 is slightly lower than the surface of the adjacent cartilage, thereby providing a space, or pocket, for tissue growth therewithin. A cartilage particle mixture may also be placed in such space or pocket. The cartilage particle mixture promotes chondrocyte (and/or other cellular) migration into (i.e., from the adjacent cartilage), attachment and proliferation in the bore, and enhances tissue integration between the cap member 414 and the adjacent articular cartilage. The cartilage particle mixture, which may contain freeze-milled cartilage particles, can be in the form of a paste or gel, and is described in greater detail below.

The construct 410 may have a diameter that is substantially equal to the diameter of the bore, in order to create an interference fit therebetween (e.g., an interference fit with the sidewall of the bore). Alternatively, the construct 410 may have a diameter that is larger than the diameter of the bore, in order to create a press-fit therein. Any of the suitable organic glue materials described above may be used to keep the construct 410 fixed in place in the bore.

The construct 410 may also be loaded with the cartilage paste and/or one or more of the additives described herein. Demineralized bone matrix, growth factors, cells and/or one or more of the other biological substances described herein may also be incorporated into the construct 410.

Figure 27:
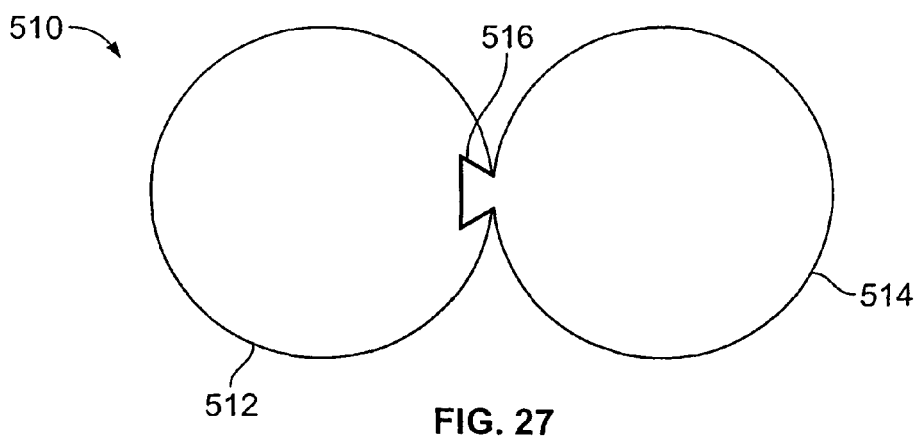
FIG. 27 is a schematic illustration of an assembly of multiple cancellous constructs produced in accordance with another embodiment of the present invention.

Reference is now made to FIG. 27, which illustrates another embodiment according to the present invention as an assembly 510 of two interconnected constructs 512 and 514. The individual constructs 512, 514 may be structurally similar to any of the constructs discussed herein. The constructs 512, 514 may be formed to interconnect in a dovetailed arrangement 516. Other types of connection arrangements are possible. The assembly 510 may include more than two individual construct, and may be used to repair large and/or irregularly-shaped (e.g., elongate) articular cartilage defects.

Figure 28:
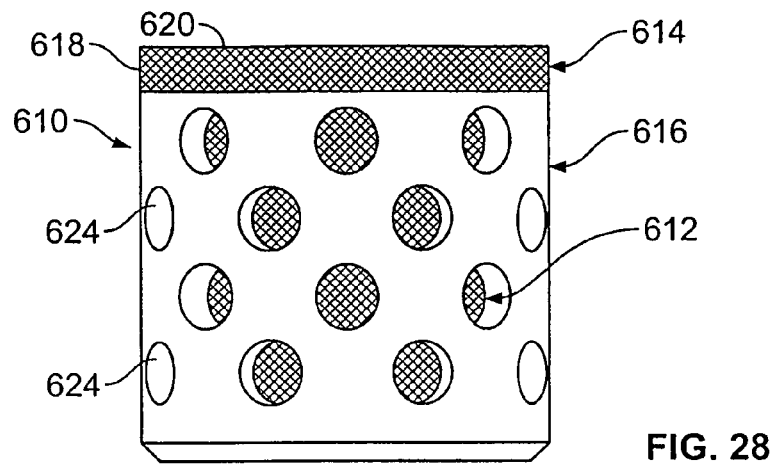
FIG. 28 is side elevational view of a multi-piece cancellous construct produced in accordance with another embodiment of the present invention.
Figure 29:
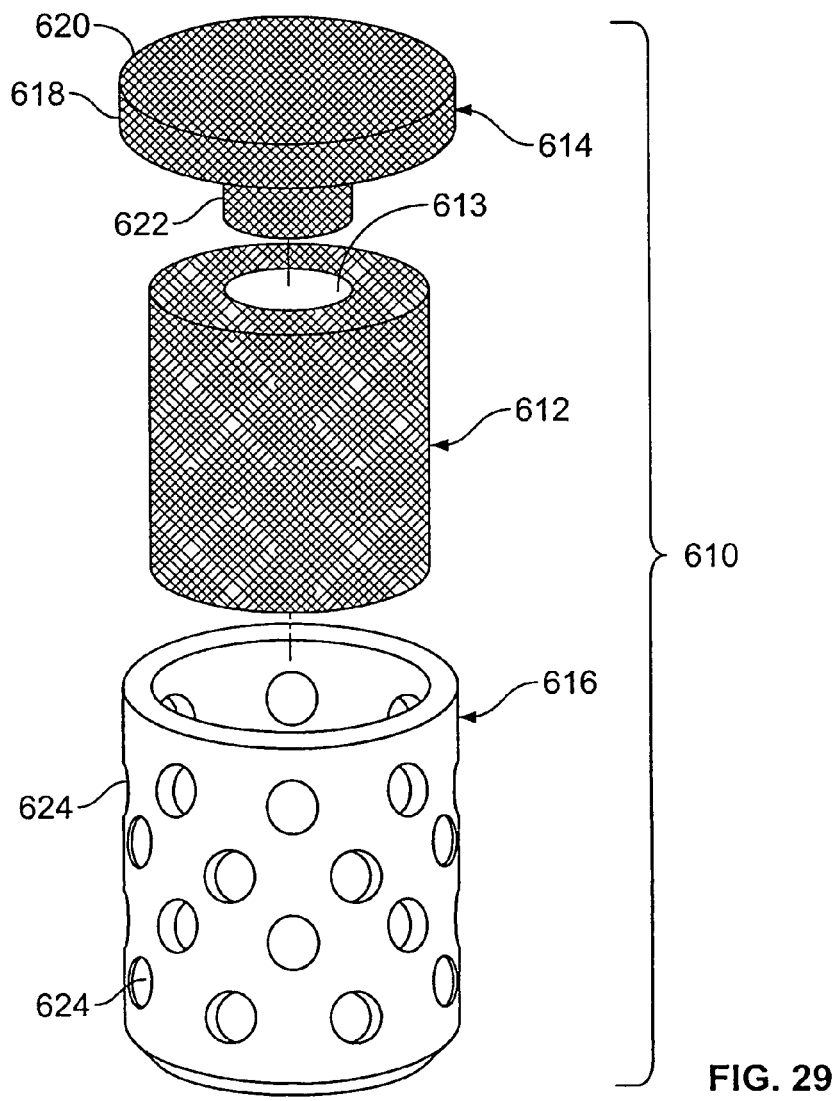
FIG. 29 is an exploded perspective view of the construct illustrated in FIG. 28.

Reference is now made to FIGS. 28 and 29, which illustrate another embodiment of a construct 610 including a base member 612, a cap member 614 and a sleeve member 616. At least some of the modifications in the dimensions and the surgical insertion of the construct 20 described above may be made in connection with the construct 610 as well.

The base member 612 is formed in a cylindrical shape, and includes a blind bore 613. The base member 612 is constructed of mineralized cancellous bone. The cap member 614 includes a disc-shaped upper section 618 having an upper surface 620 and a lower surface (not shown), and an integral stem 622 which depends from the lower surface of the upper section 618 (see FIG. 29). The cap member 614 is formed of demineralized cancellous allograft bone. Demineralization of the cap member 614 may be performed using the method discussed above, such that the demineralized cancellous bone thereof has a residual calcium content less than 0.5% w/w.

With continued reference to FIGS. 28 and 29, the sleeve member 616 is formed of cortical bone. Because cortical bone is more dense and stronger than cancellous bone, the sleeve member 616 reinforces the base member 612, to provide the construct 610 with additional support for load bearing of the joint. The cortical bone of the sleeve member 616 is preferably surface-demineralized (e.g., partially demineralized along its outer surface), which facilitates the incorporation of the construct 610 into the surrounding subchondral bone tissue, as discussed above in connection with corresponding components of the other embodiments of the construct. The sleeve member 616 includes a plurality of apertures 624 formed therein to facilitate the flow of blood and other physiological fluids towards the base member 612 after the construct 610 has been implanted.

The assembled construct 610 is placed within a bore to replace an excised cartilage defect in a similar manner as that described above for the construct 20. The height of the construct 610 may determine its placement in a bore formed in the defect area of a patient, and, hence, the position of the upper surface 620 of the upper section 618 in relation to surface of the patient's adjacent articular cartilage. The construct 610 may be placed in the bore so that the upper surface 620 is substantially flush with the surface of the patient's adjacent articular cartilage to form a smooth, continuous load-bearing surface. A bottom end of the base member 612 may be supported by a bottom surface of the bore. Alternatively, the construct 610 may be placed so that the upper surface 620 is slightly higher than the surface of the adjacent cartilage, so as to be proud in relation thereto. The construct 610 may also be placed so that the upper surface 620 is slightly lower than the surface of the adjacent cartilage, thereby providing a space, or pocket, for tissue growth therewithin. A cartilage particle mixture may also be placed in such space or pocket. The cartilage particle mixture promotes chondrocyte (and/or other cellular) migration into (i.e., from the adjacent cartilage), attachment and proliferation in the bore, and enhances tissue integration between the cap member 614 and the adjacent articular cartilage. The cartilage particle mixture, which may contain freeze-milled cartilage particles, can be in the form of a paste or gel, and is described in greater detail below.

The construct 610 may have a diameter that is substantially equal to the diameter of the bore, in order to create an interference fit therebetween (e.g., an interference fit with the sidewall of the bore). Alternatively, the construct 610 may have a diameter that is larger than the diameter of the bore, in order to create a press-fit therein. Any of the suitable organic glue materials described above may be used to keep the construct 610 fixed in place in the bore. The cap member 614 may be secured to the base member 616 by one or more pins, as described in connection with the above constructs, and/or by use of a staple, a suture, a press-fit or an adhesive compound such as fibrin-based glue.

The construct 610 may also be loaded with the cartilage paste and/or one or more of the additives described herein. Demineralized bone matrix, growth factors, cells and/or one or more of the other biological substances described herein may also be incorporated into the construct 610.

Figure 30:
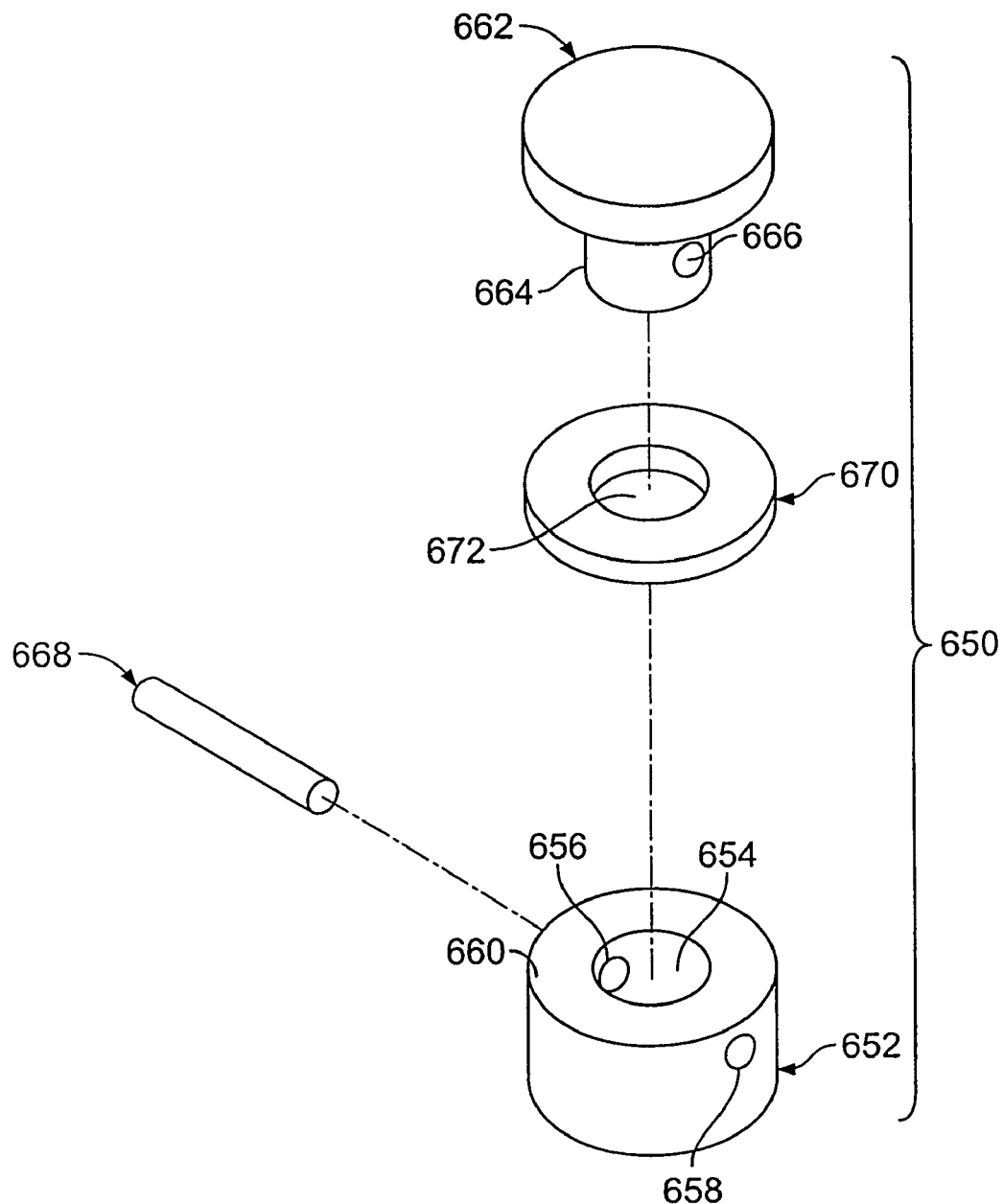
FIG. 30 is an exploded perspective view of a multi-piece cancellous construct produced in accordance with another embodiment of the present invention.

Another embodiment of a multi-piece cancellous construct 650 is illustrated in FIG. 30. At least some of the modifications in the dimensions and the surgical insertion of the construct 20 described above may be made in connection with the construct 650 as well.

The construct 650 includes a base member 652 having a blind bore 654, a pair of coaxial, transverse through-going bores 656, 658, and an upper annular edge 660. The construct 650 also includes a cap member 662 having a stem 664 with a transverse through-going bore 666 therein, and a pin 670. The base member 652, cap member 662 and pin 668 are constructed in the same manner and from the same materials as the base member 22, cap member 30 and pin 40 respectively, of the construct 20 illustrated in FIGS. 2-12, and are assembled in substantially the same way in relation to each other. In addition, the construct 650 includes an annular support member 670 having a central opening 672 therein. In one embodiment, the annular support member 670 is made of cortical bone, which may be partially and/or surface-demineralized. The annular support member 670 may also be made of one or more synthetic materials.

The annular support member 670 may be in the form of a ring structure or washer, and is inserted between the cap member 662 and the base member 652, so as to abut the upper annular surface 660 of the base member 652 and a lower surface of the cap member 662 (i.e., a lower annular surface of the cap member 662 adjacent the stem 664). The annular support member 670 provides additional support to the construct 650. The annular support member 670 may include holes cut through multiple planes thereof.

Upon assembly of the construct 650, the stem 664 of the cap member 662 is inserted through the central opening 672 of the annular support member 670 into the blind bore 654 of the base member 652. The stem 664 may be arranged so that the transverse through-going bores 656, 658 of the base member 652 and the transverse through-going bore 666 of the stem 664 are axially aligned to receive the pin 670 therein. The pin is inserted into the transverse through-going bores 656, 658 of the base member 652 and through the transverse through-going bore 666 of the stem 664, so as to secure the cap member 662 to the base member 652, and to secure the annular support member 670 between the cap member 662 and the base member 652.

In another embodiment, a construct includes a base member formed of cancellous and cortical bone, with the cortical bone portion reinforcing the base member to provide the construct with additional support for load bearing of the joint. For example, the cortical bone portion may form a core of the base member, with a surrounding, outer portion thereof formed of cancellous bone. Other components and/or portions of the construct may also be constructed of cortical bone.

In another embodiment, a construct includes at least one component (e.g., a base member, a cap member or both) that has one or more synthetic support members. The synthetic support member is formed of one or more biocompatible materials. In an alternative embodiment, a construct includes a base member formed of cancellous bone and a cap member formed of a biocompatible, bioabsorbable synthetic material.

An alternative method according to the present invention involves the use of the constructs disclosed above for replacing one or more tissue plugs removed from non-load-bearing areas (or areas of lesser load-bearing) of the articular cartilage layer during an autologous transplant procedure (e.g., mosaicplasty or osteochondral allograft transfer system (OATS)). In other words, the constructs may be used in a "backfill" capacity to replace the healthy articular cartilage and underlying subchondral bone that has been removed from the non-load-bearing area of a patient's joint and implanted into a bore to repair a cartilage defect in the load-bearing area of the joint. Also, following a mosaicplasty procedure involving the implantation of multiple plugs of the patient's transplanted healthy articular cartilage tissue into the bore, small constructs may be inserted into the gaps formed in between the implanted tissue plugs to eliminate such gaps in the mosaicplasty site. Elimination of these gaps restores a more uniform articular cartilage surface at the defect repair site, which in turn enhances the load-bearing mechanical support at the site.

In the embodiments of the present invention that are discussed below, one-piece scaffold-like constructs are disclosed. The construct may be formed by cutting demineralized cancellous bone into disc-like or cylindrical shapes (as described below) using a biopsy punch, cork borer, or other boring tool. Alternatively, the bone may be cut into the desired shapes prior to demineralization. The bone may alternatively be cut to form constructs having other shapes, including rectangular, square, and oval configurations. Alternatively, a surgeon may be provided with the sheets or blocks of demineralized cancellous bone from which to cut the desired constructs during surgery.

The demineralized cancellous bone constructs may be freeze-dried for long-term storage. The constructs may also be terminally sterilized via gamma irradiation. Prior to usage, the construct may be re-hydrated in saline solution. The construct may also be inserted in a dry (i.e., lyophilized) state. Upon re-hydration, the construct will exhibit shape-memory and regain its original volumetric dimensions.

Figure 31:
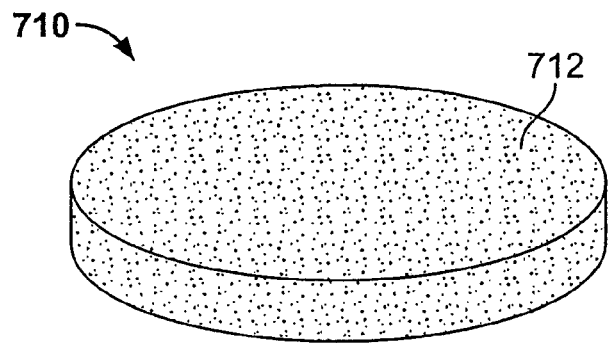
FIG. 31 is a top perspective view of a one-piece cancellous construct produced in accordance with another embodiment of the present invention.

An embodiment of the scaffold-like cartilage repair construct of the present invention is shown in FIG. 31 and designated by reference number 710. The construct 710 includes a disc 712 made of demineralized cancellous bone, which is sponge-like, elastic and deformable, as noted above. Demineralized cancellous bone is deformable, thereby facilitating insertion of the construct 710 into a cartilage defect, as well as the infusion of cartilage particles into the demineralized cancellous bone, and provides mechanical support at the defect site. As discussed above, the properties of cancellous bone (e.g., its porosity) enable it to act as a natural matrix for receiving and retaining therein a mixture containing cartilage particles and various bioactive chondrogenic materials for the repair of articular cartilage defects. Cancellous bone also acts as a conduit for tissue ingrowth and regeneration.

Still referring to FIG. 31, the disc 712 is dimensioned so as to replace damaged or diseased cartilage in the repair of cartilage thickness defects (the related surgical repair methods are described below). More particularly, the disc 712 has a thickness (or height) which is similar to that of the portion of the cartilage layer containing the damaged or diseased cartilage and the adjacent cartilage layer (e.g., within a range of about 1.5 mm to about 7 mm).

The disc 712 may be dimensioned so as to have a diameter which is approximately the same as that of a cartilage defect site, or a surgically-created bore formed to excise the damaged or diseased cartilage tissue. The disc 712 may be secured within the bore by an interference fit produced when the outer edges of the disc 712 abut the bore walls. The disc 712 may also or alternatively be secured within the bore using sutures, staples, pins and/or a bioadhesive glue, as described above in connection with the other construct embodiments disclosed herein. The arrangement of the disc 712 secured within the bore promotes load-bearing mechanical support at the bore.

Figure 32:
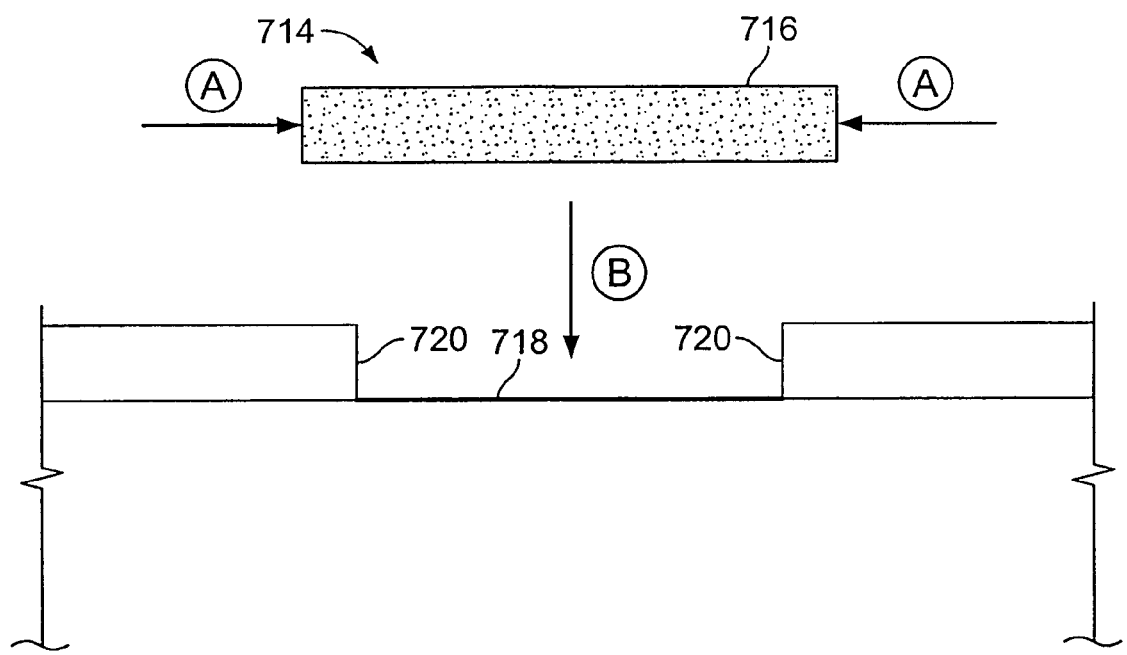
FIG. 32 is a schematic illustration of the one-piece construct of FIG. 31 as it is being inserted into a cartilage defect in accordance with a method performed in accordance with the present invention.

Another embodiment of a scaffold-like construct 714 is illustrated in FIG. 32. The construct 71 may be dimensioned so that it includes a disc 716 having a larger diameter than that of a bore 718 (e.g., up to 25% larger than the bore diameter). The disc 716 is made of demineralized cancellous bone, and is compressed along its horizontal plane (as shown by Arrows A) until a dimension of the disc 716 (e.g., diameter, width, etc.) is smaller than the corresponding dimension of the bore 718. The compressed disc 716 is inserted into the bore 718 (as shown by Arrow B) and the compressive force is removed so that the disc 716 expands outwardly until the outer edges of the disc 716 abut the walls 720 of the bore 718, producing a secure press fit between the compressed disc 716 and the bore walls 720. This arrangement also promotes load-bearing mechanical support at the bore 718.

Multiple cartilage repair constructs may be used to treat a large cartilage defect. More particularly, two or more of the constructs discussed above may be arranged adjacent each other within a bore to repair a large cartilage defect. For example, two or more constructs may be arranged side-by-side, or top-to-bottom (e.g., one on top of the other). These constructs are tightly packed together within the bore in order to fill the bore and secure the constructs therein.

Figure 33C:
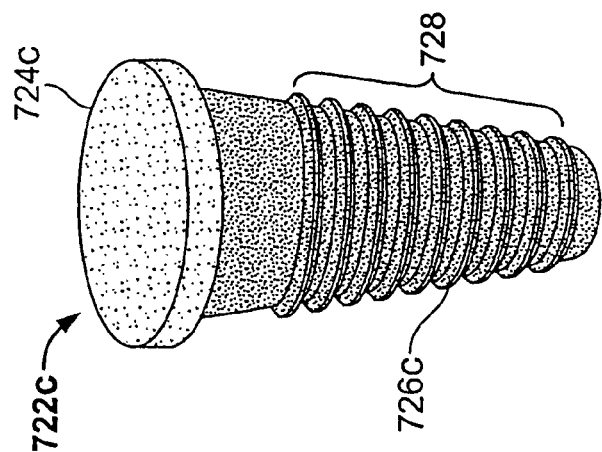
FIGS. 33A, 33B and 33C are top perspective views of three embodiments of a one-piece cancellous construct produced in accordance with another embodiment of the present invention.
Figure 33B:
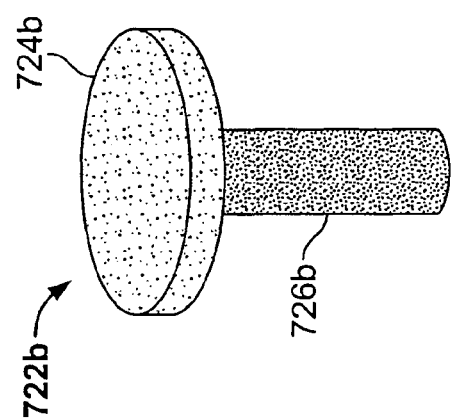
Figure 33A:
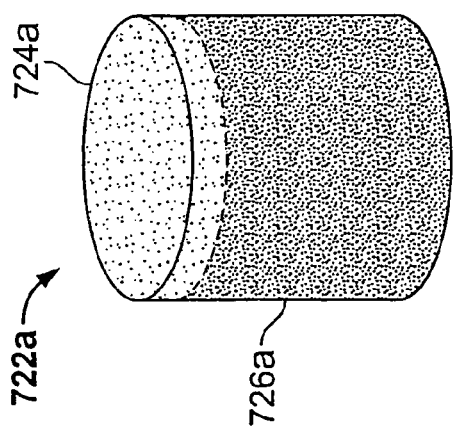

Reference is now made to FIGS. 33A, 33B and 33C, which illustrate three other embodiments in the form of integral one-piece, two-phase constructs. These two-phase constructs are used when a portion of the patient's subchondral bone adjacent the cartilage defect is also surgically removed, resulting in the need to replace both the excised layer of cartilage and the underlying subchondral bone. Each of these two-phase constructs is discussed individually below.

Referring to FIG. 33A, an integral (e.g., one-piece) two-phase construct 722a is illustrated. The construct 722a includes a demineralized cancellous bone cap 724a and a mineralized cancellous bone base 726a. The cap 724a has a thickness that is similar to that of a patient's adjacent cartilage layer (e.g., in a range of from about 1.5 mm to about 7 mm). The base 726a may have a height equal to the depth of the subchondral bone portion of the bore. Alternatively, the base 726a may be shorter than the depth of the subchondral bone portion of the bore. The cap 724a and the base 726a have the same diameter. The base 726a retains its osteoinductive properties, and may therefore be secured within the subchondral bone adjacent the cartilage defect, for the purpose of anchoring the construct 722a in the subchondral bone.

Reference is now made to FIG. 33B, which illustrates another integral two-phase construct 722b that includes a demineralized cancellous bone cap 724b and a mineralized cancellous bone base 726b. The cap 724b has a thickness matching that is similar to that of a patient's adjacent cartilage layer (e.g., in a range of from about 1.5 mm to about 7 mm). The base 726b may have a height equal to the depth of the subchondral bone portion of the bore. Alternatively, the base 726b may be shorter than the depth of the subchondral bone portion of the bore. The base 726b has a smaller diameter than that of the cap 724b, which necessitates the removal of less subchondral bone during implantation surgery. The base 726b also retains its osteoinductive properties, and may therefore be secured within the subchondral bone adjacent the cartilage defect for the purpose of anchoring the two-phase construct 722b in the subchondral bone.

In another embodiment, the base 726b can be constructed of demineralized cancellous bone. A surgeon may be able to compress the base 726b to facilitate its insertion into a bore, in an operation similar to that disclosed above in connection with the construct 714 illustrated in FIG. 32.

In another embodiment, the two-phase construct 722b may include two or more (i.e., multiple) bases 726b (not shown) depending from the cap 724b. The multiple bases 726b may be inserted into a corresponding number of bores formed in a defect area or areas in a patient's tissue (i.e., articular cartilage and adjacent subchondral bone) to repair an osteochondral defect. A surgeon may form the multiple bores in the patient's tissue by using a template with openings that correspond in number, size and position to the multiple bases 726b. Alternatively, a surgeon may form the multiple bores using a punch having a pattern that corresponds in number, size and position to the multiple bases 726b.

Reference is now made to FIG. 33C, which illustrates another integral two-phase construct 722c. The construct 722c includes a demineralized cancellous bone cap 724c and a mineralized cancellous bone base 726c. The cap 724c has a thickness similar to that of the adjacent cartilage layer (e.g., in a range of from about 1.5 mm to about 7 mm). The base 726c may have a height approximately matching the depth of the subchondral bone portion of the bore. Alternatively, the base 726c may be shorter than the depth of the subchondral bone portion of the bore. The base 726c has a smaller diameter than that of the cap 724c, which necessitates the removal of less subchondral bone during implantation surgery. Further, the base 726c is tapered, and is formed to include a thread 728 for facilitating the implantation and the secure fit of the base 726c within the subchondral bone portion of the bore. As with the other two-phase constructs disclosed above, the base 726c retains its osteoinductive properties, and may therefore be secured within the subchondral bone adjacent the cartilage defect for the purpose of anchoring the construct 722c in the subchondral bone.

Any of the constructs disclosed above or any portion(s) thereof (e.g., the demineralized portion of the constructs) may be supplemented with at least one bioactive component such as a mixture including freeze-milled allograft cartilage (e.g., particulate cartilage), as disclosed herein, as well as exogenous and/or endogenous growth factors and/or endogenous growth factor activators and allogenic or autologous cells. The cartilage particle mixture may be in the form of a paste or a gel, as described herein.

The cartilage particle mixture may be injected into the construct and/or spread onto each surface of the construct. A spatula, or similar instrument, may be used to spread the cartilage particle mixture onto the construct surfaces and press the mixture into the construct openings, thereby facilitating the incorporation of cartilage particles into the construct. Alternatively, the cartilage particle mixture may only be added to the upper surface of the construct to form a distinct surface layer.

The two-phase constructs discussed above may also be modified to include regionally-specific chondrogenic and osteogenic regions in the respective caps and bases. More particularly, the cap (724a, 724b or 724c) of the construct may incorporate a cartilage particle mixture and/or chondrogenic growth factors, and the base (726a, 726b or 726c) of the construct may incorporate demineralized bone matrix and/or osteogenic growth factors.

The following operation may be used to perform a surgical repair of a cartilage defect using a single-phase demineralized bone construct (such as those illustrated in FIGS. 31 and 32). The surgeon debrides the damaged or diseased portion of cartilage from an articular cartilage surface, and creates a defect site, bore (i.e., a depression or divot) in this surface. In the embodiments of the construct discussed above, the bore is shaped into a cylinder or disc by boring through the cartilage immediately surrounding the debrided cartilage. Based on the patient's anatomy and the extent of tissue damage or disease, a surgeon determines the specific dimensions of the bore (e.g., depth and diameter). The subchondral bone that is exposed by the creation of the bore may then be subjected to a microfracture procedure, whereby the surgeon uses an awl to create a number of small portals in the surface of the subchondral bone, causing it to bleed into the bore.

Next, the surgeon may modify the size and/or shape of the construct for implantation into the bore. For example, the surgeon may chamfer the lower end of the base of the construct to facilitate insertion of the construct into the bore.

The single-phase construct is then implanted in the bore in a dry (i.e., lyophilized) state. An inserter device may be used to place the construct within the bore. In order to expedite this step, the surgeon may be provided with an inserter device in which the construct has been removably secured prior to surgery.

The height of the aforesaid single-phase construct is approximately the same as the thickness of the cartilage layer removed to create the bore (e.g., the depth of the bore). The construct is preferably positioned such that its upper surface is substantially flush with the surface of the adjacent cartilage of the articulating joint. Alternatively, the construct may be placed to be proud or slightly higher than the adjacent cartilage. The construct may also be placed so that the upper surface is slightly lower than the adjacent cartilage, which provides space for tissue growth between the construct and the cartilage surface.

If the construct has a larger dimension (e.g., diameter, width, etc.) than the corresponding dimension of the bore (see above and FIG. 32), the construct is compressed so as to decrease such dimension until it is smaller than the bore dimension. The compressed construct is then inserted into the bore, after which the compressive force is removed, and the construct expands within the bore until its outer edges abut the bore walls to produce a secure press fit between the compressed construct and the bore walls.

Shortly after implantation, blood from the microfractured subchondral bone flows into the pores of the construct, rehydrating and expanding the construct so that it is locked into place within the bore. Various adhesive materials may be used to better secure the construct within the bore and entrap blood from the bleeding bone within the construct. Such adhesive materials include, for example, suitable organic glue materials that can be found commercially, including fibrin-based sealants derived from human and/or bovine plasma, such as TISSEEL® (Baxter International, Inc., USA), CROSSEAL® (Johnson & Johnson, USA) and BIOGLUE® (Cryolife, Inc., USA); a fibrin-based adhesive, such as TISSUCOL® (Immuno AG, Austria), Adhesive Protein (Sigma Chemical, USA), Dow Corning Medical Adhesive B (Dow Corning, USA); a tissue adhesive consisting of collagen-derived particles and topical thrombin, such as FLOSEAL® (Baxter International, Inc.); a combination of polyethylene glycol polymers that have the ability to chemically bond to each other, as well as to tissue surfaces, such as COSEAL® (Angiodevice International GMBH Corporation, Switzerland); fibrinogen thrombin, elastin, collagen, casein, albumin, keratin, and/or adhesive compounds and/or organic glues and the like.

Affixation means such as, for example, sutures, staples and/or screws may also be used to better secure the construct within the bore and entrap blood from the bleeding bone within the construct post-implantation. The construct may also be press-fit within the bore.

The surgical repair of a cartilage defect using a two-phase construct (such as those illustrated in FIGS. 33A, 33B and 33C) may also be initiated by debriding the damaged or diseased portion of cartilage from an articular cartilage surface, and creating a defect site, or bore, in this surface. The bore is shaped into a cylinder or disc by boring through the cartilage immediately surrounding the debrided cartilage, and also boring into the subchondral bone beneath the cartilage defect. Based on the patient's anatomy and the extent of tissue damage or disease, a surgeon determines the specific dimensions of the bore (e.g., depth and diameter). Because the bore extends into the subchondral bone, no microfracture procedure is performed on the surface of the subchondral bone. However, the penetration of the subchondral bone causes bleeding, and the blood produced may also flow into the construct to rehydrate and expand it, thereby locking the construct in place within the bore.

The surgeon may then modify the size and/or shape of the two-phase construct for implantation into the bore. For example, the surgeon may trim a lower end of the bottom mineralized portion of one of the two-phase constructs (e.g., an end that is farthest from the top demineralized portion) to fit into a bore having a depth that is less than the height of the construct. The surgeon may also chamfer the lower end of the bottom mineralized portion to facilitate insertion into the bore. The construct is then implanted into the bore to occupy both the cartilage portion and the subchondral bone portion thereof.

The height of the cap portion of the two-phase construct is similar to the thickness of the cartilage layer removed to create the bore (e.g., the depth of the bore). The construct may be positioned such that the upper surface of the cap is substantially flush with the surface of the patient's adjacent cartilage to form a smooth, continuous load-bearing surface. Alternatively, the construct may be placed so that the upper surface slightly higher than the adjacent cartilage surface, so as to be proud in relation thereto. The construct may also be placed so that the upper surface is slightly lower than the adjacent cartilage, thereby providing a space, or pocket, for tissue growth therewithin. A cartilage particle mixture may also be placed in such space or pocket. The cartilage particle mixture promotes chondrocyte (and/or other cellular) migration into (i.e., from the adjacent cartilage), attachment and proliferation in the bore, and enhances tissue integration between the construct and the adjacent articular cartilage. The cartilage particle mixture, which may contain freeze-milled cartilage particles, can be in the form of a paste or gel, and is described in greater detail below.

The methods disclosed above may also include one or more steps of supplementing the construct with one or more of the bioactive components discussed herein. For example, prior to implantation of the construct, cartilage particle mixture may be injected into the construct and/or spread onto one or more surfaces of the construct. Any one or more of the other bioactive components discussed herein may also be added to the construct. The bioactive component(s) may be added to the construct in a hydrated or dehydrated state prior to insertion into the bore. The bioactive component(s) may also be added to the construct during implantation, or afterwards. Organic glues (such as those listed above) may be applied to the surface of the construct following implantation of supplemented constructs, in order to better retain the additional bioactive components.

Another method according to the present invention involves the use of the two-phase constructs disclosed above for replacing one or more tissue plugs removed from non-load-bearing areas (or areas of lesser load-bearing) of the articular cartilage layer during an autologous transplant procedure (e.g., mosaicplasty or osteochondral allograft transfer system (OATS)). In other words, the constructs may be used in a "backfill" capacity to replace the healthy articular cartilage and underlying subchondral bone which has been removed from the non-load-bearing area of a patient's joint and implanted into a bore to repair a cartilage defect in the load-bearing area of the joint. Moreover, following a mosaicplasty procedure involving the implantation of multiple plugs of the patient's transplanted healthy articular cartilage tissue into the bore, small constructs may be inserted into the gaps formed in between the implanted tissue plugs to eliminate such gaps in the mosaicplasty site. Elimination of these gaps restores a more uniform articular cartilage surface at the defect repair site, which in turn enhances the load-bearing mechanical support at the site.

The constructs described herein may be processed using any one or more of the processing methods described herein (e.g., demineralization methods, tissue cleaning, cartilage particle and/or paste forming and application methods, and/or any method of combining such constructs with cartilage paste and/or particle materials).

Cartilage Particles

In one embodiment, the cartilage particles described herein are administrable as a stand-alone therapeutic treatment.

In one embodiment, the cartilage particles described herein are milled allograft cartilage particles. In one embodiment, allograft cartilage particles are milled, e.g. by use of a freeze-milling (i.e., freezer-milling) process wherein the cartilage is cryogenically frozen, for example by use of a liquefied gas freezing agent (e.g., liquid nitrogen or liquid helium), and then ground into particles.

In one embodiment, a cartilage defect repair material includes the aforementioned freeze-milled cartilage particles.

In another embodiment, the cap member of a construct according to the present invention is infused with a mixture, such as a paste or gel, that includes freeze-milled allograft cartilage particles. In one embodiment, the term "gel" refers to a mixture of freeze-milled cartilage in a biocompatible carrier having a viscosity which is less than and is less rigid than a mixture of freeze-milled cartilage referred to by the terms "putty" or "paste", and contains less cartilage by weight than putty or paste. The cartilage paste or gel components are believed to provide the environmental and biochemical cues to elicit a healing response from the cells. For example, paste or gel components such as proteoglycans, collagen type II and other extracellular matrix components and their substituents may be present in greater concentration and/or bioavailability as a function of the processing of freeze-milled cartilage (e.g., freeze-milling the cartilage may result in cartilage particles that are characterized as having greater exposure/bioavailability of different cytokines, growth factors, etc. to the surrounding environment). These available factors may then exert effects on cells that have infiltrated the construct from the surrounding host tissue and bleeding bone, synovium, etc. In one embodiment, the cells are chondrocytes. In one embodiment, the cells are capable of differentiation into chondrocyte lineage. In one embodiment, the cells are mesenchymal stem cells. Further examples include, without limitation, pluripotent stem cells; progenitor cells; mesenchymal stem and progenitor cells; stromal cells; and cartilage stem cells.

The cartilage particles may be irregularly shaped, and are passed through a sieve having 212 micron (μm) openings. While at least one dimension of each of the particles will be 212 microns or smaller in order to fit through the sieve, certain other axis lengths of the same particles may be greater than 212 microns, rendering the particles unable to pass through the sieve openings in that particular orientation. Several differently-sized cartilage particles are described in U.S. Pat. No. 7,067,123, and in U.S. patent application Ser. Nos. 12/043,001; 11/657,042; 12/079,629; 10/960,960 and 60/996,800, all of which are fully incorporated by reference herein in their entirety.

In one embodiment, the cartilage particles have a size (i.e., the aforesaid at least one dimension) within a range of from about 10 microns to about 210 microns (i.e., from about 0.01 mm to about 0.21 mm). Alternatively, the cartilage particles may have a size (i.e., the aforesaid at least one dimension) that is within a range of from about 10 microns to about 120 micron (i.e., from about 0.01 mm to about 0.12 mm). The aforesaid at least one dimension of the cartilage particles may alternatively be less than or equal to 212 microns; within a range of from about 5 microns to about 212 microns; within a range of from about 6 microns to about 10 microns; less than or equal to 5 microns; less than or equal to 10 microns; or less than or equal to 100 microns. In one embodiment, the aforesaid at least one dimension of most of the particles is less than 100 microns. In another embodiment, the aforesaid at least one dimension of the cartilage particles has a mean and/or median value in the range of between 10 microns and 200 microns. The small size of the cartilage particles can facilitate the increased exposure of, or release of, various growth factors due to the increased aggregate surface area of the particulate cartilage used, and can increase the capacity of the surrounding and infiltrating cells to attach to the cartilage particles.

In another embodiment, the cartilage particle size may facilitate the stable infiltration of the porous, demineralized portion of the construct by the cartilage particles. In one embodiment, the cartilage particles are freeze-milled to a size that permits them to be inserted into and retained by the pores in the cancellous bone of the cap member while optimizing the packing density of the particles therein.

The porosity of the cap member and cartilage particle size and/or shape may synergistically facilitate retention of the cartilage particles within the construct. Other factors facilitating retention of the cartilage particles in the construct throughout a range of motion include, but are not limited to, construct porosity, cartilage particle size and/or shape, construct and/or cartilage particle co-administered agents, moisture content of the construct and/or cartilage particles, blood clotting processes in an area of bleeding bone or other tissue proximate to the inserted cartilage particles, and/or the degree to which the cap member is demineralized, which determines the relative conformability of the cap member.

Moreover, in one aspect of the invention the demineralized cancellous bone cap member acts as a porous scaffold and provides sufficient structural support to withstand subsequent mechanical loading. In another embodiment, the addition of the cartilage particles to the demineralized cap further increases the stiffness of the region so as to provide adequate stiffness to withstand loading. In another aspect of the invention, the demineralized cancellous bone cap is sufficiently conformable (with or without the addition of cartilage particles) so as to be insertable into a tissue defect without significant damage to surrounding or opposing tissues. In one embodiment, the pliability of the demineralized cancellous bone prevents damage to surrounding or opposing cartilage surfaces during loading and articulation, and allows the cap member to conform to the natural curvature of the joint surface.

The cartilage particle gel or paste provides the environment and necessary biochemical cues to elicit a healing response from the cells that have infiltrated the construct from the surrounding host tissue, synovium and/or bleeding bone that undergoes blood clotting and other reparative processes. In one embodiment, these biochemical cues include the exposure to, or release of, various growth factors, as discussed herein.

The cartilage particles are preferably derived from allograft cartilage, such as allograft articular cartilage. For example, such cartilage particles may be composed at least partially of collagen type II and proteoglycans, which may provide a non-cellular matrix to support cell attachment and to facilitate extracellular matrix production. The cartilage particles may also be derived from fibrous cartilage, or a combination of hyaline and fibrous cartilage. Alternatively, autograft or xenograft cartilage may be used.

In an alternative embodiment, a gel or paste containing fibrous tissue particles (e.g., derived from meniscus, tendons, ligaments, annulus of an intervertebral disc, etc.) may be used for repairing defects in fibrous tissues (e.g., meniscus, tendons, ligaments, annulus of an intervertebral disc etc.) For example, defects in a meniscus may be repaired using a paste mixture containing cartilage particles derived from meniscus tissues.

In another embodiment, any of a number of tissues (e.g. meniscus, tendons, ligaments, skin, fascia, periosteum, muscle, fat, nucleus pulposus of intervertebral disc etc.) may be freeze-milled and subsequently utilized in defect repair and/or genesis of similar or physiologically unrelated tissues.

The starting material from which the cartilage particles are derived may be lyophilized. In one embodiment, the starting material from which the cartilage particles are derived will have been lyophilized prior to freeze-milling, so that their water content may be within a range from 0.1% to 8.0%. In another embodiment, the cartilage particles resulting from the freeze-milling process may be lyophilized again (i.e., re-lyophilized). In another embodiment, the cartilage particles resulting from the freeze-milling process may be rehydrated before re-lyophilization. In another embodiment, the cartilage particles resulting from the freeze-milling process may be inserted into a construct, and relyophilized together with the construct.

The cartilage particles may range from about 15% to about 50%, by weight, of a gel or paste (in one embodiment, about 22%), and may be mixed with a biocompatible carrier, which constitutes the remaining weight of the gel or paste. The biocompatible carrier is preferably bioabsorbable. The carrier may have a composition that includes one or more of the following: phosphate buffered saline (PBS) solution, saline solution, sodium hyaluronate solution (HA) (molecular weight ranging from $7.0 \times 10^5$ to $1.2 \times 10^6$), hyaluronic acid and its derivatives, gelatin, collagen, chitosan, alginate, Dextran, sterile water, carboxymethylcellulose (CMC), hydroxypropyl methylcellulose, polymers, blood and/or plasma.

The cartilage particles can be freeze-milled to have various particle sizes, and the carrier can have different viscosities, depending on the desired consistency of the gel or paste. The cartilage gel or paste can be deposited into the cap member, as described herein. The cartilage gel or paste enhances the tissue integration between the allograft construct and adjacent host tissue. For example, the use of cartilage gel or paste in repairing an articular cartilage defect may result in the production of new, well-organized articular cartilage tissue, accompanied by a restored "tidemark".

A method of placing the cartilage defect repair material (i.e., the cartilage particle mixture disclosed herein, including a bioabsorbable carrier) in a cartilage defect site may include the steps of (a) cutting a patient's tissue to remove diseased cartilage from the cartilage defect site; (b) placing the cartilage particle mixture into the cartilage defect site; and (c) placing a cover over the placed mixture.

A method of repairing articular cartilage according to the present invention may include the step of placing a therapeutically effective amount of the cartilage defect repair material (i.e., the cartilage particle mixture disclosed herein, including a bioabsorbable carrier) into a cartilage defect site, wherein, subsequent to placement of the therapeutically effective amount of the cartilage defect repair material into the cartilage defect site, a greater percentage of repair tissue generated in the cartilage defect site is articular cartilage as compared to equivalent cartilage defect sites left untreated or treated with microfracture. The percentage of repair tissue generated may subsequently be assessed by relative uptake of safranin-o and/or anti-collagen II staining materials by the repair tissue. The percentage of repair tissue generated may subsequently be assessed by relative uptake of Safranin-o and/or anti-collagen II staining materials by the repair tissue.

Endogenous and Exogenous Growth Factors

As discussed above, cartilage paste or gel components are believed to provide the environmental and biochemical cues necessary to elicit a healing response from the cells. For example, cartilage that has been freeze-milled may have greater exposure/bioavailability of different endogenous cytokines, growth factors, etc. relative to the surrounding environment. These may include, without limitation, at least native FGF-2, IGF-1, TGF-β (including TGF-β1), BMP-2, and BMP-14 (GDF-5).

The cartilage particles may be provided alone or optionally packaged with a construct, and may be provided to a medical practitioner without added cells or added growth factors. Such cartilage particles, whether alone or in combination with a construct, are themselves capable of supporting articular cartilage regeneration without the addition of further materials.

As noted herein, the cap member may also be loaded with one or more exogenous chondrogenic growth factor additives, including recombinant or native or variant growth factors of FGF-2, FGF-5, FGF-7, FGF-9, FGF-11, FGF-21, TGF-β (including TGF-β1), BMP-2, BMP-4, BMP-7, BMP-14 (GDF-5), PDGF, VEGF, IGF-1, and bioreactive peptides such as Nell 1 (e.g., UCB1) and TP508. Additional growth factors which can be added include hepatocyte growth factor and platelet-derived growth factor. Other possible additives include human allogeneic or autologous chondrocytes, human allogeneic cells, human allogeneic or autologous bone marrow cells, human allogeneic or autologous stem cells, synovial cells, mesenchymal stem cells, pluripotent stem cells, mesenchymal stem and progenitor cells, stromal cells, cartilage stem cells, demineralized bone matrix, insulin, interleukin-1 receptor antagonist, Indian hedgehog, parathyroid hormone-related peptide, viral vectors for growth factor or DNA delivery, nanoparticles, platelet-rich plasma, fibrin clot, blood, bioabsorbable polymers, hyaluronic acid, bone marrow aspirate, xenogenic chondrocytes and mesenchymal stem cells, naked DNA, and RNA. Any one or more of the above-listed additives may be absorbed or combined with the constructs and/or the aforementioned cartilage particle mixture, or may be added directly to the cartilage particles described herein. As an illustration, a chondrogenic growth factor may be adsorbed into a construct, or into the cartilage particle gel or paste added to the construct, or into both the construct and the cartilage particle gel or paste.

In one embodiment, the growth factor TGF-β is included as an activatable endogenous component and/or as an exogenous component (latent or active) in any of the embodiments disclosed herein. In another embodiment, any member of the growth factor family FGF and/or a natural or recombinant variant thereof is included (as an endogenous component and/or as an exogenous component) in any of the embodiments disclosed herein.

One description of a member of the FGF family's structure and physiological role (particularly relating to enhancing chondrogenesis and chondrogenesis lineage commitment from mesenchymal stem cells) is found in the article "FGF-2 Enhances the Mitotic and Chondrogenic Potentials of Human Adult Bone Marrow-Derived Mesenchymal Stem Cells" (L. A. Solchaga et al., Journal of Cellular Physiology 203:398-409 (2005)), which is incorporated herein by reference in its entirety. In one embodiment, FGF-2 binding enhances chondrocyte proliferation. In one embodiment, FGF-2 binding enhances chondrocyte differentiation. In one embodiment, FGF-2 binding increases chondrocyte aggregation. In one embodiment, FGF-2 binding increases development of chondrocyte-mediated creation of extracellular matrix. In one embodiment, FGF-2 binding increases proteoglycan synthesis. In one embodiment, FGF-2 binding mediates increased collagen type II/type I ratio as compared to control cells. In one embodiment, FGF-2 binding downregulates MAP kinase activities. In one embodiment, FGF-2 binding inhibits MAP kinase activities.

In another embodiment, freeze-milled cartilage particles having at least one dimension that is 212 microns or less are combined with a phosphate buffered saline carrier and an exogenous fibroblast growth factor such as FGF-2 or a variant thereof in a therapeutically effective and/or efficacious dosage. This combination may be infused into the cap member of the construct using the protocol outlined above. In one embodiment, the freeze-milled cartilage particles preferably have at least one dimension within a range of from approximately 10 microns to approximately 212 microns.

In another embodiment, any member of the growth factor family BMP is included (as an endogenous component and/or as an exogenous component) in any of the embodiments disclosed herein. One description of a member of the BMP family's structure and physiological role (particularly relating to initiating chondrogenesis and chondrogenesis lineage commitment from mesenchymal stem cells) is found in the article "BMP2 initiates chondrogenic lineage development of adult human mesenchymal stem cells in high-density culture" (B. Schmitt et al., Differentiation (2003) 71:567-577), incorporated herein by reference in its entirety. In one embodiment, BMP2 may be co-administered with TGF-133 so as to drive chondrocyte differentiation from MSCs (mesenchymal stem cells). In one embodiment, BMP2 may drive selective differentiation. In one embodiment, administration of BMP2 results in substantially no adipocyte or osteoclast cell differentiation. In one embodiment, BMP2 facilitates upregulation of COMP-type II collagen and cartilage oligomeric matrix protein synthesis. In another embodiment, BMP2 facilitates development of high density chondrocyte microenvironments, which may be important for cell-to-cell signaling so as to maintain chondrocyte lineage.

Activation of Latent Endogenous Growth Factors

In one embodiment, the small size of the cartilage particles may facilitate increased activation of various latent forms of growth factors due to the increased aggregate and/or accessible surface area of the cartilage particles used. Examples specific to TGF-β are herein described, but the mechanical, physical and/or chemical activation processes described herein are applicable to a wide range of latent endogenous growth factors.

TGF-β is synthesized and secreted as a biologically inactive or "latent" complex. Activation must occur to release the mature, biologically active, form of TGF-β, for signal transduction. The mechanism of activation of latent TGF-β in vivo is still not completely understood. It may occur by local acidification at the site of action or by endogenous and/or exogenous enzymatic activity, and may also involve integrins, thrombospondin, metalloproteases, plasmin, furin and other proteases. Latent TGF-β (L-TGF-β) can be activated in vitro by acid or alkaline solutions (pH 2 or pH 8, respectively), exposure to heat (e.g., 100° C.), or by treatment with chaotropic agents and substances like SDS (i.e., sodium dodecyl sulfate) and urea. In one embodiment, the molecular weight of TGF-β is reduced from 100 kD to 25 kD prior to or simultaneously with activation.

Various physiological substances have been reported to activate L-TGF-β in vitro studies. Some examples are serine protease, plasmin, other proteases such as endoglycosidase F, sialidase, neuraminidase, cathepsins B and D, calpain, and the glycoprotein, thrombospondin-1, all of which can convert L-TGF-β to biologically active TGF-β. In one embodiment, TGF-β1 is cleaved from the C-terminus of a disulfide-linked dimer of pro-TGF-β1 by a subtilsin-like pro-protein convertase protease. It is normally secreted as an inactive, or latent, complex. Although it is not always stated, the isoform most often described to be susceptible to the actions of the aforementioned substances is TGF-β1.

Increased exposure, release, or activation of various growth factors may also be attributable to pH-mediated physical and/or chemical changes to the tissue. In another embodiment, such pH-mediated physical and/or chemical changes resulting in exposure, release, or activation of various growth factors are attributable to an acidic pH (for example, pH 2). In another embodiment, such pH-mediated physical and/or chemical changes resulting in exposure, release, or activation of various growth factors is attributable to an alkaline pH (for example, pH 8).

Increased exposure, release, or activation of various growth factors may also be attributable to temperature-mediated physical and/or chemical changes to the tissue. In one embodiment, growth factor activation occurs at mammalian body temperature (e.g., 37° C.). In another embodiment, growth factor activation is inhibited at low temperatures (e.g., −40° C.) with a subsequent measurable increase in growth factor structural stability. In one embodiment, the physiological mechanism of release from latency is an important control for the regulation and localization of TGF-β activity. In one embodiment, proteolysis of latent TGF-β is likely a part of the mechanism of release from latency.

Increased exposure, release, or activation of various growth factors may also be attributable to release of endogenous proteases and subsequent protease-mediated physical and/or chemical changes to the tissue. In one embodiment, the endogenous protease is serine protease. In one embodiment, the endogenous protease is a cathepsin. In one embodiment, the endogenous protease is a sialidase. In another embodiment, the sialidase is a neuramidase. In another embodiment, the endogenous protease is an endoglycosidase. In another embodiment, the endoglycosidase is endoglycosidase F, retinoic acid, and/or transglutaminase.

Increased exposure, release, or activation of various growth factors may also be attributable to the release of chaotropic agents and subsequent physical and/or chemical changes to the tissue. Increased exposure, release, or activation of various endogenous growth factors may also be attributable to the mechanical disruption of the freeze-milled cartilage. In another embodiment, increased exposure, release, and/or activation of various growth factors is attributable to the mechanical disruption of the freeze-milled cartilage, resulting in increased exposure of cartilage proteoglycans and other cartilage components to the outside environment.

Increased exposure, release, or activation of various endogenous growth factors may also be attributable to lyophilization of the freeze-milled cartilage, either before or after freeze-milling.

Increased exposure, release, or activation of various endogenous growth factors may also be attributable to conversion of one or more other growth factors from the latent stage.

Growth factor effects may be context-dependent; e.g., a growth factor that would drive osteogenesis in a vascularized environment will drive chondrogenesis in an avascular environment.

In one embodiment, the growth factor isoform often found to be susceptible to the actions of the aforementioned substances and/or manipulations is latent TGF-β1. In another embodiment, the growth factor isoforms often found to be susceptible to the actions of the aforementioned substances and/or manipulations are L-TGF-β2 and L-TGF-β3.

Activation of Exogenous Growth Factors

The cartilage particle gel or paste can also contain exogenous growth factors and/or growth factor activators. The levels of these growth factors may be similar to or greater than the levels of endogenous growth factors in intact cartilage. Exogenous growth factors and/or growth factor activators can also be combined with the cartilage particles. In one embodiment, the cartilage particles are mixed with a growth factor in an aqueous vehicle, lyophilized and stored dry at room temperature. The cartilage particles/growth factor mixture may alternatively be frozen. Alternatively, the cartilage particles/growth factor mixture may be used immediately. In one embodiment, particles containing chondrogenic growth factor(s) can be added to any portion of a construct according to the present invention, and particles containing osteogenic growth factor(s) can be added to any portion of the construct except for the demineralized cancellous cap member.

In one embodiment, the mixture containing the cartilage particles and growth factor can be lyophilized for storage. In one embodiment, the lyophilized cartilage particles and growth factor may have a residual water content that is within a range of from 0.1% to 8.0% by weight.

In another embodiment, the activatable exogenous growth factor can be any one of a variety of growth factors known to promote wound healing, cartilage and/or bone development (e.g., TGF-β).

In another embodiment, the activating agent used to solubilize the growth factor and/or adsorb it into the cartilage particles (or alternately to activate endogenous growth factors present in the freeze-milled cartilage particles) can be saline, water, PBS, Ringers, any agent capable of pH modification or proteolytic activity, etc.

In another embodiment, the resulting enhanced cartilage particles can contain levels of growth factors that are higher than the levels found in intact cartilage. In another embodiment, the cartilage particle mixture can be infused into all or part of the construct. If desired, the cartilage particle mixture can be infused primarily into the demineralized portion(s) of the construct.

In another embodiment, cells which have been collected from the patient or grown outside of the patient can be inserted into the entire construct or into the demineralized portion(s) (e.g., the cap member) thereof before, during or after deposit of the construct into the defect area. Such cells include, for example, allogenic or autologous bone marrow cells, stem cells and chondrocyte cells. A therapeutically effective cellular density may be utilized. In one embodiment, the cellular density of the cells is preferably within a range from $1.0 \times 10^8$ to $5.0 \times 10^8$ cells/cc of cartilage particle paste or gel mixture. In another embodiment, the cellular density of the cells is preferably within a range from $5.0 \times 10^6$ to $1.0 \times 10^8$ cells/cc of cartilage particle paste or gel mixture.

In another embodiment, any of the methods of the instant invention can be utilized to repair or stimulate growth of meniscus, muscle, tendons, ligaments, skin, periosteum and fat tissue. In another embodiment, meniscus, muscle, tendons, ligaments, skin, periosteum and/or fat tissue may itself be particularized and subsequently utilized to repair analogous and/or nonanalogous tissues.

The following examples further illustrate aspects of the various embodiments of the present invention.

EXAMPLE 1

Measurement of Demineralized Construct Porosity

Figure 34A:
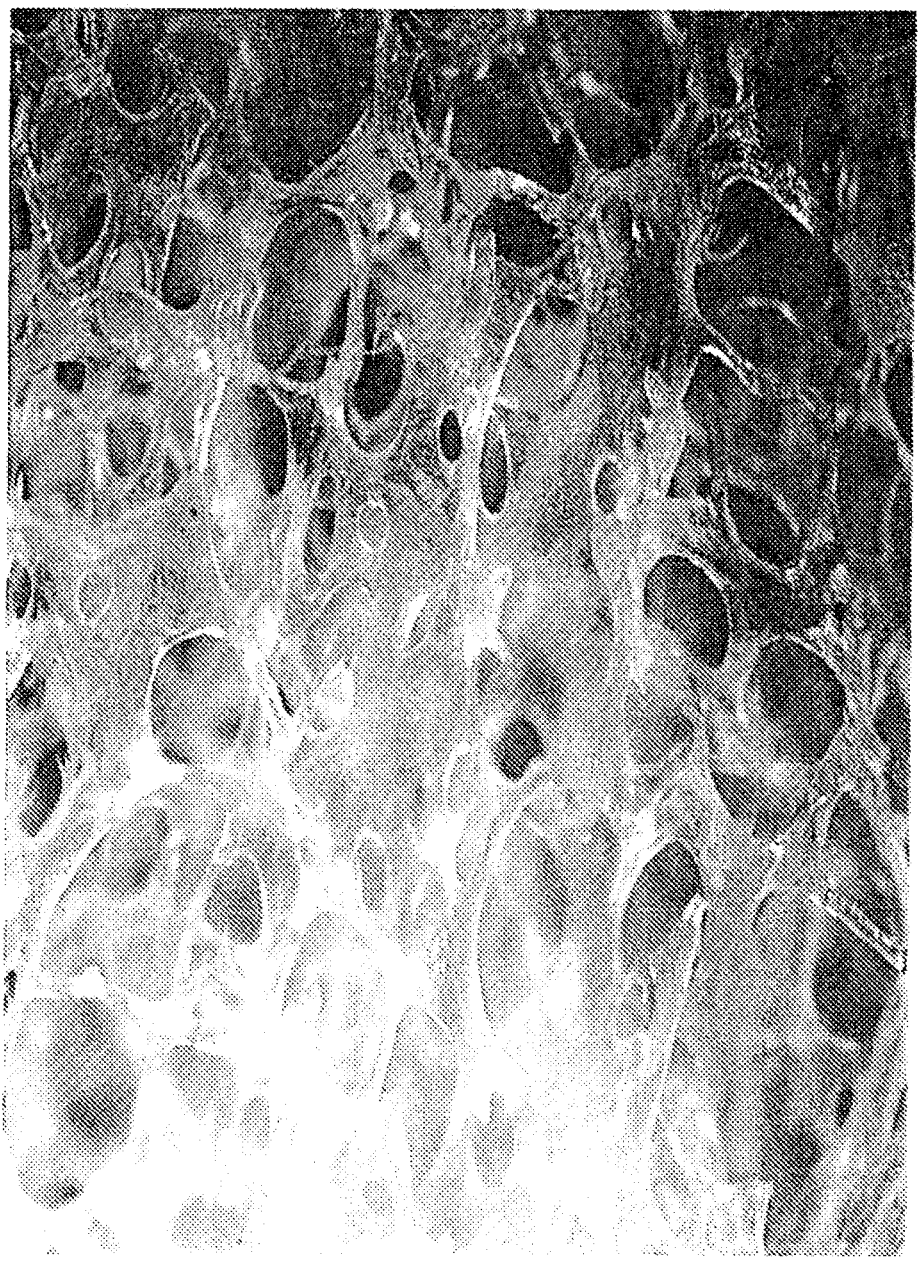
FIGS. 34A and 34B are photographic depictions of the porosity of a demineralized component of a cancellous construct produced in accordance with an embodiment of the present invention.
Figure 34B:
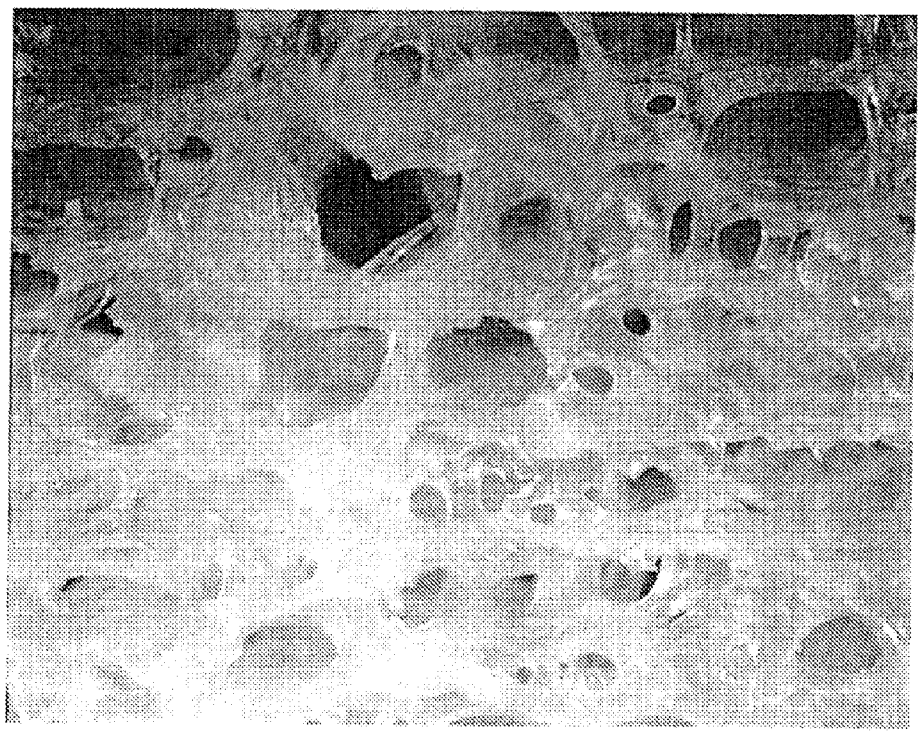

The percentage of porosity and average surface pore diameter of a cancellous construct demineralized cap member according to the present invention can be determined utilizing a microscope/infrared camera and associated computer analysis. The microscope/infrared camera was used to produce the images of FIGS. 34A and 34B, which provide a visual assessment of the porosity of the demineralized cap member of the constructs of the present invention. Such images were analyzed using suitable microscopy and image analysis software, for example, Image Pro Plus. The number and diameter of pores and the relative porosity of a demineralized cap member of the construct can be characterized using techniques known to those skilled in the art.

It is noted that the number and diameter of pores and the relative porosity of the demineralized cap members will vary from one tissue donor to another, and even within the tissue of one tissue donor, based on the anatomical and/or physical properties of the allograft cancellous bone from which the demineralized cap member is derived.

EXAMPLE 2

Tissue Extraction and Particularization

A process of cartilage particle extraction may be applied to any of a number of different soft tissue types (for example, meniscus tissue). Cartilage is recovered from deceased human donors, and the tissue is treated with a soft tissue processing system for bioburden reduction, for example, as disclosed in U.S. Patent Application Publication No. US 2006/0275377 A1 of U.S. patent application Ser. No. 11/375,026, which is incorporated by reference herein in its entirety.

Fresh articular cartilage is removed from a donor using a scalpel, taking care to remove the cartilage so that the full thickness of the cartilage is intact (excluding any bone). Removed cartilage is then packaged in double Kapak® bags for storage until ready to conduct chemical cleaning of the allograft tissue, for example, in accordance with U.S. Patent Application Publication No. US 2006/0275377 A1. In one example, the cartilage can be stored in the refrigerator for 24-72 hours or in the freezer (e.g., at a temperature of −70° C.) for longer-term storage.

Chemical cleaning of cartilage tissue is then conducted according to methods known by those skilled in the art. Subsequent to chemical cleaning, the cartilage is lyophilized, so as to reduce the water content of the cartilage tissue to within the range of about 0.1% to about 8.0%.

Subsequent to the initial lyophilization, the cartilage is freeze-milled, wherein the cartilage is frozen (for example, with liquid nitrogen as a freezing agent) and ground into particles. The cartilage particles are sieved, for example, through a 212 micron sieve.

Next, the lyophilized, freeze-milled cartilage particles are processed into a gel or paste through a combination of the freeze-milled cartilage particles with PBS. Exogenous growth factors are optionally added at this stage, and the cartilage particles/exogenous growth factor/PBS mixture is optionally left to equilibrate. Optionally, growth factor may be added to the cartilage particles without or prior to subsequent processing into a gel or paste. The gel or paste may be optionally lyophilized again subsequent to the addition of growth factors.

The cartilage particle gel or paste is then loaded into the demineralized portion of the construct (i.e., the demineralized cap member of the construct, or a demineralized portion of the cap member). The amount of cartilage particle gel or paste loaded into the demineralized portion varies, is characterizable by any of a number of methods known to those of ordinary skill in the art, and is dependent at least on such factors as the volume of the demineralized portion of the construct; the average pore size of the demineralized portion; the average porosity of the construct; and the average and median size of the cartilage particles within the cartilage gel or paste.

The cartilage particle gel- or paste-loaded construct is then packaged for a second lyophilization step. The cartilage particle gel- or paste-loaded construct is lyophilized and may then be provided for surgery, or maintained for later use.

EXAMPLE 3

Extraction of Proteins from Human Cartilage Using Extraction and Subsequent Dialysis In another example, growth factors may be physically and/or chemically isolated from cartilage particles, and dialyzed using a suitable agent. The growth factors are thereby isolated for subsequent analysis and/or quantification. In one embodiment, 0.3 g of cartilage particles were weighed out for each donor. The cartilage particles were transferred to tubes containing 5 ml of extraction solution (4M Guanidine HCl in Tris HCl). The cartilage particles were incubated at 4° C. on an orbital shaker at 60 RPM for 24 hours, followed by dialysis (8 k MWCO membrane dialysis tube) in 0.05M TrisHCl or PBS for 15 hrs. at 4° C. The dialysis solution was then replaced and the dialysis continued for another 8 hrs. at 4° C. The post-dialysis extracts were stored at −70° C. until the ELISA was run.

EXAMPLE 4

ELISA Analysis of Endogenous Growth Factors in Cartilage Particles

The quantities and concentrations of various endogenous growth factors isolated from cartilage may be assessed utilizing ELISA technology. ELISA analysis may be conducted using any available ELISA protocol, including, but not limited to, R&D System's ELISA kit and ProMega's TGF-β Emax™ ImmunoAssay System.

EXAMPLE 5

Figure 35:
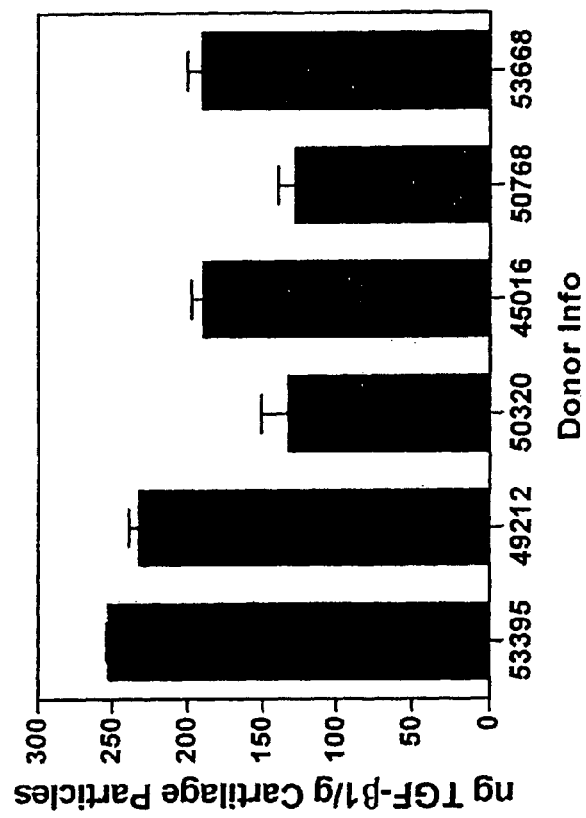
FIG. 35 is a depiction of nanograms of endogenous TGF-$\beta 1$ per gram of cartilage particles isolated from said cartilage particles of several subjects through guanidine HCl extraction and subsequent dialysis.

Quantification of Endogenous Growth Factors Present in Freeze-Milled Cartilage 0.3 g of freeze-milled cartilage particles were weighed out for each tissue donor. The cartilage particles were transferred to tubes containing 5 ml of extraction solution (4M Guanidine HCl in TrisHCl). The cartilage particles were incubated at 4° C. on the orbital shaker at 60 rpm for 24 hrs, followed by dialysis (8 k MWCO membrane dialysis tube) in 0.05M TrisHCl or PBS for 15 hrs at 4° C. The dialysis solution was then replaced and the dialysis continued for another 8 hrs at 4° C. The post-dialysis extracts were stored at −70° C. until the ELISA was run. Notably, the above protocol can also be utilized in order to determine the total endogenous growth factor concentration present in a device (i.e., construct, scaffold, etc.) of the instant invention. FIG. 35 demonstrates the relative concentration of endogenous total TGF-β1 found in freeze-milled cartilage particles of the present invention derived from various tissue donors.

EXAMPLE 6

Increased Availability of Endogenous TGF-β1 from Freeze-Milled Cartilage

Figure 36:
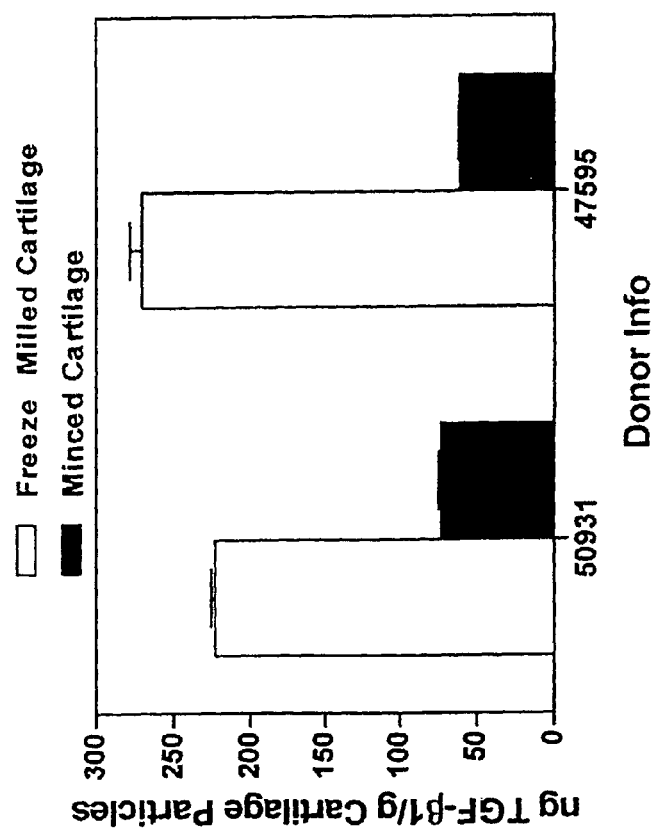
FIG. 36 is a comparison of relative amounts (nanograms) of endogenous TGF-$\beta 1$ per gram of cartilage particles isolated from minced and freeze-milled cartilage through guanidine HCl extraction and subsequent dialysis.

In order to assess the relative amounts of endogenous TGF-β1 accessible via guanidine extraction, the guanidine extraction of endogenous TGF-β1 from minced (e.g., not freeze-milled) cartilage pieces was compared to the guanidine extraction of TGF-β1 from freeze-milled, processed cartilage particles. Increased amounts of endogenous TGF-β1 may be extractable from freeze-milled cartilage particles, as opposed to minced (e.g., not freeze-milled) cartilage pieces. This may be attributable to the increased surface area of the freeze-milled cartilage particles. For example, the fracture planes; three-dimensional shape of the particles; and resultant increased surface area may enhance the release of the cartilage growth factor(s) or other substances from the particles, or the accessibility of growth factors to surrounding cells. This may influence bioavailability of endogenous growth factors and activation of latent endogenous growth factors. Furthermore, the avoidance of elevated temperatures during processing may facilitate the production of particles having high chondrogenic activity by facilitating substantial preservation of extracellular matrix components. For example, preservation of the required tertiary or quaternary folding structures of endogenous growth factors or other proteins in tissue subjected to freeze-milling may occur. FIG. 36 provides an indication of the relative amounts of growth factor that were isolated from minced cartilage and from the freeze-milled cartilage particles of the present invention, respectively.

EXAMPLE 7

Figure 37:
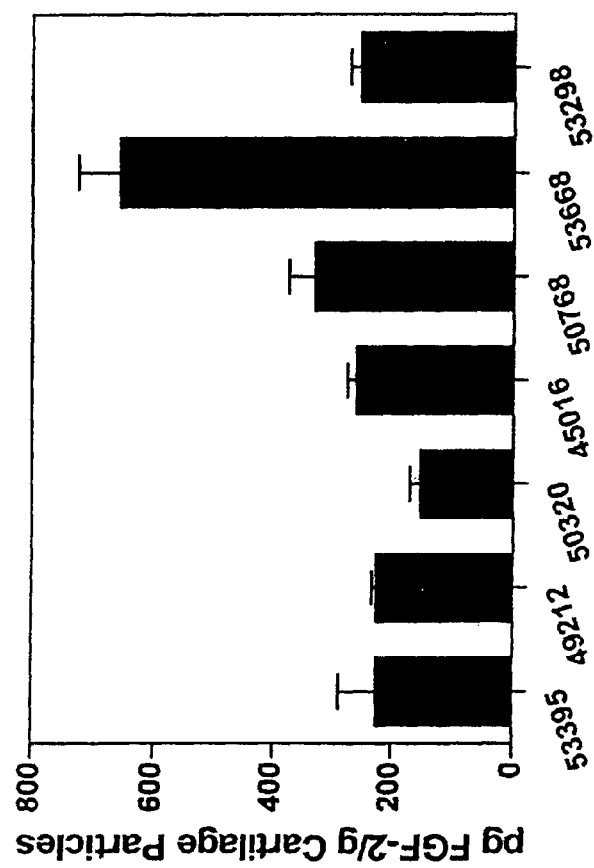
FIG. 37 is a depiction of picograms of endogenous FGF-2 per gram of cartilage particles isolated from freeze-milled cartilage particles of several tissue donors through guanidine HCl extraction and subsequent dialysis.

Quantification of Total Endogenous FGF-2 Present in Freeze-Milled Cartilage Particles FIG. 37 demonstrates the relative concentration of endogenous FGF-2 found in freeze-milled cartilage particles of the present invention that were prepared in accordance with Example 2 of the present invention and derived from various tissue donors.

EXAMPLE 8

Figure 38:
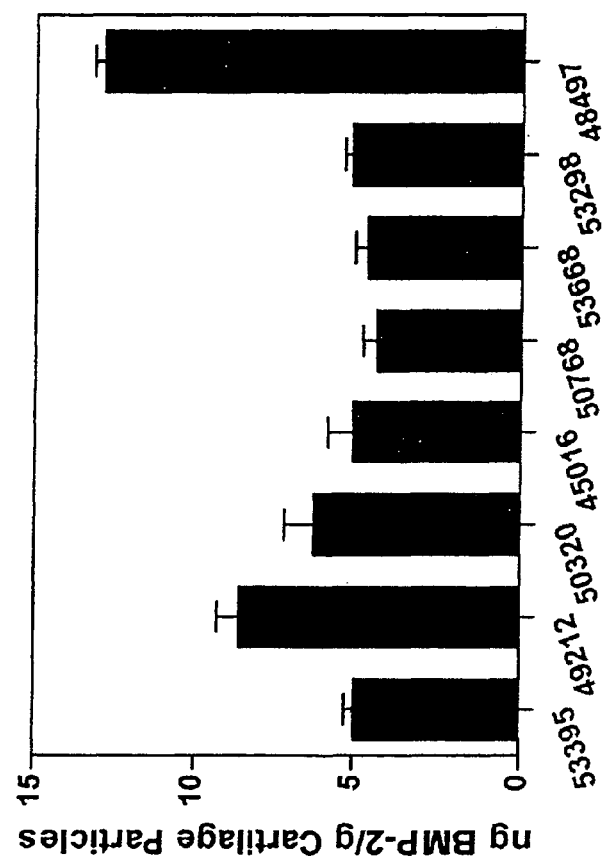
FIG. 38 is a depiction of nanograms of endogenous BMP-2 per gram of cartilage particles isolated from freeze-milled cartilage particles of several tissue donors through guanidine HCl extraction and subsequent dialysis.

Quantification of Total Endogenous Bmp-2 Present in Freeze-Milled Cartilage Particles FIG. 38 demonstrates the relative concentration of endogenous BMP-2 found in freeze-milled cartilage particles of the present invention that were prepared in accordance with Example 2 of the present invention and derived from various tissue donors.

EXAMPLE 9

Figure 39:
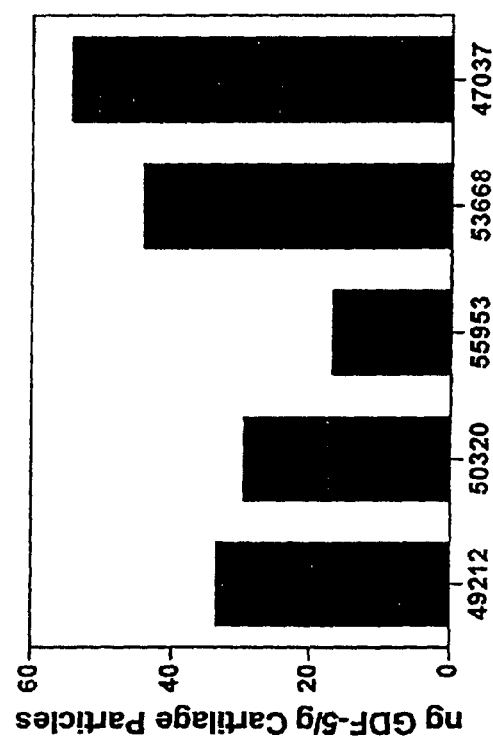
FIG. 39 is a depiction of nanograms of endogenous BMP-14 (GDF-5) per gram of cartilage particles isolated from freeze-milled cartilage particles of several tissue donors through guanidine HCl extraction and subsequent dialysis.

Quantification of Total Endogenous GDF-5/BMP-14 Present in Freeze-Milled Cartilage Particles FIG. 39 demonstrates the relative concentration of endogenous GDF-5/BMP-14 found in freeze-milled cartilage particles of the present invention that were prepared in accordance with Example 2 of the present invention and derived from various tissue donors.

EXAMPLE 10

Figure 40:
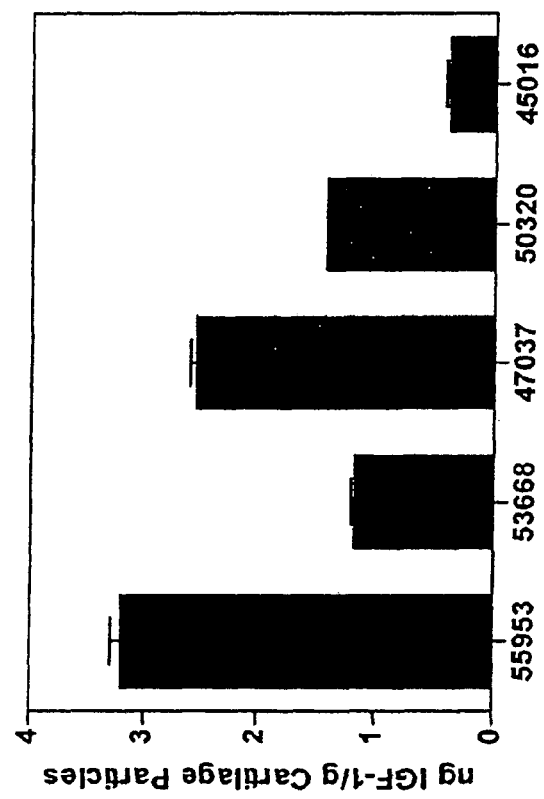
FIG. 40 is a depiction of nanograms of endogenous IGF-1 per gram of cartilage particles isolated from freeze-milled cartilage particles of several tissue donors through guanidine HCl extraction and subsequent dialysis.

Quantification of Total Endogenous IGF-1 Present in Freeze-Milled Cartilage Particles FIG. 40 demonstrates the relative concentration of endogenous IGF-1 found in freeze-milled cartilage particles of the present invention that were prepared in accordance with Example 2 of the present invention and derived from various tissue donors.

As shown in the included tables and figures, freeze-milled cartilage particles, minced cartilage, and native cartilage all retain a concentration of endogenous TGF-β1. Such concentration of TGF-β1 is more bioavailable in the freeze-milled particles described herein. Freeze-milled cartilage particles as described herein also retain a concentration of endogenous BMP-2; BMP-14/GDF-5; IGF-1; and FGF-2.

EXAMPLE 11

Relative Efficacy of Various Cartilage Paste and Clinical Standard Methods in Particular Cartilage Reconstruction In Vivo (Microfracture)

An animal study was conducted using critical sized defects in Spanish goats to determine the cartilage healing potential of the three cartilage particle paste preparations listed in TABLE 1 below. Chondral defects were created on the medial femoral condyle (6 mm diameter) and trochlear sulcus (5 mm diameter) followed by microfracture and implantation of the cartilage paste.

TABLE 1

| Implant | Procedure | Splint Time | # of Goats | Study Time |
|---|---|---|---|---|
| Particles in PBS | Microfracture | 3, 7, or 14 days | 3 | 6 weeks |
| Particles in Hy | Microfracture | 3, 7, or 14 days | 3 | 6 weeks |
| Particles in Hy + Insulin | Microfracture | 3, 7, or 14 days | 3 | 6 weeks |

All of the animals exhibited some circumferential healing in one or more of the defects. This ranged from 0 to 75% in the medial femoral condyle lesion areas being filled with repair tissue, and from 0 to 90% in the trochlear sulcus lesion areas being filled with repair tissue.

Figure 41:
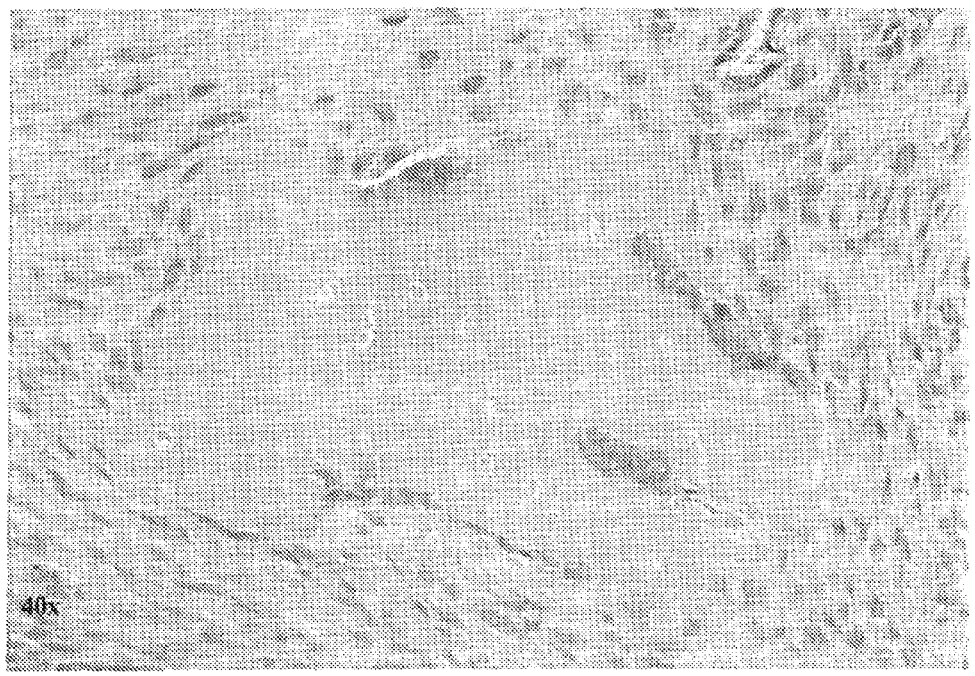
FIG. 41 is a view of newly synthesized articular cartilage from in vivo experimentation, demonstrating infiltration of lacunae by chondrocytes.
Figure 42A:
FIGS. 42A and 42B are views of collagen immunohistochemistry staining for collagen II, a marker of articular cartilage, showing that both cartilage particles and newly-synthesized extracellular matrix stain positive for collagen II.
Figure 42B:
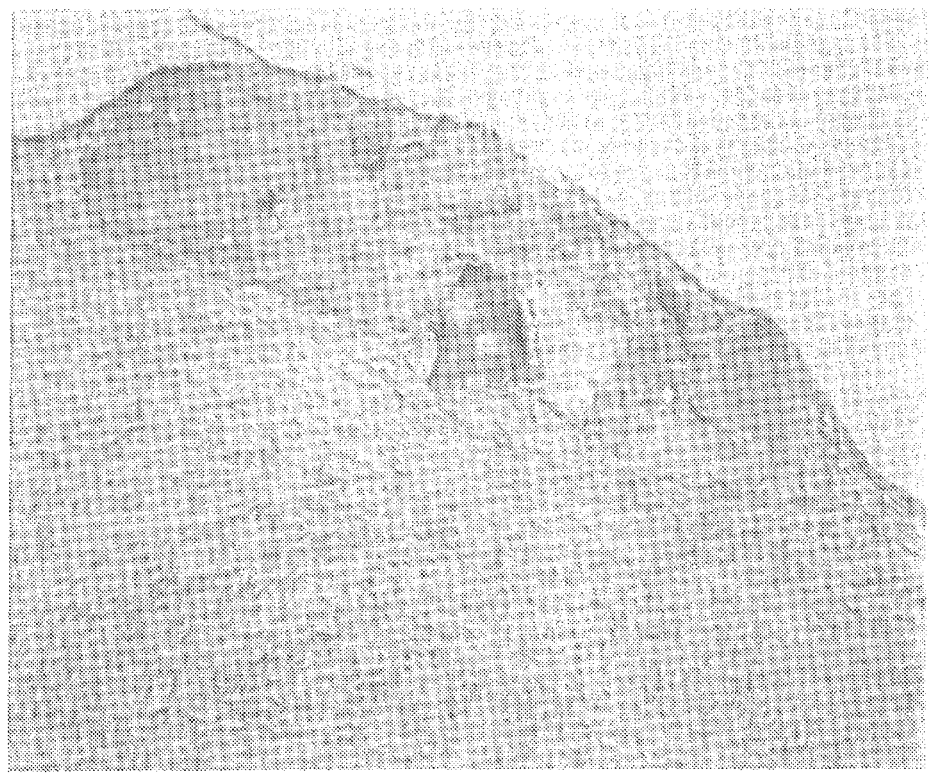

Histologically, it was observed that where the cartilage paste was retained in the defect, the repair tissue was positive for glycosaminoglycans (GAG) and collagen II, which indicated the presence of articular cartilage. This occurred most frequently around the edges of the defect, where the cartilage paste had a better chance of staying in place. See FIG. 41 (demonstrating infiltration of lacunae by chondrocytes); FIGS. 42A-B (residual and new collagen type II, respectively, as visualized via immunohistochemistry).

EXAMPLE 12

Figure 43:
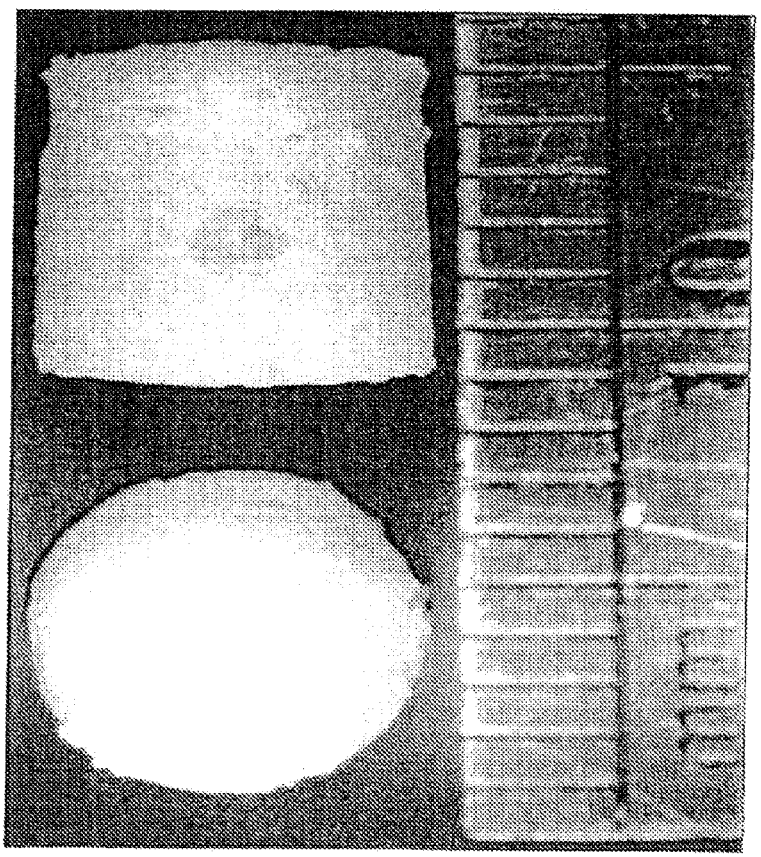
FIG. 43 is a pictorial depiction of a cancellous construct, for example, of the type disclosed in the instant application.
Figure 44:
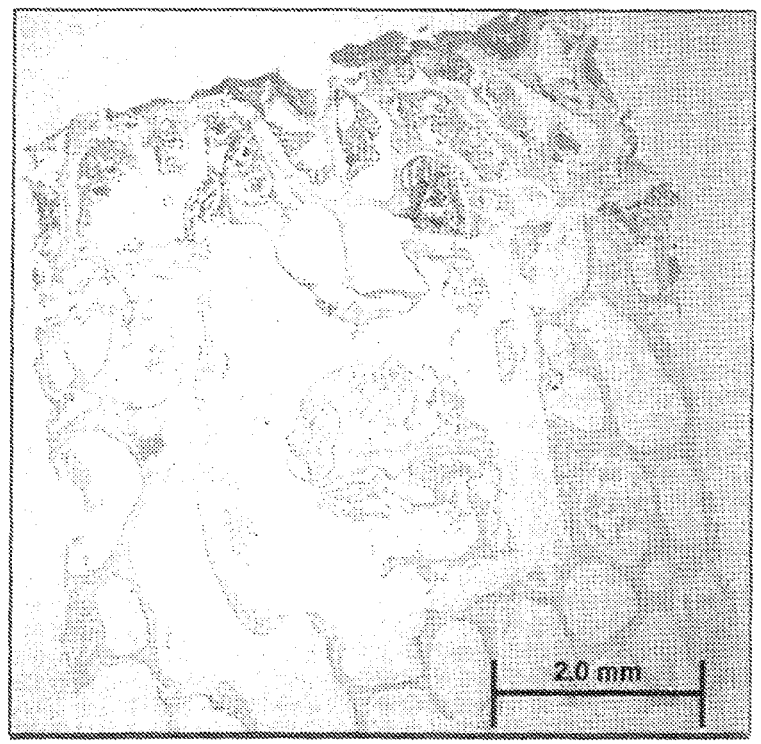
FIG. 44 demonstrates homogenous distribution of the cartilage particles in a cap portion of the construct, as indicated by positive proteoglycan (Safranin-O) staining.

Comparative In Vivo Study of Articular Cartilage Regeneration of Induced Osteochondral Defects An in vivo animal study was conducted on critical sized defects in Spanish goats, utilizing constructs such as disclosed herein combined with various cartilage particle preparations. FIG. 43 is a photographic depiction of a construct such as disclosed herein and utilized in the study. FIG. 44 depicts homogenous distribution of infused cartilage particles in a construct, as determined by Safranin-o (proteoglycan) staining.

TABLE 2 below details the content of each implant used in the study, each of which was assayed in duplicate (12 and 24 weeks duration in vivo implantation). "MFX" refers to the microfracture procedure performed in the defect that was used as a control (i.e., without the implantation of constructs or cartilage particles). "ACS" refers to "allograft cartilage scaffold", incorporating embodiments of both the cartilage particles and the constructs of the instant application.

TABLE 2

| Group # | Implant | Splint Time (days) | # of Defects | Survival (weeks) | # Goats |
|---|---|---|---|---|---|
| 1 | Empty Defect | 7 | 2 | 12, 24 | 2 |
| 2 | MFX Control | 7 | 2 | 12, 24 | 2 |
| 3 | ACS No Particles | 7 | 2 | 12, 24 | 5 |
| 4 | ACS | 7 | 2 | 12, 24 | 5 |

Figure 45A:
FIGS. 45A-45H demonstrate relative chondrogenesis over a period of 24 weeks post-treatment.
Figure 45B:
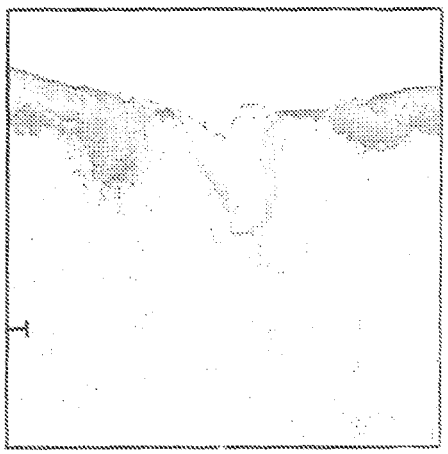
Figure 45C:
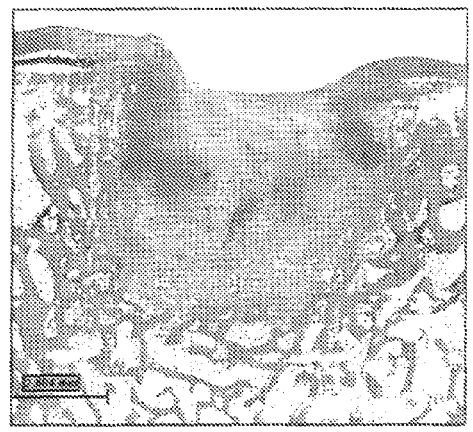
Figure 45D:
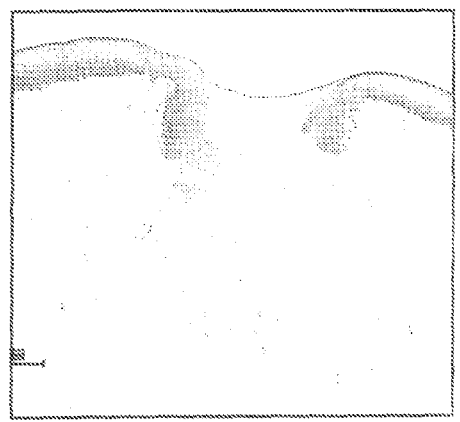
Figure 45E:
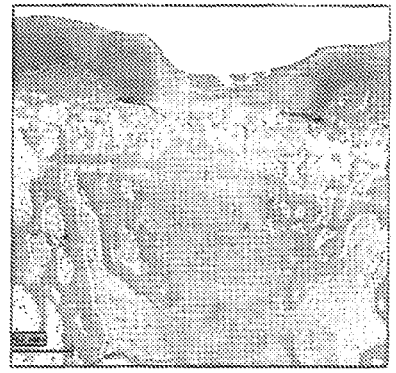
Figure 45F:
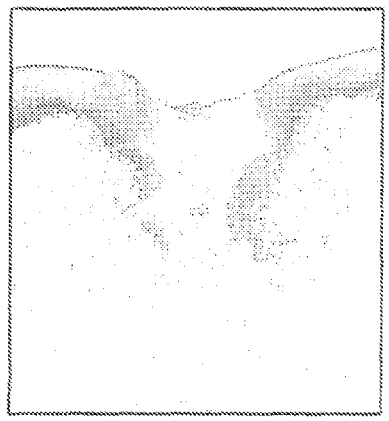
Figure 45G:
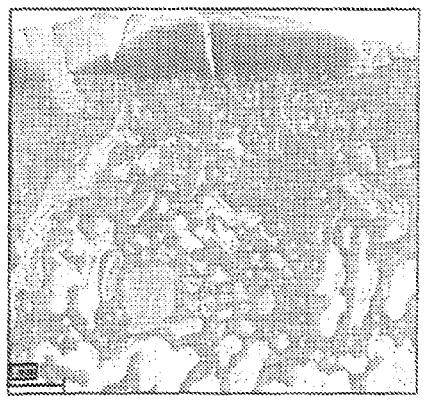
Figure 45H:
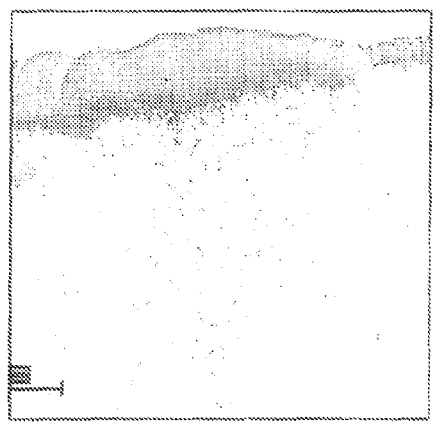

FIGS. 45A-H demonstrate improved and selective chondrogenesis when constructs and freeze-milled cartilage particles of the instant invention are used in conjunction. FIGS. 45A, 45C, 45E and 45G show tissues stained with Safranin-O for proteoglycan assessment. FIGS. 45B, 45D, 45F and 45H show tissues stained with anti-collagen II antibodies. FIGS. 45A and 45B depict microfracture (Group 2); FIGS. 45C and 45D depict an empty defect (Group 1); FIGS. 45E and 45F depict a construct without cartilage particles (Group 3); and FIGS. 45G and 45H depict a construct with infused freeze-milled cartilage particles. (Group 4).

Examples 13-16 below include data from a particle size analysis conducted on a sample of allograft cartilage particles from four different tissue donors in a dry state. An analysis of cartilage particles from the donors was also conduced after the particles were mixed with one of the following carriers: hyaluronic acid (Hy) paste, PBS and Ringers. The cartilage particles in the carriers were measured at 1 hour, 8 hours and 24 hours.

The particle size analysis was conducted on a Malvern MasterSizer Laser diffractor (Malvern Instruments Ltd., Worcestershire, United Kingdom) that calculated a volume distribution from the laser diffraction pattern. The raw scatter data was then processed using a complex algorithm resulting in an equivalent spherical diameter for the particles. The equivalent spherical diameter of an irregularly-shaped object, such as the particles, is the diameter of a sphere of equivalent volume as the object.

Of the dry cartilage particles that were analyzed, at least 95% of the particles had an equivalent spherical diameter of less than 100 microns, while at least 90% of the particles had an equivalent spherical diameter of less than 60 microns. The cartilage particles in the carriers had larger equivalent spherical diameters than those of the dry particles, which may have been attributable to the swelling of the particles in the carriers and/or to the agglomeration of the particles when mixed with the carriers. Based on the results of the analysis, the cartilage particles were concluded to have equivalent spherical diameters of less than 100 microns.

EXAMPLE 13

Particle Size Analysis of Cartilage Particles (Donor #1)

Cartilage particles derived from a 30 year old male tissue donor were pre-weighed and sent to Particle Technology Labs, Ltd. (Downers Grove, Ill.) for evaluation on the microscope using Image-Pro (Bethesda, Md.) analysis to determine their particle size dry. The cartilage was lyophilized and freeze-milled prior to evaluation. 0.2 grams of cartilage particles were set aside for dry analysis.

A total of 4,242 cartilage particles were analyzed. The equivalent spherical diameter of the particles ranged from less than 31.95 microns to 351.44 microns. According to the analysis, 2.59% of the particles had an equivalent spherical diameter greater than 95.85 microns, and 88.99% of the particles had an equivalent spherical diameter less than 31.95 microns. The arithmetic mean equivalent spherical diameter was 26.06 microns. The median equivalent spherical diameter was 11.30 microns. The mode equivalent spherical diameter was 31.95 microns. The data is presented in Table 3 below.

TABLE 3

Cartilage Particles Size Analysis Results for Donor #1

| Cumulative % Indicated Size | Equivalent Spherical Diameter (microns) | Equivalent Spherical Volume (cubic microns) |
|---|---|---|
| 88.99% | 31.95 | 17,095.24 |
| 94.81% | 63.9 | 136,633.6 |
| 97.41% | 95.85 | 461,282.74 |
| 98.42% | 127.8 | 1,093,068.8 |
| 99.15% | 159.75 | 2,135,300.9 |
| 99.48% | 191.69 | 3,689,107.1 |
| 99.72% | 223.64 | 5,857,379.7 |
| 99.83% | 255.59 | 8,744,550.3 |
| 99.93% | 287.54 | 12,449,438 |
| 100.00% | 319.49 | 17,079,200 |
| 100.00% | 351.44 | 22,730,474 |

EXAMPLE 14

Particle Size Analysis of Cartilage Particles (Donor #2)

Cartilage particles derived from a 50 year old female tissue donor were pre-weighed and sent to Particle Technology Labs, Ltd. (Downers Grove, Ill.) for evaluation on the microscope using Image-Pro (Bethesda, Md.) analysis to determine their particle size dry. The cartilage was lyophilized and freeze-milled prior to evaluation. 0.22 grams of cartilage particles were set aside for dry analysis.

A total of 2,174 cartilage particles were analyzed. The equivalent spherical diameter of the particles ranged from less than 24.62 microns to 270.79 microns. According to the analysis, 3.5% of the particles had an equivalent spherical diameter greater than 98.47 microns, and 88.22% of the particles had an equivalent spherical diameter less than 24.62 microns. The arithmetic mean equivalent spherical diameter was 24.04 microns. The median equivalent spherical diameter was 8.700 microns. The mode equivalent spherical diameter was 24.62 microns. The data is presented in Table 4 below.

TABLE 4

Cartilage Particles Size Analysis Results for Donor #2

| Cumulative % Indicated Size | Equivalent Spherical Diameter (microns) | Equivalent Spherical Volume (cubic microns) |
|---|---|---|
| 88.22% | 24.62 | 7,814.82 |
| 92.73% | 49.23 | 62,518.57 |
| 95.08% | 73.85 | 211,000.19 |
| 96.50% | 98.47 | 500,148.59 |
| 97.56% | 123.08 | 976,376.67 |
| 98.48% | 147.70 | 1,687,316 |
| 99.17% | 172.32 | 2,679,550.8 |
| 99.49% | 196.93 | 3,999,970 |
| 99.68% | 221.55 | 5,695,462.5 |
| 100.00% | 246.17 | 7,812,917.4 |
| 100.00% | 270.79 | 10,399,223 |

EXAMPLE 15

Particle Size Analysis of Cartilage Particles (Donor #3)

Cartilage particles derived from a 39 year old female tissue donor were pre-weighed and sent to Particle Technology Labs, Ltd. (Downers Grove, Ill.) for evaluation on the microscope using Image-Pro (Bethesda, Md.) analysis to determine their particle size dry. The cartilage was lyophilized and freezer milled prior to evaluation. 0.2 grams of cartilage particles were set aside for dry analysis.

A total of 2,667 cartilage particles were analyzed. The equivalent spherical diameter of the particles ranged from less than 30.01 microns to 330.13 microns. According to the analysis, 2.32% of the particles had an equivalent spherical diameter greater than 90.04 microns, and 91.45% of the particles had an equivalent spherical diameter less than 30.01 microns. The arithmetic mean equivalent spherical diameter was 23.36 microns. The median equivalent spherical diameter was 10.61 microns. The mode equivalent spherical diameter was 30.01 microns. The data is presented in Table 5 below.

TABLE 5

Cartilage Particles Size Analysis Results for Donor #3

| Cumulative % Indicated Size | Equivalent Spherical Diameter (microns) | Equivalent Spherical Volume (cubic microns) |
|---|---|---|
| 91.45% | 30.01 | 14,139 |
| 95.84% | 60.02 | 113,225.15 |
| 97.68% | 90.04 | 382,262.23 |
| 98.65% | 210.08 | 4,855,221.6 |
| 99.21% | 150.06 | 1,769,496.7 |
| 99.59% | 180.07 | 3,058,097.8 |
| 99.65% | 210.08 | 4,855,221.6 |
| 99.74% | 240.09 | 7,248,220.7 |
| 99.89% | 270.11 | 10,321,080 |
| 100.00% | 300.12 | 14,155,974 |
| 100.00% | 330.13 | 18,842,971 |

EXAMPLE 16

Particle Size Analysis of Cartilage Particles (Donor #4)

Cartilage particles derived from a 77 year old male tissue donor were pre-weighed and sent to Particle Technology Labs, Ltd. (Downers Grove, Ill.) for evaluation on the microscope using Image-Pro (Bethesda, Md.) analysis to determine their particle size dry. The cartilage was lyophilized and freezer milled prior to evaluation. 0.22 grams of cartilage particles were set aside for dry analysis.

A total of 3,678 cartilage particles were analyzed. The equivalent spherical diameter of the particles ranged from less than 28.31 microns to 311.45 microns. According to the analysis, 0.6% of the particles had an equivalent spherical diameter greater than 84.94 microns, and 96.87% of the particles had an equivalent spherical diameter less than 28.31 microns. The arithmetic mean equivalent spherical diameter was 15.45 microns. The median equivalent spherical diameter was 10.01 microns. The mode equivalent spherical diameter was 28.31 microns. The data is presented in Table 6 below.

TABLE 6

Cartilage Particles Size Analysis Results for Donor #4

| Cumulative % Indicated Size | Equivalent Spherical Diameter (microns) | Equivalent Spherical Volume (cubic microns) |
|---|---|---|
| 96.87% | 28.31 | 11,894.19 |
| 98.69% | 56.63 | 95,153.48 |
| 99.40% | 84.94 | 320,916.24 |
| 99.76% | 113.25 | 760,824.7 |
| 99.84% | 141.57 | 1,486,143.2 |
| 99.92% | 169.88 | 2,567,330 |
| 99.95% | 198.19 | 4,077,236.3 |
| 99.97% | 226.51 | 6,086,597.6 |
| 99.97% | 254.82 | 8,664,738.6 |
| 100.00% | 283.13 | 11,886,626 |
| 100.00% | 311.45 | 15,822,014 |

EXAMPLE 17

Aspect Ratio Analysis of Cartilage Particles

Cartilage particles derived from three tissue donors were sent to Particle Technology Labs, Ltd. (Downers Grove, Ill.) for evaluation on the microscope using Image-Pro (Bethesda, Md.) analysis to determine the aspect ratio of the particles. The aspect ratio is the ratio of the longest dimension of a particle to the shortest dimension of a particle. The cartilage particles were freeze-dried (i.e., lyophilized), freeze-milled and sieved prior to evaluation.

For the first tissue donor, the aspect ratio of the cartilage particles ranged from 1.0 to 6.77, with a mean aspect ratio of 1.68. For the second tissue donor, the aspect ratio of the cartilage particles ranged from 1.0 to 15.67, with a mean aspect ratio of 1.72. For the third tissue donor, the aspect ratio of the cartilage particles ranged from 1.0 to 5.42, with a mean aspect ratio of 1.57.

Cartilage particle size analysis was performed on three additional tissue donors (Donors A, B and C), as set out in Examples 18-20:

EXAMPLE 18

Particle Size Analysis of Cartilage Particles (Donor A)

Cartilage particles derived from a tissue donor were evaluated at The Musculoskeletal Transplant Foundation (MTF) (Edison, N.J.) on the microscope using Image-Pro analysis to determine their particle size and aspect ratio. The cartilage was lyophilized and freeze-milled prior to evaluation.

Figure 46:
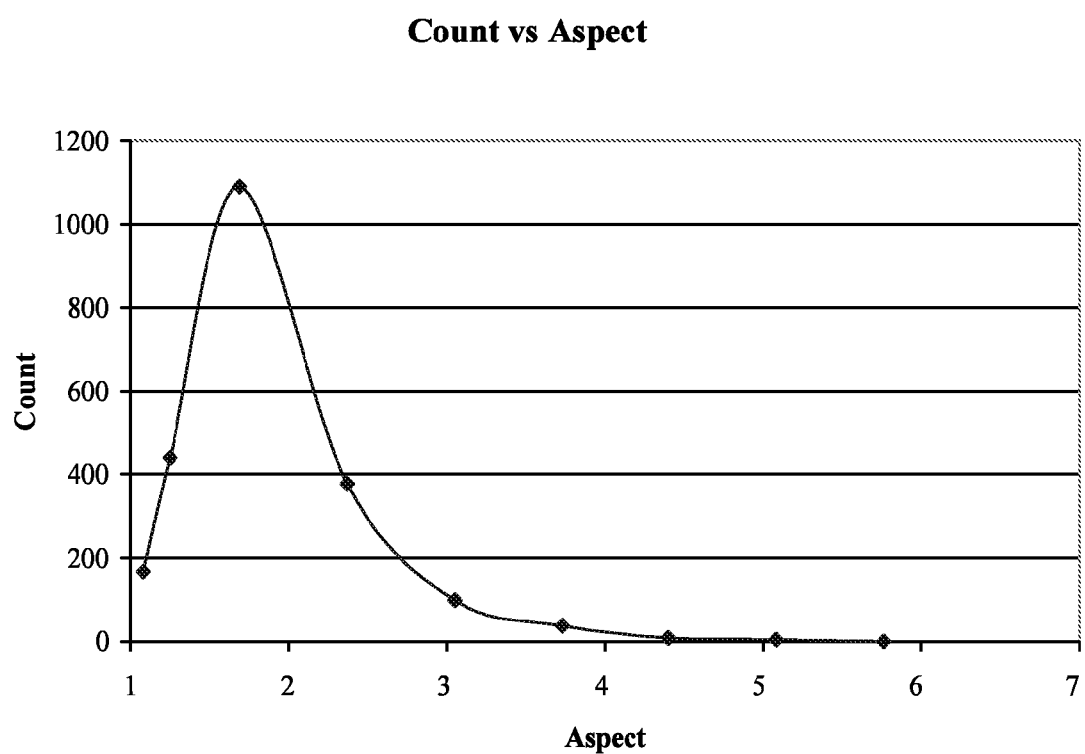
FIGS. 46-48 are graphs of the distribution of the aspect ratios of cartilage particles that were derived from three tissue donors and subjected to a particle size analysis.

The aspect ratio of the particles ranged from 1.0 to 5.3. The arithmetic mean aspect ratio was 1.7. The data from the analysis performed on Tissue Donor #5 is presented in Tables 7 and 8 below, and a graph of the distribution of the aspect ratios of the particles (i.e., particle count vs. aspect ratio) is presented in FIG. 46.

TABLE 7

Cartilage Particles Size Analysis Results for Donor A

| | Particle Area (um)$^2$ | Aspect Ratio | Diameter - Maximum (um) | Diameter - Minimum (um) | Diameter - Mean (um) |
|---|---|---|---|---|---|
| Minimum | 501.2 | 1.0 | 24.8 | 7.5 | 24.8 |
| Maximum | 123357.1 | 5.3 | 760.9 | 259.9 | 430.1 |
| Mean | 4014.3 | 1.7 | 76.9 | 41.3 | 59.4 |
| Std. Dev. | 7766.2 | 0.6 | 59.8 | 23.8 | 39.9 |
| # Particles | 2163 | 2163 | 2163 | 2163 | 2163 |

TABLE 8

Aspect Ratio Analysis Results for Donor A

| Range - Lower Limit | Aspect - Upper Limit | Midpoint | Count within range |
|---|---|---|---|
| 1 | 1.15 | 1.08 | 167 |
| 1.15 | 1.35 | 1.25 | 440 |
| 1.35 | 2.03 | 1.69 | 1091 |
| 2.03 | 2.71 | 2.37 | 378 |
| 2.71 | 3.39 | 3.05 | 98 |
| 3.39 | 4.06 | 3.73 | 37 |
| 4.06 | 4.74 | 4.4 | 8 |
| 4.74 | 5.42 | 5.08 | 4 |
| 5.42 | 6.1 | 5.76 | 0 |
| | TOTAL: | | 2223 |

EXAMPLE 19

Particle Size Analysis of Cartilage Particles (Donor B)

Cartilage particles derived from a tissue donor were evaluated at MTF (Edison, N.J.) on the microscope using Image-Pro analysis to determine their particle size and aspect ratio. The cartilage was lyophilized and freeze-milled prior to evaluation.

Figure 47:
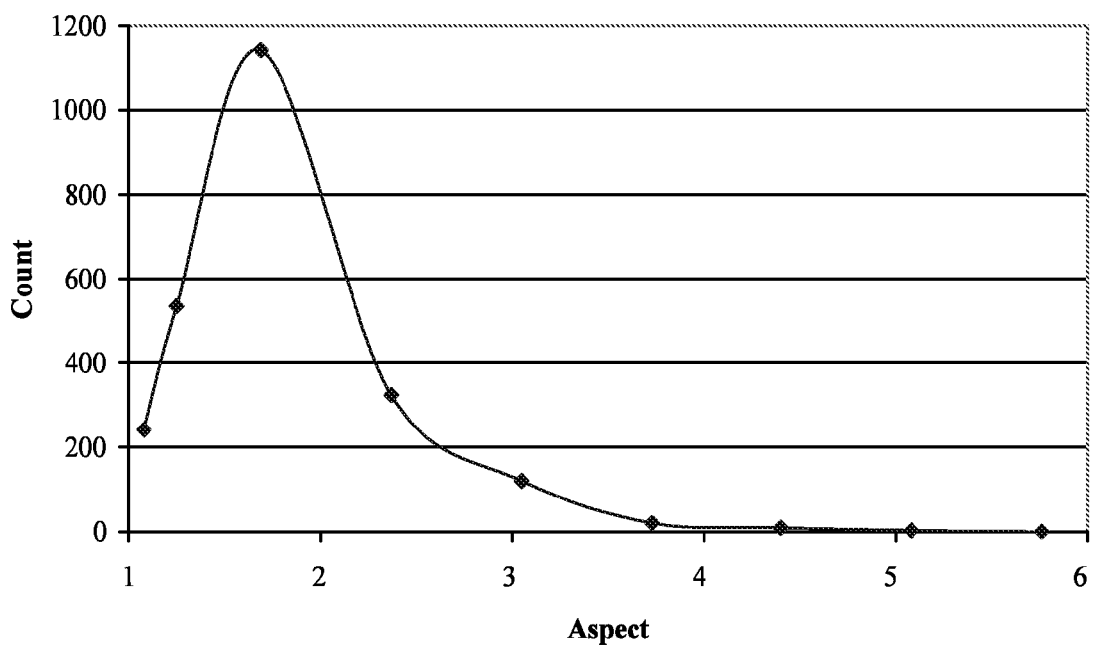

The aspect ratio of the particles ranged from 1.0 to 4.9. The arithmetic mean aspect ratio was 1.7. The data from the analysis performed on Tissue Donor #6 is presented in Tables 9 and 10 below, and a graph of the distribution of the aspect ratios of the particles (i.e., particle count vs. aspect ratio) is presented in FIG. 47.

TABLE 9

Cartilage Particles Size Analysis Results for Donor B

| | Particle Area (um)$^2$ | Aspect Ratio | Diameter - Maximum (um) | Diameter - Minimum (um) | Diameter- Mean (um) |
|---|---|---|---|---|---|
| Minimum | 501.2 | 1.0 | 24.8 | 7.5 | 24.8 |
| Maximum | 163009.6 | 4.9 | 729.9 | 287.1 | 467.4 |
| Mean | 2950.2 | 1.7 | 68.0 | 37.3 | 53.0 |
| Std. Dev. | 5770.6 | 0.6 | 51.9 | 17.1 | 32.4 |
| # Particles | 2319 | 2319 | 2319 | 2319 | 2319 |

TABLE 10

Aspect Ratio Analysis Results for Donor B

| Range - Lower Limit | Aspect - Upper Limit | Midpoint | Count within range |
|---|---|---|---|
| 1 | 1.15 | 1.08 | 242 |
| 1.15 | 1.35 | 1.25 | 535 |
| 1.35 | 2.03 | 1.69 | 1143 |
| 2.03 | 2.71 | 2.37 | 324 |
| 2.71 | 3.39 | 3.05 | 120 |
| 3.39 | 4.06 | 3.73 | 20 |
| 4.06 | 4.74 | 4.4 | 9 |
| 4.74 | 5.42 | 5.08 | 2 |
| 5.42 | 6.1 | 5.76 | 0 |
| | TOTAL: | | 2395 |

EXAMPLE 20

Particle Size Analysis of Cartilage Particles (Donor C)

Cartilage particles derived from a tissue donor were evaluated at MTF (Edison, N.J.) on the microscope using Image-Pro analysis to determine their particle size and aspect ratio. The cartilage was lyophilized and freeze-milled prior to evaluation.

Figure 48:
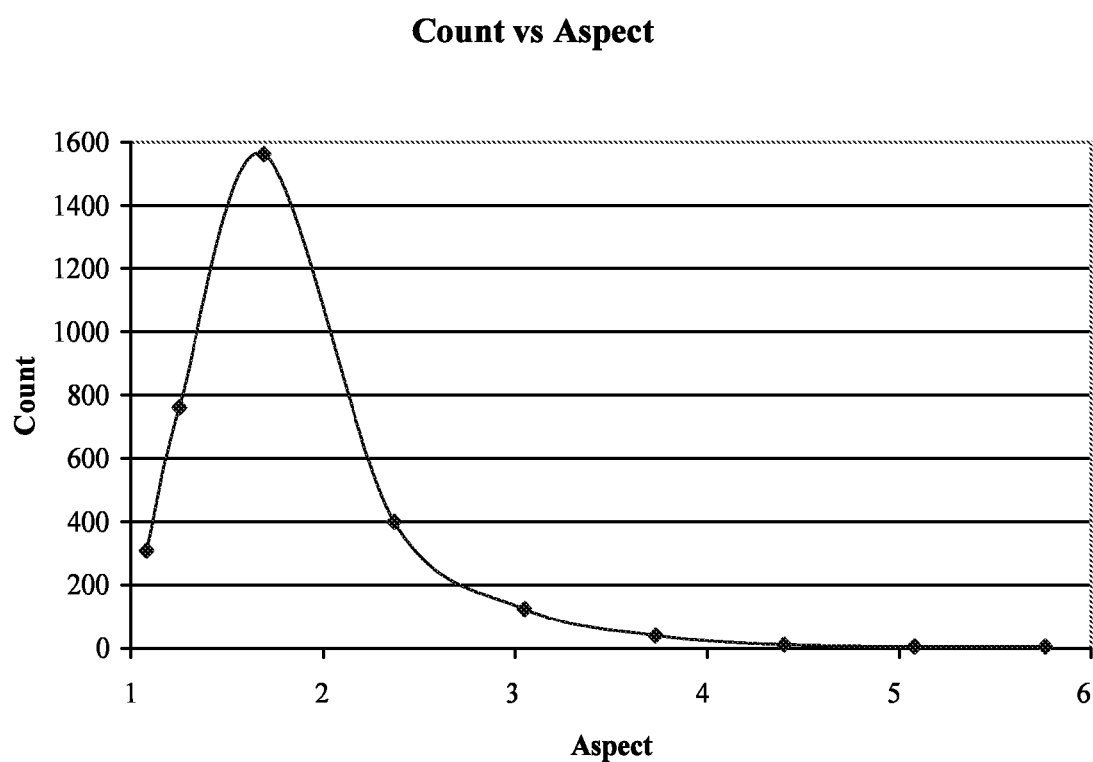

The aspect ratio of the particles ranged from 1.0 to 5.9. The arithmetic mean aspect ratio was 1.7. The data from the analysis performed on Tissue Donor #7 is presented in Tables 11 and 12 below, and a graph of the distribution of the aspect ratios of the particles (i.e., particle count vs. aspect ratio) is presented in FIG. 48.

TABLE 10

Cartilage Particles Size Analysis Results for Donor C

| | Particle Area (um)² | Aspect Ratio | Diameter - Maximum (um) | Diameter - Minimum (um) | Diameter - Mean (um) |
|---|---|---|---|---|---|
| Minimum | 501.2 | 1.0 | 24.8 | 10.5 | 24.8 |
| Maximum | 223824.9 | 5.9 | 959.9 | 262.9 | 600.3 |
| Mean | 4276.3 | 1.7 | 78.8 | 42.6 | 61.2 |
| Std. Dev. | 9218.1 | 0.6 | 67.9 | 22.0 | 43.1 |
| # Particles | 3122 | 3122 | 3122 | 3122 | 3122 |

TABLE 12

Aspect Ratio Analysis Results for Donor C

| Range - Lower Limit | Aspect - Upper Limit | Midpoint | Count within range |
|---|---|---|---|
| 1 | 1.15 | 1.08 | 307 |
| 1.15 | 1.35 | 1.25 | 760 |
| 1.35 | 2.03 | 1.69 | 1560 |
| 2.03 | 2.71 | 2.37 | 400 |
| 2.71 | 3.39 | 3.05 | 124 |
| 3.39 | 4.06 | 3.73 | 40 |
| 4.06 | 4.74 | 4.4 | 11 |
| 4.74 | 5.42 | 5.08 | 4 |
| 5.42 | 6.1 | 5.76 | 4 |
| | TOTAL: | | 3210 |

In one embodiment of the present invention, the cartilage particles have an aspect ratio of less than 3:1.

While a number of embodiments of the present invention have been described, it is understood that these embodiments are illustrative only, and not restrictive, and that many modifications and/or alternative embodiments may become apparent to those of ordinary skill in the art. For example, any steps may be performed in any desired order (and any desired steps may be added and/or any desired steps may be deleted). Therefore, it will be understood that the appended claims are intended to cover all such modifications and embodiments that come within the spirit and scope of the present invention.

What we claim is:

1. A construct for repairing an articular cartilage defect, comprising:
   a cap member having an upper section and a stem depending in a generally axial direction from a central region of said upper section, said upper section including a peripheral region located laterally outwardly from said central region, and said stem having a cavity extending into said stem from a free end of said stem toward said central region of said upper section; and
   a base member having a first end and a second end, said first end including an annular recess extending into said base member in a generally axial direction toward said second end, said annular recess being dimensioned such that said stem of said cap member is receivable in said annular recess, said annular recess having a bottom surface intermediate said first end and said second end of said base member, first supporting means, positioned laterally outwardly from said annular recess, for supporting said peripheral region of said upper section, wherein said first supporting means includes an annular edge of said base member, said annular edge being located at said first end of said base member such that said annular edge abuts said peripheral region of said upper section when said stem of said cap member is received in said annular recess of said base member, and second supporting means, positioned laterally inwardly from said annular recess, for supporting said central region of said upper section, said second supporting means being receivable in said cavity of said stem, wherein said second supporting means includes an island which is surrounded by said annular recess of said base member such that said island abuts said central region of said upper section when said stem of said cap member is received in said annular recess of said base member.

2. The construct of claim 1, further comprising securing means for securing said cap member to said base member when said stem is received in said annular recess.

3. The construct of claim 2, wherein said base member includes a first bore extending generally laterally from an exterior wall of said base member to said annular recess, and said cap member includes a second bore extending generally laterally into said stem from an exterior surface thereof, said second bore being alignable with said first bore when said stem is received in said annular recess, and wherein said securing means includes at least one pin receivable in said first bore and said second bore when said first and second bores are aligned, thereby securing said cap member to said base member.

4. The construct of claim 1, wherein at least a portion of said base member is formed from mineralized bone, and wherein at least said upper section of said cap member is formed from demineralized cancellous bone.

5. The construct of claim 1, wherein said upper section of said cap member includes freeze-milled cartilage particles having a dimension, when dry, that does not exceed 1 mm.

6. The construct of claim 5, wherein said cartilage particles are formed from lyophilized allograft cartilage and have a size within a range from about 10 microns to about 210 microns, said cartilage particles being combined with a carrier and containing at least one endogenous growth factor for promoting the growth of new cartilage at a defect site.

* * * * *

UNITED STATES PATENT AND TRADEMARK OFFICE
CERTIFICATE OF CORRECTION

| | |
|---|---|
| PATENT NO. | : 8,292,968 B2 |
| APPLICATION NO. | : 12/931427 |
| DATED | : October 23, 2012 |
| INVENTOR(S) | : Katherine G. Truncale et al. |

It is certified that error appears in the above-identified patent and that said Letters Patent is hereby corrected as shown below:

Claim 1
Column 48,
Line 36, replace "abuts" with -- is abuttable with --;

Signed and Sealed this
Eighteenth Day of December, 2012

David J. Kappos
*Director of the United States Patent and Trademark Office*